(12) United States Patent
Ichimura et al.

(10) Patent No.: US 7,524,991 B2
(45) Date of Patent: Apr. 28, 2009

(54) ORGANIC ELECTROLUMINESCENT DEVICES, AMINOSTYRYLNAPHTHALENE COMPOUNDS AND SYNTHESIS INTERMEDIATES THEREOF, AND PRODUCTION PROCESSES OF THE SAME

(75) Inventors: Mari Ichimura, Kanagawa (JP); Tadashi Ishibashi, Kanagawa (JP); Shinichiro Tamura, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 11/765,560

(22) Filed: Jun. 20, 2007

(65) Prior Publication Data

US 2008/0051607 A1   Feb. 28, 2008

Related U.S. Application Data

(62) Division of application No. 10/807,984, filed on Mar. 24, 2004, now Pat. No. 7,402,344.

(30) Foreign Application Priority Data

Mar. 24, 2003 (JP) .............................. 2003-079768
Feb. 10, 2004 (JP) .............................. 2004-033056

(51) Int. Cl.
C07C 209/60 (2006.01)

(52) U.S. Cl. ...................................................... 564/393
(58) Field of Classification Search ................. 564/393
See application file for complete search history.

(56) References Cited

U.S. PATENT DOCUMENTS

| | | | |
|---|---|---|---|
| 4,107,444 A | 8/1978 | Martin | |
| 5,399,588 A | 3/1995 | Malamas | |
| 6,177,220 B1 | 1/2001 | Watanabe | |
| 6,228,514 B1 | 5/2001 | Ishibashi | |
| 6,242,116 B1 | 6/2001 | Ishibashi | |
| 6,265,088 B1 | 7/2001 | Ishibashi | |
| 6,337,167 B1 | 1/2002 | Ichimura et al. | |
| 6,440,585 B2 | 8/2002 | Ishibashi | |
| 6,461,779 B1 | 10/2002 | Azuma et al. | |
| 6,492,557 B1 | 12/2002 | Ichimura et al. | |
| 6,495,274 B1 | 12/2002 | Ishibashi et al. | |
| 6,555,254 B1 | 4/2003 | Ishibashi et al. | |
| 6,593,047 B2 | 7/2003 | Azuma et al. | |
| 6,611,554 B1 | 8/2003 | Chouly et al. | |
| 6,680,131 B1 | 1/2004 | Ishibashi et al. | |
| 6,689,493 B2 | 2/2004 | Motomatsu | |
| 6,790,975 B2 | 9/2004 | Ichimura et al. | |
| 6,800,382 B2 | 10/2004 | Ishibashi et al. | |
| 6,972,334 B1 | 12/2005 | Shibanuma et al. | |
| 2002/0045119 A1 | 4/2002 | Azuma et al. | |
| 2002/0106530 A1 | 8/2002 | Ishibashi et al. | |
| 2003/0099863 A1 | 5/2003 | Ishibashi et al. | |
| 2005/0064232 A1 | 3/2005 | Ishibashi et al. | |
| 2005/0158577 A1 | 7/2005 | Ishibashi et al. | |

FOREIGN PATENT DOCUMENTS

| | | |
|---|---|---|
| CZ | 240935 | 7/1986 |
| EP | 1092704 | 4/2001 |
| JP | 02-262563 | 10/1990 |
| JP | 3-200889 | 9/1991 |
| JP | 03-269995 | 12/1991 |
| JP | 11-335307 | 12/1991 |
| JP | 05-041285 | 2/1993 |
| JP | 5-194943 | 3/1993 |
| JP | 5-105645 | 4/1993 |

(Continued)

OTHER PUBLICATIONS

Kim, D. et al; "Synthesis of Organic EL Materials with Cyano Group and Evaluation of Emission Characteristics in Organic EL Devices"; Journal of the Korean Chemical Society (1999), 43(3); 315-320.

(Continued)

*Primary Examiner*—Sikarl A Witherspoon
(74) *Attorney, Agent, or Firm*—Sonnenschein Nath & Rosenthal LLP

(57) ABSTRACT

An organic electroluminescent device includes an anode, a cathode, and an organic layer having a light-emitting area and arranged between the anode and the cathode. The organic layer contains in at least a part thereof at least one aminostyrylnaphthalene compound represented by the following formula [I], [II] or [III]:

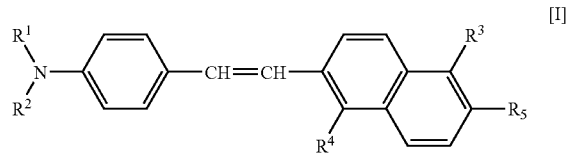

[I]

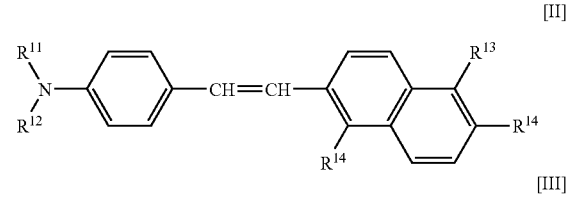

[II]

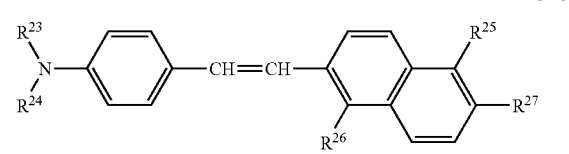

[III]

wherein $R^1$, $R^2$, $R^{11}$, $R^{12}$, $R^{23}$ and $R^{24}$ are each a phenyl or naphthyl group, $R^3$, $R^4$, $R^{13}$, $R^{14}$, $R^{25}$ and $R^{26}$ are each an electron attracting group such as a cyano group, and $R^5$, $R^{15}$ and $R^{27}$ are each a substituent group such as an alkyl group.

5 Claims, 10 Drawing Sheets

FOREIGN PATENT DOCUMENTS

| | | |
|---|---|---|
| JP | 5-320632 | 12/1993 |
| JP | 6-100857 | 4/1994 |
| JP | 6-207170 | 7/1994 |
| JP | 9-268284 | 10/1997 |
| JP | 10-245549 | 9/1998 |
| JP | 11-040359 | 2/1999 |
| JP | 11-102784 | 4/1999 |
| JP | 11-329730 | 11/1999 |
| JP | 11-329731 | 11/1999 |
| JP | 2000-012225 | 1/2000 |
| JP | 2000-012226 | 1/2000 |
| JP | 2000-012227 | 1/2000 |
| JP | 2000-012228 | 1/2000 |
| JP | 2000-136168 | 5/2000 |
| JP | 2000-173773 | 6/2000 |
| JP | 2000-214610 | 8/2000 |
| JP | 2000-230132 | 8/2000 |
| JP | 2001-051433 | 2/2001 |
| JP | 2001-106657 | 4/2001 |
| JP | 2001-106658 | 4/2001 |
| JP | 2001-110570 | 4/2001 |
| JP | 2001-110571 | 4/2001 |
| JP | 2001-337649 | 7/2001 |
| JP | 2001-208488 | 8/2001 |
| JP | 2001-288377 | 10/2001 |
| JP | 2001-291591 | 10/2001 |
| JP | 2001-305754 | 11/2001 |
| JP | 2001-307884 | 11/2001 |
| JP | 2001-307885 | 11/2001 |
| JP | 2002-22672 | 1/2002 |
| JP | 2002-031901 | 1/2002 |
| JP | 2001-337469 | 2/2002 |
| JP | 2002-040676 | 2/2002 |
| JP | 2002-040677 | 2/2002 |
| JP | 2002-072511 | 3/2002 |
| JP | 2002-116560 | 4/2002 |
| JP | 2002-099103 | 5/2002 |
| JP | 2002-131943 | 5/2002 |
| JP | 2002-134276 | 5/2002 |
| JP | 2002-208488 | 7/2002 |
| JP | 2002-226722 | 8/2002 |
| JP | 2002-246175 | 8/2002 |
| WO | WO01/96409 | 12/2001 |
| WO | WO2004/003104 | 8/2004 |

OTHER PUBLICATIONS

Kim, D. et al.; "Synthesis and Emission Characteristics of Novel Red Electroluminescent Dye Containing CN Group"; Bulletin of the Korean Chemical Society (2001) 22(2); 228-230.

Cros, S.; "Heterocycles a fonction quinone 10. Synthese et activie cytoxique de la (diamino-2,4 pyrimidinyl 5)-6 methoy-2 naphtalenedione-1,4"; Journal of Heterocyclic Chemistry; May-Jun. 1987; pp. 571-575.

ORGANIC ELECTROLUMINESCENT DEVICES, AMINOSTYRYLNAPHTHALENE COMPOUNDS AND SYNTHESIS INTERMEDIATES THEREOF, AND PRODUCTION PROCESSES OF THE SAME

RELATED APPLICATION DATA

This application is a divisional of U.S. patent application Ser. No. 10/807,984, filed Mar. 24, 2004, the entirety of which is incorporated herein by reference to the extent permitted by law. The present invention claims priority to Japanese Patent Application No. 2003-079768, filed in the Japanese Patent Office on Mar. 24, 2003, and Japanese Patent Application No. 2004-033056, filed in the Japanese Patent Office on Feb. 10, 2004, the entireties of both of which also are incorporated by reference herein to the extent permitted by law.

BACKGROUND OF THE INVENTION

This invention relates to organic electroluminescent devices, especially organic electroluminescent devices containing aminostyrylnaphthalene compounds useful as electron transport materials, hole transport materials or light emitting materials, the aminostyrylnaphthalene compounds useful in the organic electroluminescent devices and their synthesis intermediates, and production processes of these compounds and intermediates.

In recent years, organic electroluminescent devices (EL devices) are attracting attention as a candidate for flat panel displays which can produce natural light, have a high response speed and have no visibility angle dependency, and accordingly, there is an increasing interest on organic materials as their constituents. Among such organic materials, however, there are not many materials capable of forming stable red-light emitting layers in particular. Finding of such materials has, therefore, become an indispensable requirement for the realization of full-color, organic electroluminescent devices.

As light-sensitive materials for electrophotography, aminostyryl compounds are disclosed, for example, in Japanese Patent Laid-open No.: Hei 5-105645, 2001-051433, 2002-131943, 2002-116560, 2002-099103, 2002-072511, 2002-040677, 2002-040676, 2002-031901, 2001-337469, 2001-337649, and 2000-214610. However, these compounds contain no electron attracting group in their molecules and hence, cannot be used for such applications as red-color emitting materials for organic electroluminescent devices.

As materials for organic electroluminescent devices, certain compounds are disclosed in Japanese Patent Laid-open No. Hei 3-200889, Hei 5-194943, and 2002-226722. As illustrative materials employed in white-light organic electroluminescent devices, other materials are disclosed in Japanese Patent Laid-open No. Hei 6-207170. These materials are, however, not for the emission of red light either. Further, materials with one or more styryl groups contained in combination with one or more triphenylamino groups are proposed in Japanese Patent Laid-open No.: Hei 5-320632, Hei 6-100857, Hei 9-268284, Hei 11-040359, Hei 11-102784, and Hei 10-245549. These materials, however, cannot be used for the emission of red light either.

Aminostyryl compounds useful as red-light emitting materials in organic electroluminescent devices are led by the aminostyryl compounds disclosed in Inorganic and Organic Electroluminescence '96 Berlin, p. 101, 1996; Journal of the Korean Chemical Society (1999), 43(3), 315-320; Bulletin of the Korean Chemical Society (2001), 22(2), 228-230; and Journal of the Korean Chemical Society (1999), 43(3), 315-320, and include those disclosed in Japanese Patent Laid-open No.: 2000-230132, 2002-022672, 2001-2883772, 2001-106657, and 2001-106658. Further, their application examples are reported in Japanese Patent Laid-open No.: Hei 11-329730, Hei 11-329731, 2000-012225, 2000-012228, 2000-012227, 2000-012226, 2001-305754, and 2000-136168. As described in Japanese Patent Laid-open No. 2002-134276, 2001-291591, 2001-307884 and 2001-307885, two or more of these materials may be positively combined together for use.

As the molecular structures of the materials referred to in the above, many of them have structures symmetrical relative to the molecular long axes thereof. To obtain an emission maximum at an optimal wavelength or to permit the exhibition of improved evaporation upon fabrication of organic electroluminescent devices many of which are fabricated by vacuum evaporation, however, asymmetrical structures may be effective in certain instances as disclosed in Japanese Patent Laid-open NO.: 2002-226722, 2001-288377, 2001-110570 (especially, page 4, right column, line 40 to page 5, right column, line 4 from the bottom; page 7, right column, line 30 to page 8, left column, line 17; FIG. 1 to FIG. 8), 2001-110571 and 2000-173773.

Japanese Patent Laid-open No. 2002-208488, on the other hand, discloses that such asymmetrical structures are also effective as structural units for polymers. Further, their applications as multiphoton absorbers are also considered to be promising as disclosed in Science (1998), 281(11), 1653; WO 2001-096409; NATO Science Series, 3: High Technology (2000), 79 (Multiphoton and Light Driven Multielectron Processes in Organics), 53-65; Journal of Chemical Physics (2000), 113(10), 3951-3959; Journal of Physical Chemistry A (2001), 105(51), 11488-11495; Polymer Preprints (American Chemical Society, Division of Polymer Chemistry) (1998), 39(2), 1116; and Materials Research Society Symposium Proceedings (1998), 488 (Electrical, Optical, and Magnetic Properties of Organic Solid-State Materials IV), 217-226.

It is difficult to develop stable, high-luminance red-light emitting devices. Examples of those reported to date include a red-light emitting device making use of tris(8-hydroxyquinoline)aluminum (hereinafter abbreviated as "Alq$_3$") doped with 4-dicyanomethylene-6-(p-dimethylaminostyryl)-2-methyl-4H-pyran (hereinafter abbreviated as "DCM") (Chem. Funct. Dyes, Proc. Int. Symp., 2$^{nd}$, p. 536, 1993). As an example having achieved a reduction in the high crystallinity of DCM, there is 4-dicyanomethylene-6-(p-dimethylaminostyryl)-2-(t-butyl)-4H-pyran (hereinafter abbreviated as "DCJTB") disclosed in Macromol. Synmpt., 125, 49, 1997. However, their reliability such as service life is not satisfactory as display materials.

In the development of organic electroluminescent devices, selection of light emitting materials is the most important theme in assuring reliability for the devices. The aminostyrylnaphthalene compounds disclosed in Japanese Patent Laid-open NO. 2001-110570 are excellent in color purity and high in fluorescence quantum yield and moreover, can form stable, amorphous thin films. Nonetheless, it is the current situation that there is still an outstanding desire for the realization of a red-light emitting device of high luminance, high stability and high color purity.

SUMMARY OF THE INVENTION

Objects of the present invention are to provide an organic electroluminescent device capable of producing stable and high-luminance emission of red light at an optimal wavelength by using a compound improved in fluorescent wavelength over an aminostyrylnaphthalene compound which can produce emission of red light at a high fluorescence quantum yield, an aminostyrylnaphthalene compound useful in the organic electroluminescent device and its synthesis intermediates, and production processes of these compound and intermediates.

The present inventors have proceeded with an extensive investigation to achieve the above-described objects. As a result, it has been found that fabrication of an organic electroluminescent device with a luminescent layer, which makes use of a particular styryl compound in combination with a material capable of efficiently transmitting energy especially to the styryl compound, can provide a red-light emitting device of still higher luminance and reliability, leading to the present invention.

Described specifically, the present invention relates to an organic electroluminescent device including an anode, a cathode, and an organic layer arranged between the anode and said cathode, wherein at least a part of the organic layer includes at least one aminostyrylnaphthalene compound represented by the below-described formula [A]; and also to the aminostyrylnaphthalene compound:

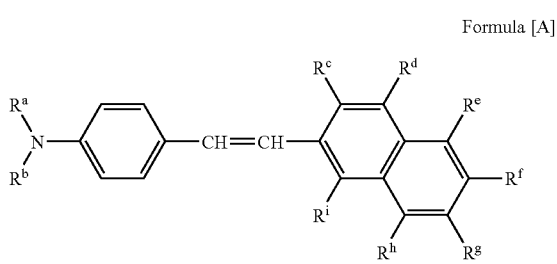

Formula [A]

wherein:

$R^a$ and $R^b$ may be the same or different and each independently represents a substituted or unsubstituted aryl group, $R^c$, $R^d$, $R^e$, $R^g$, $R^h$ and $R^i$ may be the same or different, at least one of $R^c$, $R^d$, $R^e$, $R^g$, $R^h$ and $R^i$ independently represents a hydrogen atom, a cyano group, a nitro group, a trifluoromethyl group or a halogen atom, and the remaining one or ones of $R^c$, $R^d$, $R^e$, $R^g$, $R^h$ and $R^i$, if any, are each a hydrogen atom, a cyano group, a nitro group, a trifluoromethyl group or a halogen atom, and $R^f$ represents a substituted or unsubstituted, saturated or unsaturated alkyl group, a substituted or unsubstituted alicyclic hydrocarbon group, a substituted or unsubstituted aryl group, a substituted or unsubstituted alkoxyl group, a substituted or unsubstituted alicyclic hydrocarbyloxy group or a substituted or unsubstituted aromatic hydrocarbyloxy group.

The aminostyrylnaphthalene compound, which is employed in the organic electroluminescent device according to the present invention and has the specific structure represented by the formula [A], owing to its specific structure, is excellent especially in the emission of red light, is equipped with electron transporting ability based on one or more electron attracting groups such as one or more cyano groups on a naphthalene group and also with hole transporting ability based on an aminostyryl group, and moreover, shows amorphous properties advantageous for film formability by vacuum deposition or the like and also durability especially for the inclusion of the substituent group $R^f$ (methyl, t-butyl or the like). Use of the aminostyrylnaphthalene compound, therefore, can provide an organic electroluminescent device capable of producing high-luminance and stable emission of red light at an optimal wavelength.

The above-described aminostyrylnaphthalene compound of the present invention can be effectively used as an organic light-emitting material capable of producing emission of red light of good chromaticy at a relatively-short, fluorescent wavelength. Further, owing to the inclusion of the substituent group $R^f$ (methyl, t-butyl or the like), it has a relatively small molecular weight and therefore, can reduce a thermal load to be applied upon vacuum evaporation or the like. Moreover, it is superb in electrical, thermal or chemical stability, and is amorphous and can readily form a glass state. Accordingly, it permits vacuum deposition or the like. With the organic electroluminescent device making use of the compound according to the present invention, red light the wavelength of which is relatively short is emitted. Therefore, the organic electroluminescent device is also advantageous in obtaining resonant light of improved color purity when the resonator structure disclosed in International publication No. WO 01/39554 is fabricated.

DETAILED DESCRIPTION OF THE PREFERRED EMBODIMENTS

Figure 1:
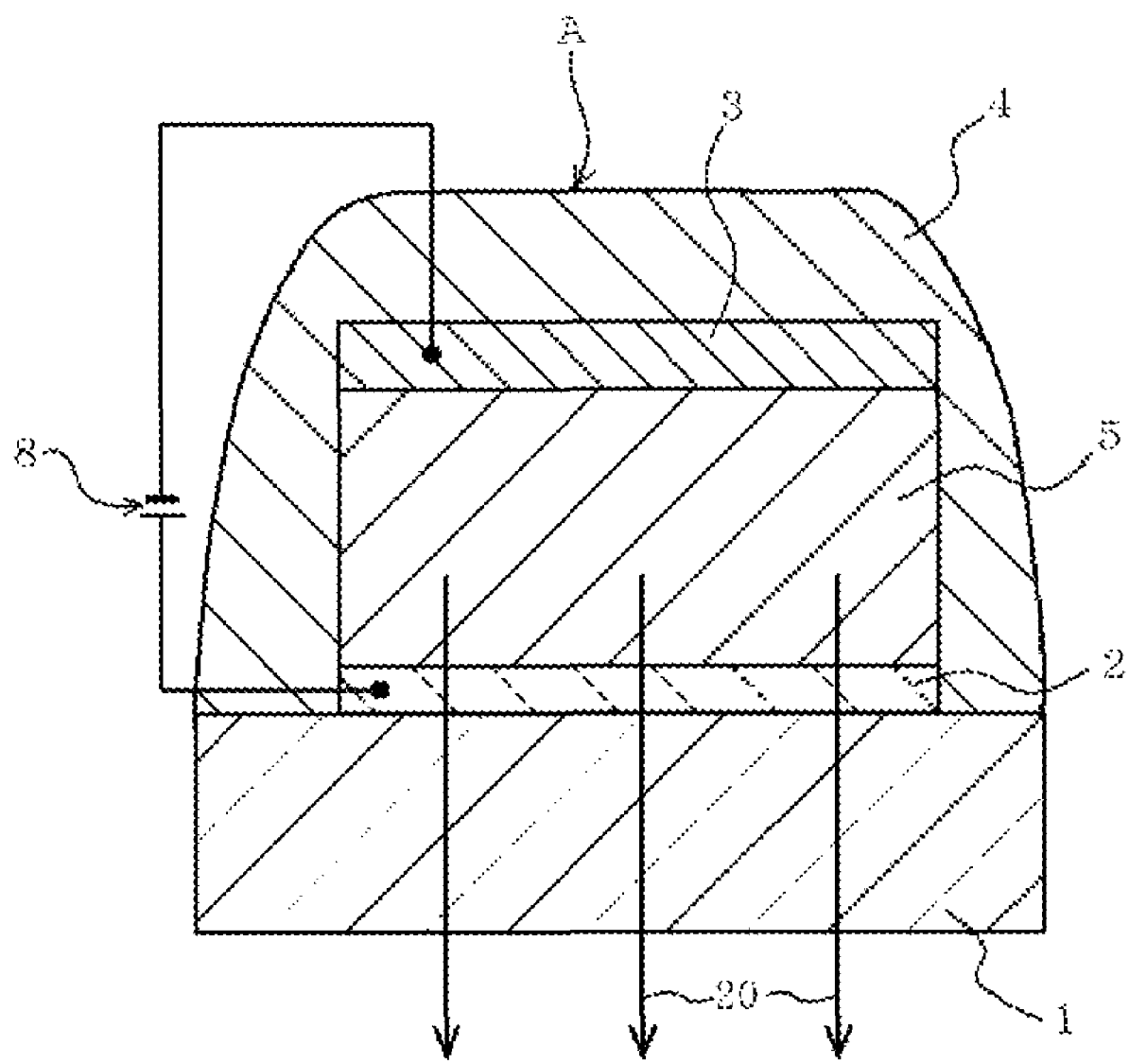
FIG. 1 is a schematic fragmentary cross-sectional view of an organic electroluminescent device according to an embodiment of the present invention.

The aminostyrylnaphthalene compound of the formula [A] according to the present invention may preferably comprise at least one aminostyrylnaphthalene compound represented by the following formula [I], [II] or [III]:

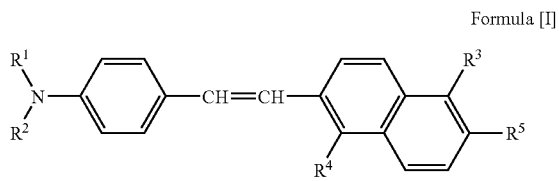

Formula [I]

wherein:

$R^1$ and $R^2$ may be the same or different and each independently represents a phenyl group represented by the following formula (1):

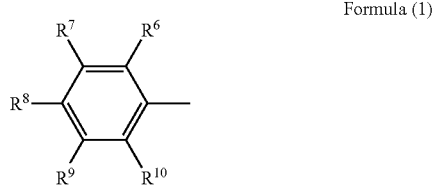

Formula (1)

wherein $R^6$, $R^7$, $R^8$, $R^9$ and $R^{10}$ may be the same or different, at least one of $R^6$ to $R^{10}$ represents a hydrogen atom, a saturated or unsaturated hydrocarbon group having at least one carbon atom with a proviso that, when at least two adjacent ones of $R^6$ to $R^{10}$ each represents a saturated or unsaturated hydrocarbon group having at least one carbon atom, at least the two adjacent ones of $R^6$ to $R^{10}$ may be fused together to form a ring, a saturated or unsaturated hydrocarbyloxy group having at least one carbon atom, a saturated or unsaturated hydrocarbylamino group having at least one carbon atom, a trifluoromethyl group, a cyano group or a halogen atom such as F, Cl or Br (the term "halogen atom" may hereinafter have a similar meaning), and the remaining one or ones of $R^6$ to $R^{10}$, if any, are each a hydrogen atom, a saturated or unsaturated hydrocarbon group having at least one carbon atom with a proviso that, when at least two adjacent ones of $R^6$ to $R^{10}$ each represents a saturated or unsaturated hydrocarbon group having at least one carbon atom, at least the two adjacent ones of $R^6$ to $R^{10}$ may be fused together to form a ring, a saturated or unsaturated hydrocarbyloxy group having at least one carbon atom, a saturated or unsaturated hydrocarbylamino group having at least one carbon atom, a trifluoromethyl group, a cyano group or a halogen atom, $R^3$ and $R^4$ may be the same or different, one of $R^3$ and $R^4$ represents a hydrogen atom, a cyano group, a nitro group, a trifluoromethyl group or a halogen atom, and the remaining one represents a hydrogen atom, a cyano group, a nitro group, a trifluoromethyl group or a halogen atom, and $R^5$ represents a substituted or unsubstituted, saturated or unsaturated alkyl group such as methyl, ethyl, n-propyl, i-propyl, n-butyl, i-butyl, t-butyl or allyl, a substituted or unsubstituted, alicyclic hydrocarbon group such as cyclohexyl, a substituted or unsubstituted aryl group such as phenyl, naphthyl or anthranyl, a substituted or unsubstituted alkoxyl group such as methoxy, ethoxy, n-propoxy, i-propoxy, n-butoxy, i-butoxy or t-butoxy, a substituted or unsubstituted, alicyclic hydrocarbyloxy group such as cyclohexyloxy, or a substituted or unsubstituted, aromatic hydrocarbyloxy group such as phenoxy, naphthoxy or anthroxy.

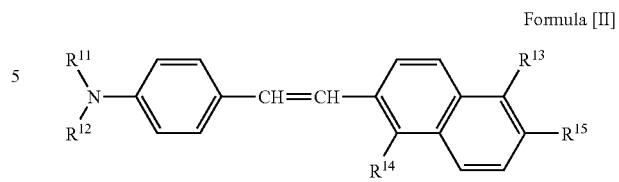

Formula [II]

wherein:

$R^{11}$ and $R^{12}$ may be the same or different and each independently represents a naphthyl group represented by the following formula (2):

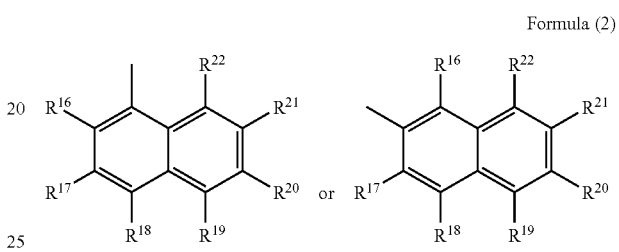

Formula (2)

wherein $R^{16}$, $R^{17}$, $R^{18}$, $R^{19}$, $R^{20}$, $R^{21}$ and $R^{22}$ may be the same or different, at least one of $R^{16}$ to $R^{22}$ represents a hydrogen atom, a saturated or unsaturated hydrocarbon group having at least one carbon atom, a saturated or unsaturated hydrocarbyloxy group having at least one carbon atom, a saturated or unsaturated hydrocarbylamino group having at least one carbon atom, a trifluoromethyl group, a cyano group or a halogen atom, and the remaining one or ones of $R^{16}$ to $R^{22}$, if any, are each a hydrogen atom, a saturated or unsaturated hydrocarbon group having at least one carbon atom, a saturated or unsaturated hydrocarbyloxy group having at least one carbon atom, a saturated or unsaturated hydrocarbylamino group having at least one carbon atom, a trifluoromethyl group, a cyano group or a halogen atom, $R^{13}$ and $R^{14}$ may be the same or different, one of $R^{13}$ and $R^{14}$ represents a hydrogen atom, a cyano group, a nitro group, a trifluoromethyl group or a halogen atom, and the remaining one represents a hydrogen atom, a cyano group, a nitro group, a trifluoromethyl group or a halogen atom, and $R^{15}$ represents a substituted or unsubstituted, saturated or unsaturated alkyl group such as methyl, ethyl, n-propyl, i-propyl, n-butyl, i-butyl, t-butyl or allyl, a substituted or unsubstituted, alicyclic hydrocarbon group such as cyclohexyl, a substituted or unsubstituted aryl group such as phenyl, naphthyl or anthranyl, a substituted or unsubstituted alkoxyl group such as methoxy, ethoxy, n-propoxy, i-propoxy, n-butoxy, i-butoxy or t-butoxy, a substituted or unsubstituted, alicyclic hydrocarbyloxy group such as cyclohexyloxy, or a substituted or unsubstituted, aromatic hydrocarbyloxy group such as phenoxy, naphthoxy or anthroxy.

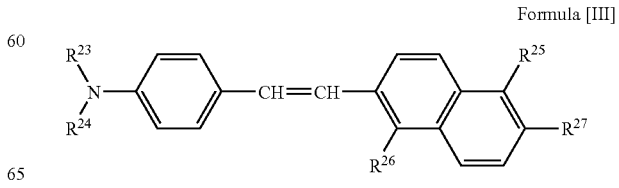

Formula [III]

wherein:

$R^{23}$ is a phenyl group represented by the following formula (3):

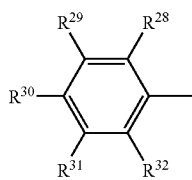

Formula (3)

wherein $R^{28}$, $R^{29}$, $R^{30}$, $R^{31}$ and $R^{32}$ may be the same or different, at least one of $R^{28}$ to $R^{32}$ represents a hydrogen atom, a saturated or unsaturated hydrocarbon group having at least one carbon atom with a proviso that, when at least two adjacent ones of $R^{28}$ to $R^{32}$ each represents a saturated or unsaturated hydrocarbon group having at least one carbon atom, at least the two adjacent ones of $R^{28}$ to $R^{32}$ may be fused together to form a ring, a hydrocarbyloxy group having at least one carbon atom, a hydrocarbylamino group having at least one carbon atom, a trifluoromethyl group, a cyano group or a halogen atom, and the remaining one or ones of $R^{28}$ to $R^{32}$, if any, are each a hydrogen atom, a saturated or unsaturated hydrocarbon group having at least one carbon atom with a proviso that, when at least two adjacent ones of $R^{28}$ to $R^{32}$ each represents a saturated or unsaturated hydrocarbon group having at least one carbon atom, at least the two adjacent ones of $R^{28}$ to $R^{32}$ may be fused together to form a ring, a saturated or unsaturated hydrocarbyloxy group having at least one carbon atom, a saturated or unsaturated hydrocarbylamino group having at least one carbon atom, a trifluoromethyl group, a cyano group or a halogen atom, $R^{24}$ represents a naphthyl group represented by the following formula (4):

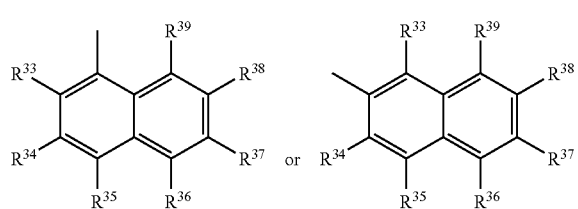

Formula (4)

wherein $R^{33}$, $R^{34}$, $R^{35}$, $R^{36}$, $R^{37}$, $R^{38}$ and $R^{39}$ may be the same or different, at least one of $R^{33}$ to $R^{39}$ represents a hydrogen atom, a saturated or unsaturated hydrocarbon group having at least one carbon atom, a saturated or unsaturated hydrocarbyloxy group having at least one carbon atom, a saturated or unsaturated hydrocarbylamino group having at least one carbon atom, a trifluoromethyl group, a cyano group or a halogen atom, and the remaining one or ones of $R^{33}$ to $R^{39}$, if any, are each a hydrogen atom, a saturated or unsaturated hydrocarbon group having at least one carbon atom, a saturated or unsaturated hydrocarbyloxy group having at least one carbon atom, a saturated or unsaturated hydrocarbylamino group having at least one carbon atom, a trifluoromethyl group, a cyano group or a halogen atom, $R^{25}$ and $R^{26}$ may be the same or different, one of $R^{25}$ and $R^{26}$ represents a hydrogen group, a cyano group, a nitro group, a trifluoromethyl group or a halogen atom, and the remaining one represents a hydrogen group, a cyano group, a nitro group, a trifluoromethyl group or a halogen atom, and $R^{27}$ represents a substituted or unsubstituted, saturated or unsaturated alkyl group such as methyl, ethyl, n-propyl, i-propyl, n-butyl, i-butyl, t-butyl or ally, a substituted or unsubstituted, alicyclic hydrocarbon group such as cyclohexyl, a substituted or unsubstituted aryl group such as phenyl, naphthyl or anthranyl, a substituted or unsubstituted alkoxyl group such as methoxy, ethoxy, n-propoxy, i-propoxy, n-butoxy, i-butoxy or t-butoxy, a substituted or unsubstituted, alicyclic hydrocarbyloxy group such as cyclohexyloxy, or a substituted or unsubstituted, aromatic hydrocarbyloxy group such as phenoxy, naphthoxy or anthroxy.

The aminostyrylnaphthalene compound, which has the specific structure represented by the formula [I], [II] or [III], owing to its specific structure, is excellent especially in the emission of red light, is equipped with electron transporting ability based on one or more electron attracting groups such as one or more cyano groups on a naphthalene group and also with hole transporting ability based on an aminostyryl group, and moreover, shows amorphous properties advantageous for film formability by vacuum deposition or the like and also durability. Use of the aminostyrylnaphthalene compound, therefore, can provide an organic electroluminescent device capable of producing especially high-luminance and stable emission of red light at an optimal wavelength.

In the organic electroluminescent device according to the present invention, it is preferred that the organic layer is in a form of an organic multilayer structure comprising a hole transport layer and an electron transport layer stacked one over the other, and also that at least the electron transport layer in the organic layer comprises at least the one aminostyrylnaphthalene compound represented by the formula [A], especially the formula [I], [II] or [III].

Preferably, the organic layer is in a form of an organic multilayer structure comprising a hole transport layer and an electron transport layer stacked one over the other, and at least the hole transport layer in the organic layer comprises at least the one aminostyrylnaphthalene compound represented by the formula [A], especially the formula [I], [II] or [III].

Preferably, the organic layer is in a form of an organic multilayer structure comprising a hole transport layer, a luminescent layer and an electron transport layer stacked one over another, and at least the luminescent layer in the organic layer comprises at least the one aminostyrylnaphthalene compound represented by the formula [A], especially the formula [I], [II] or [III].

Further, the aminostyrylnaphthalene compound may preferably be represented by the following formula (5), (6), (7), (8), (9), (10), (11), (12), (13), (14), (15), (16) or (17):

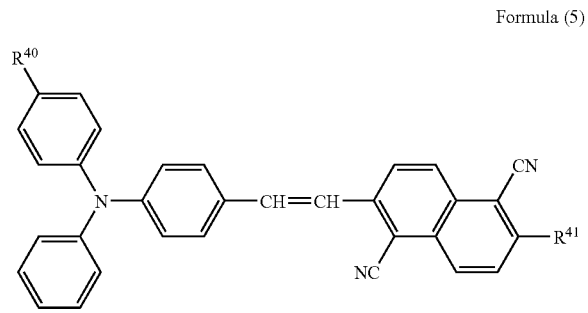

Formula (5)

wherein $R^{40}$ represents a saturated or unsaturated alkyl group having 1 to 6 carbon atoms or a substituted or unsubstituted aryl group, and $R^{41}$ has the same meaning as $R^5$.

Formula (6)

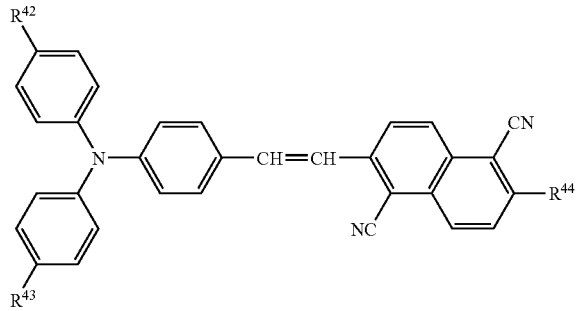

wherein $R^{42}$ and $R^{43}$ may be the same or different, one of $R^{42}$ and $R^{43}$ represents a saturated or unsaturated alkyl group having 1 to 6 carbon atoms or a substituted or unsubstituted aryl group, the remaining one of $R^{42}$ and $R^{43}$ represents a saturated or unsaturated alkyl group having 1 to 6 carbon atoms or a substituted or unsubstituted aryl group, and $R^{44}$ has the same meaning as $R^5$.

Formula (7)

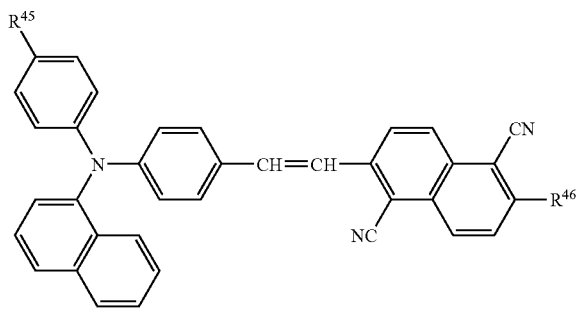

wherein $R^{45}$ represents a saturated or unsaturated alkyl group having 1 to 6 carbon atoms or a substituted or unsubstituted aryl group, and $R^{46}$ has the same meaning as $R^{27}$.

Formula (8)

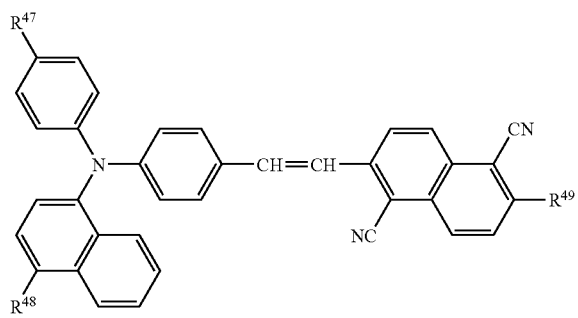

wherein $R^{47}$ and $R^{48}$ may be the same or different and each independently represents a saturated or unsaturated alkyl group having 1 to 6 carbon atoms or a substituted or unsubstituted aryl group, and $R^{49}$ has the same meaning as $R^{27}$.

Formula (9)

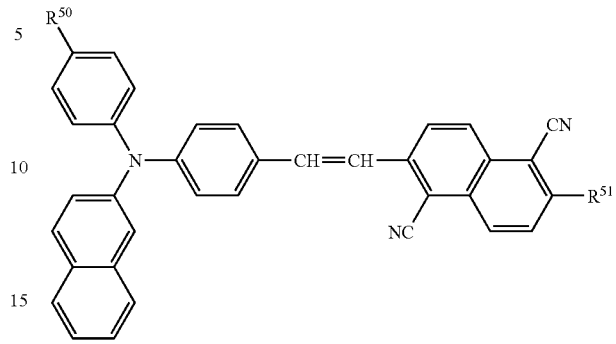

wherein $R^{50}$ represents a saturated or unsaturated alkyl group having 1 to 6 carbon atoms or a substituted or unsubstituted aryl group, and $R^{51}$ has the same meaning as $R^{27}$.

Formula (10)

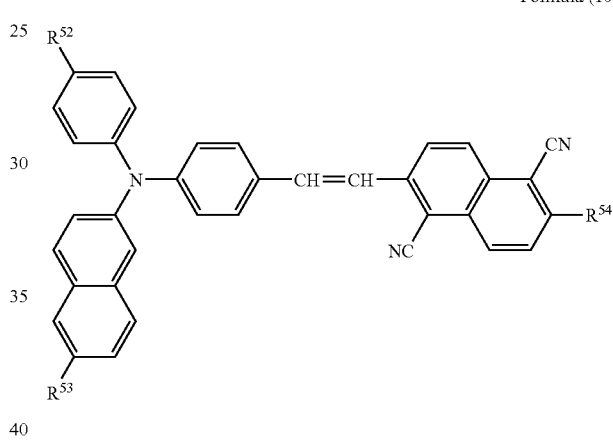

wherein $R^{52}$ and $R^{53}$ may be the same or different, one of $R^{52}$ and $R^{53}$ represents a saturated or unsaturated alkyl group having 1 to 6 carbon atoms or a substituted or unsubstituted aryl group, the remaining one of $R^{52}$ and $R^{53}$ represents a saturated or unsaturated alkyl group having 1 to 6 carbon atoms or a substituted or unsubstituted aryl group, and $R^{54}$ has the same meaning as $R^{27}$.

Formula (11)

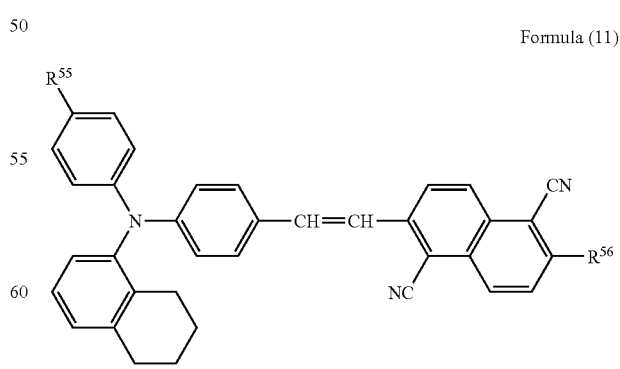

wherein $R^{55}$ represents a saturated or unsaturated alkyl group having 1 to 6 carbon atoms or a substituted or unsubstituted aryl group, and $R^{56}$ has the same meaning as $R^5$.

Formula (12)

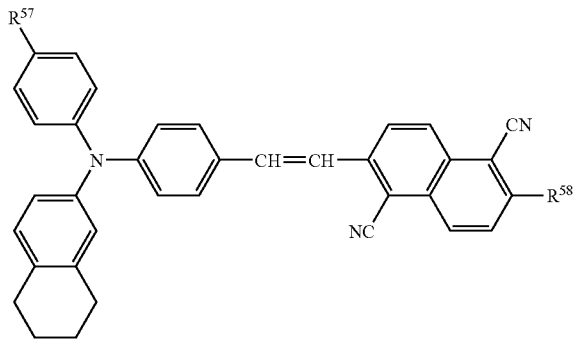

wherein $R^{57}$ represents a saturated or unsaturated alkyl group having 1 to 6 carbon atoms or a substituted or unsubstituted aryl group, and $R^{58}$ has the same meaning as $R^5$.

Formula (13)

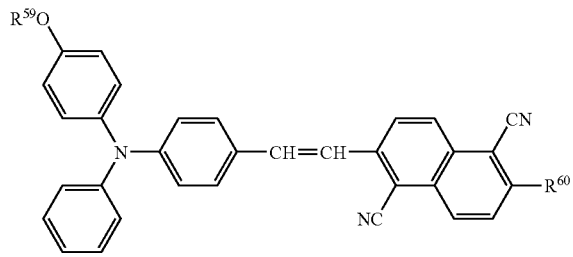

wherein $R^{59}$ represents a saturated or unsaturated alkyl group having 1 to 6 carbon atoms or a substituted or unsubstituted aryl group, and $R^{60}$ has the same meaning as $R^5$.

Formula (14)

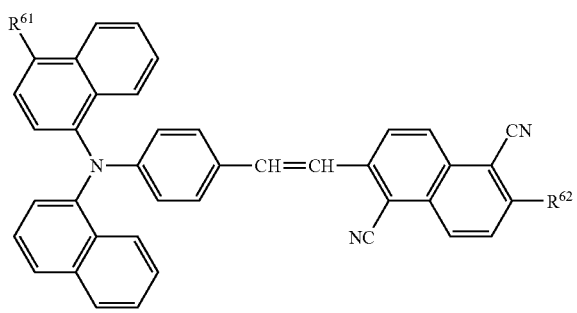

wherein $R^{61}$ represents a saturated or unsaturated alkyl group having 1 to 6 carbon atoms or a substituted or unsubstituted aryl group, and $R^{62}$ has the same meaning as $R^{15}$.

Formula (15)

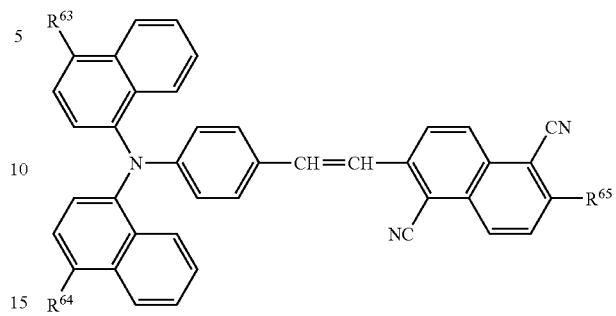

wherein $R^{63}$ and $R^{64}$ may be the same or different, one of $R^{63}$ and $R^{64}$ represents a saturated or unsaturated alkyl group having 1 to 6 carbon atoms or a substituted or unsubstituted aryl group, the remaining one of $R^{63}$ and $R^{64}$ represents a saturated or unsaturated alkyl group having 1 to 6 carbon atoms or a substituted or unsubstituted aryl group, and $R^{65}$ has the same meaning as $R^{15}$.

Formula (16)

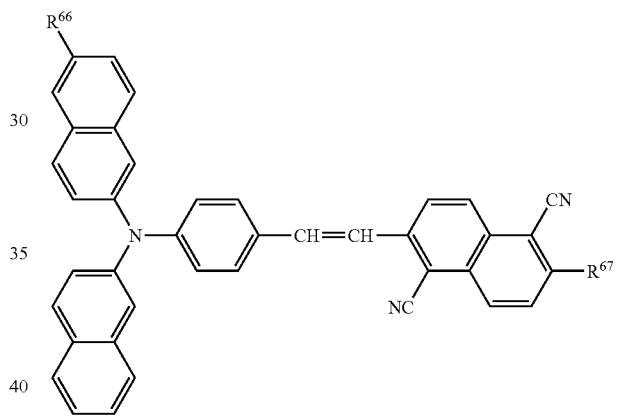

wherein $R^{66}$ represents a saturated or unsaturated alkyl group having 1 to 6 carbon atoms or a substituted or unsubstituted aryl group, and $R^{67}$ has the same meaning as $R^{15}$.

Formula (17)

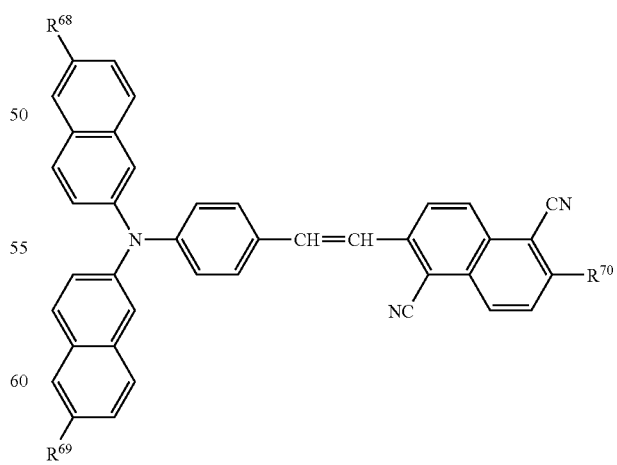

wherein $R^{68}$ and $R^{69}$ may be the same or different, one of $R^{68}$ and $R^{69}$ represents a saturated or unsaturated alkyl group having 1 to 6 carbon atoms or a substituted or unsubstituted aryl group, the remaining one of $R^{68}$ and $R^{69}$ represents a saturated or unsaturated alkyl group having 1 to 6 carbon atoms or a substituted or unsubstituted aryl group, and $R^{70}$ has the same meaning as $R^{15}$.

The present invention also provides an aminostyrylnaphthalene compound represented by the above-described formula [A], especially the above-described formula [I], [II] or [III].

The above-described aminostyrylnaphthalene compound of the present invention can be effectively used as an organic light-emitting material capable of producing emission of red light of good chromaticy at a relatively-short, fluorescent wavelength. Further, owing to the inclusion of the substituent group $R^f$ (especially, $R^5$, $R^{15}$ or $R^{27}$), it has a relatively small molecular weight and therefore, can reduce a thermal load to be applied upon vacuum evaporation or the like. Moreover, it is superb in electrical, thermal or chemical stability, and is amorphous and can readily form a glass state. Accordingly, it permits vacuum deposition or the like. With the organic electroluminescent device making use of the compound according to the present invention, red light the wavelength of which is relatively short can be emitted. Therefore, the organic electroluminescent device is also advantageous in obtaining resonant light of improved color purity when the resonator structure disclosed in WO 01/39554 is fabricated. These advantageous features can be brought about especially when the groups $R^c$, $R^d$, $R^e$, $R^g$, $R^h$ and $R^i$ are electron-attracting groups such as cyano groups. However, these groups may all be hydrogen atoms although emission of light other than red light, for example, emission of green light is obtained in such a case.

The compound according to the present invention may preferably be represented by any one of the above-described formulas (5) to (17).

Representing the preferred compound by the following formula [I'], the preferred compound can be exemplified as will be presented below in Table 1 to Table 24.

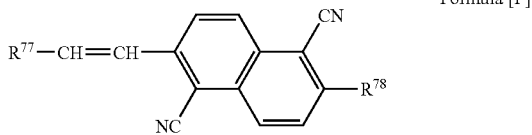

Formula [I']

wherein $R^{77}$ and $R^{78}$ are as will be specified in the following tables which show diverse combinations of $R^{77}$ and $R^{78}$.

TABLE 1

| | | $R^{78}$ | | | | | |
|---|---|---|---|---|---|---|---|
| $R^{77}$ | —CH₃ | —C₂H₅ | —n-C₃H₇ | —i-C₃H₇ | —n-C₄H₉ | —i-C₄H₉ | —t-C₄H₉ |
| (diphenylamino-p-tolyl) | (20)-1 | (20)-19 | (20)-37 | (20)-55 | (20)-73 | (20)-91 | (20)-109 |
| (4-methylphenyl)(phenyl)amino-p-tolyl | (20)-2 | (20)-20 | (20)-38 | (20)-56 | (20)-74 | (20)-92 | (20)-110 |
| bis(4-methylphenyl)amino-p-tolyl | (20)-3 | (20)-21 | (20)-39 | (20)-57 | (20)-75 | (20)-93 | (20)-111 |

TABLE 1-continued

| R⁷⁷ | R⁷⁸ | | | | | | |
|---|---|---|---|---|---|---|---|
| | —CH₃ | —C₂H₅ | —n-C₃H₇ | —i-C₃H₇ | —n-C₄H₉ | —i-C₄H₉ | —t-C₄H₉ |
| *N-phenyl-N-(p-tolyl)naphthalen-1-amine* | (20)-4 | (20)-22 | (20)-40 | (20)-58 | (20)-76 | (20)-94 | (20)-112 |
| *N-(naphthalen-1-yl)-N-(p-tolyl)naphthalen-1-amine* | (20)-5 | (20)-23 | (20)-41 | (20)-59 | (20)-77 | (20)-95 | (20)-113 |
| *N,N-di(p-tolyl)naphthalen-1-amine* | (20)-6 | (20)-24 | (20)-42 | (20)-60 | (20)-78 | (20)-96 | (20)-114 |
| *N-phenyl-N-(p-tolyl)-4-methylnaphthalen-1-amine* | (20)-7 | (20)-25 | (20)-43 | (20)-61 | (20)-79 | (20)-97 | (20)-115 |
| *N,N-di(p-tolyl)-4-methylnaphthalen-1-amine* | (20)-8 | (20)-26 | (20)-44 | (20)-62 | (20)-80 | (20)-98 | (20)-116 |

TABLE 2
| $R^{77}$ | $R^{78}$ | | | | | | |
|---|---|---|---|---|---|---|---|
| | —CH$_3$ | —C$_2$H$_5$ | —n-C$_3$H$_7$ | —i-C$_3$H$_7$ | —n-C$_4$H$_9$ | —i-C$_4$H$_9$ | —t-C$_4$H$_9$ |
| 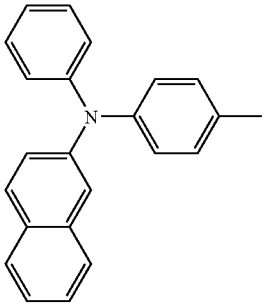 | (20)-9 | (20)-27 | (20)-45 | (20)-63 | (20)-81 | (20)-99 | (20)-117 |
| 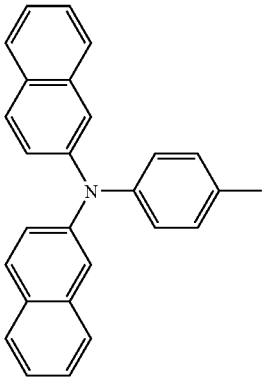 | (20)-10 | (20)-28 | (20)-46 | (20)-64 | (20)-82 | (20)-100 | (20)-118 |
| 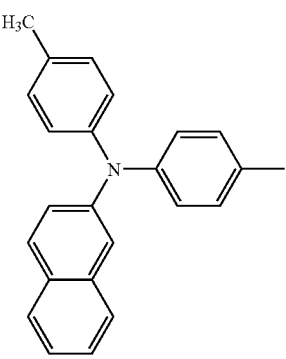 | (20)-11 | (20)-29 | (20)-47 | (20)-65 | (20)-83 | (20)-101 | (20)-119 |
| 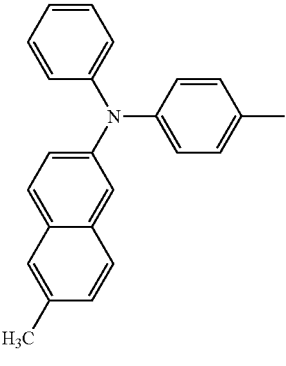 | (20)-12 | (20)-30 | (20)-48 | (20)-66 | (20)-84 | (20)-102 | (20)-120 |

TABLE 2-continued
| $R^{77}$ | $R^{78}$ | | | | | | |
|---|---|---|---|---|---|---|---|
| | —CH₃ | —C₂H₅ | —n-C₃H₇ | —i-C₃H₇ | —n-C₄H₉ | —i-C₄H₉ | —t-C₄H₉ |
| 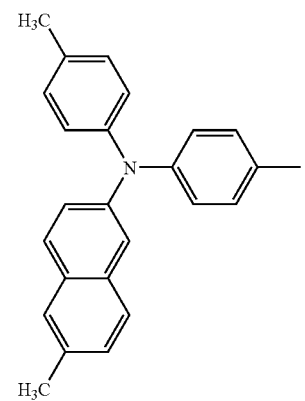 | (20)-13 | (20)-31 | (20)-49 | (20)-67 | (20)-85 | (20)-103 | (20)-121 |
| 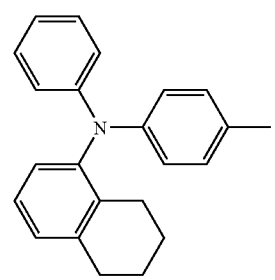 | (20)-14 | (20)-32 | (20)-50 | (20)-68 | (20)-86 | (20)-104 | (20)-122 |
| 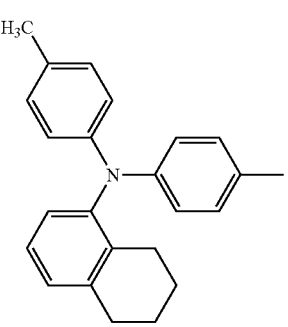 | (20)-15 | (20)-33 | (20)-51 | (20)-69 | (20)-87 | (20)-105 | (20)-123 |
TABLE 3
| $R^{77}$ | $R^{78}$ | | | | | | |
|---|---|---|---|---|---|---|---|
| | —CH₃ | —C₂H₅ | —n-C₃H₇ | —i-C₃H₇ | —n-C₄H₉ | —i-C₄H₉ | —t-C₄H₉ |
| 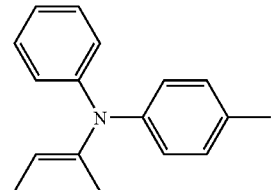 | (20)-16 | (20)-34 | (20)-52 | (20)-70 | (20)-88 | (20)-106 | (20)-124 |

TABLE 3-continued

| R⁷⁷ | R⁷⁸ | | | | | | |
|---|---|---|---|---|---|---|---|
| | —CH₃ | —C₂H₅ | —n-C₃H₇ | —i-C₃H₇ | —n-C₄H₉ | —i-C₄H₉ | —t-C₄H₉ |
| H₃CO–C₆H₄–N(C₆H₅)(p-CH₃-C₆H₄) | (20)-17 | (20)-35 | (20)-53 | (20)-71 | (20)-89 | (20)-107 | (20)-125 |
| (H₃CO–C₆H₄)₂N(p-CH₃-C₆H₄) | (20)-18 | (20)-36 | (20)-54 | (20)-72 | (20)-90 | (20)-108 | (20)-126 |

TABLE 4

| R77 | R78 | | | | | | | |
|---|---|---|---|---|---|---|---|---|
| | –OCF₃ (para) | –O–/CF₃ (meta) | cyclohexyl-CH₃ | biphenyl | phenyl-CH₃ (para) | phenyl-CH₃ (meta) | phenyl-C₂H₅ | phenyl-n-C₃H₇ |
| N(C₆H₄-CH₃)(C₆H₅)(C₆H₅) | (21)-1 | (21)-19 | (21)-37 | (21)-55 | (21)-73 | (21)-91 | (21)-109 | (21)-127 |
| N(C₆H₄-CH₃)(C₆H₄-CH₃)(C₆H₅) | (21)-2 | (21)-20 | (21)-38 | (21)-56 | (21)-74 | (21)-92 | (21)-110 | (21)-128 |
| N(C₆H₄-CH₃)₃ | (21)-3 | (21)-21 | (21)-39 | (21)-57 | (21)-75 | (21)-93 | (21)-111 | (21)-129 |

TABLE 4-continued
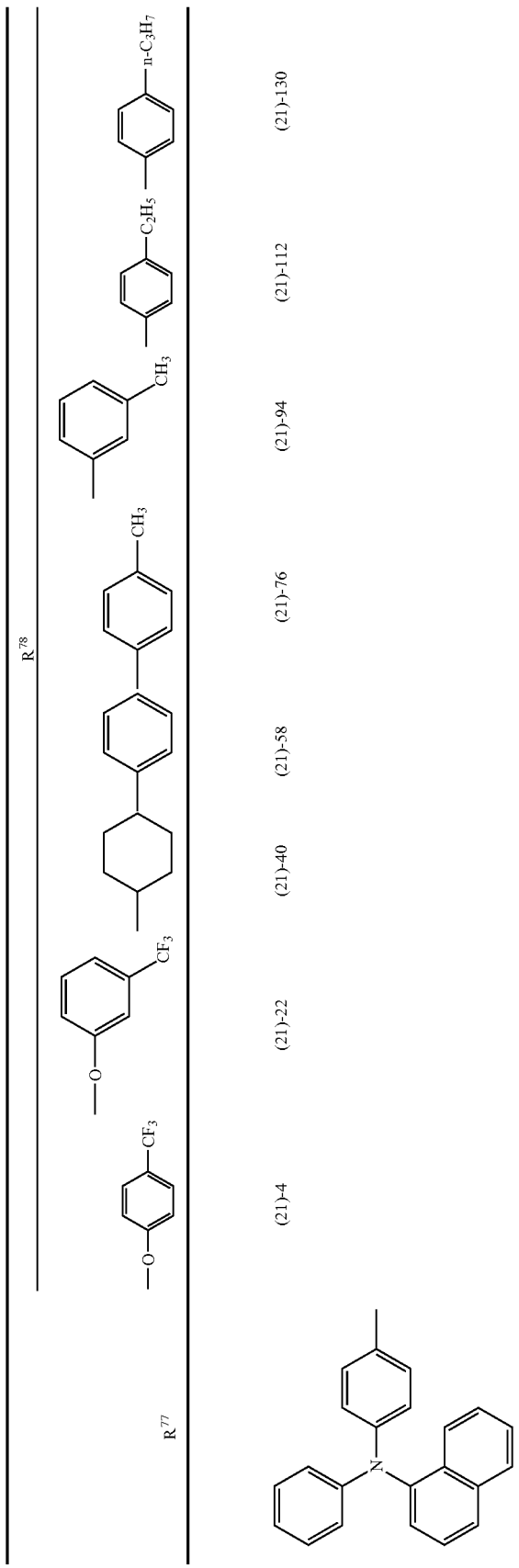
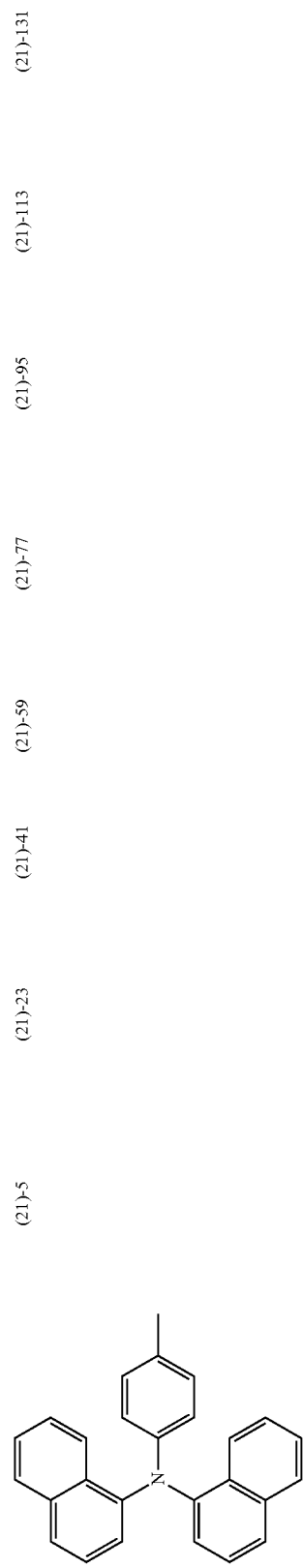

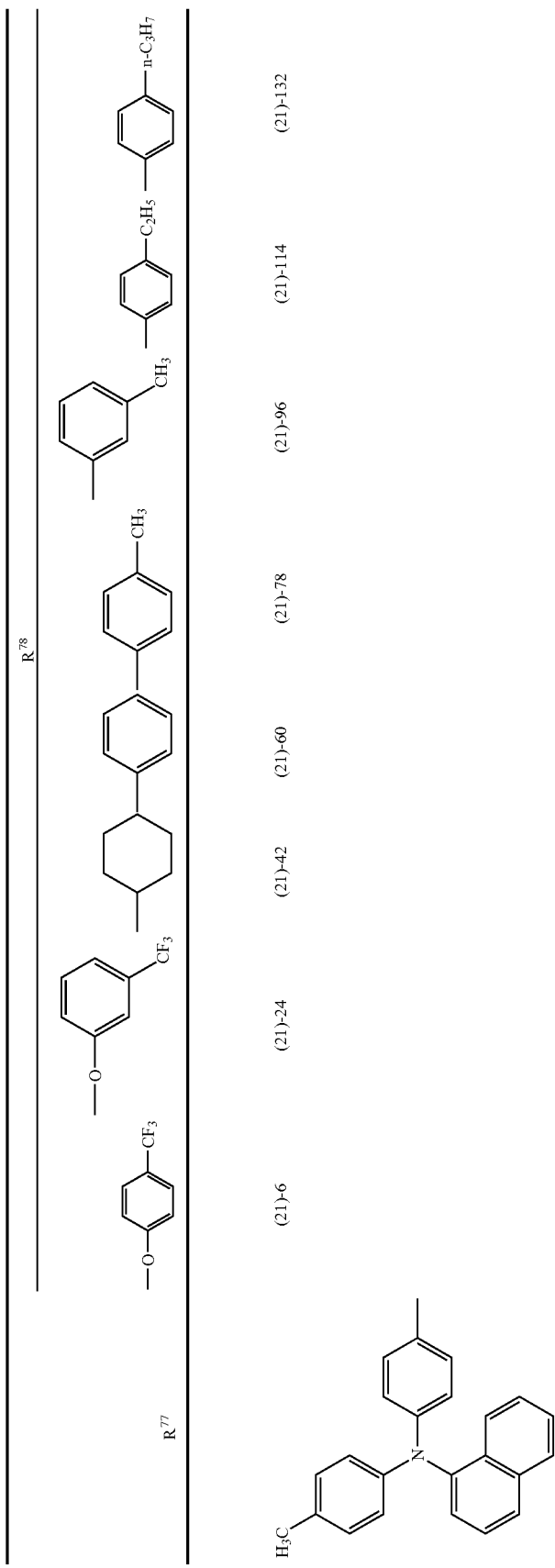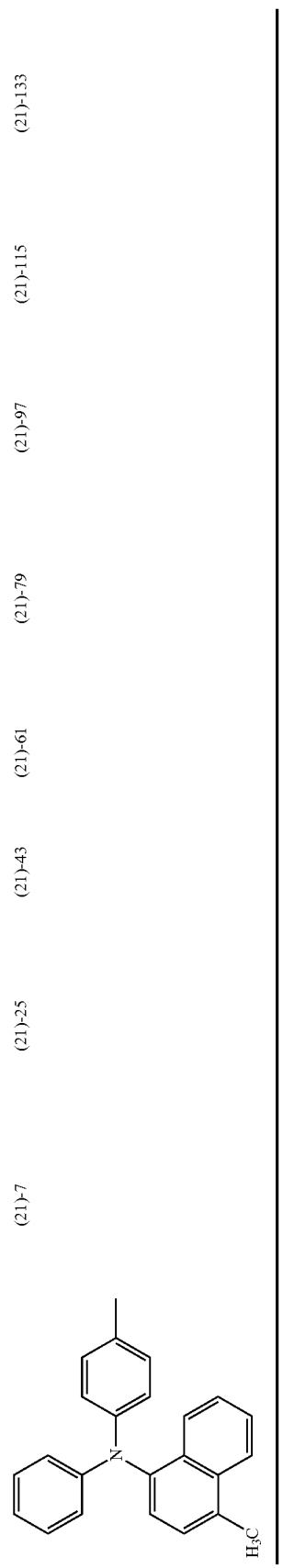

TABLE 5

| R⁷⁷ | R⁷⁸ | | | | | | | |
|---|---|---|---|---|---|---|---|---|
| | —O-C₆H₄-CF₃ | —O-C₆H₄(m)-CF₃ | cyclohexyl-CH₃ | biphenyl-CH₃ | C₆H₄(m)-CH₃ | C₆H₄-C₂H₅ | C₆H₄-n-C₃H₇ |
| (di-p-tolyl)(4-methylnaphth-1-yl)amine | (21)-8 | (21)-26 | (21)-44 | (21)-62 | (21)-80 | (21)-98 | (21)-116 | (21)-134 |
| (phenyl)(p-tolyl)(naphth-2-yl)amine | (21)-9 | (21)-27 | (21)-45 | (21)-63 | (21)-81 | (21)-99 | (21)-117 | (21)-135 |

TABLE 5-continued

TABLE 5-continued
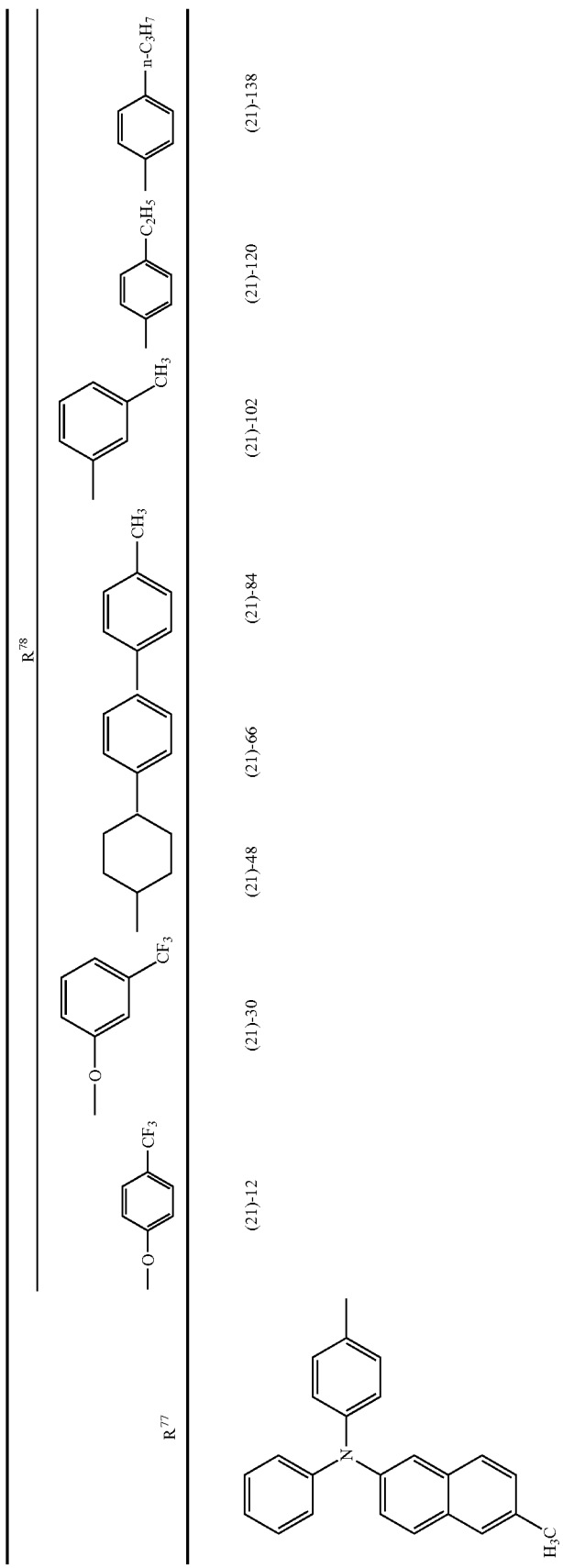

TABLE 5-continued

| R<sup>77</sup> | R<sup>78</sup> | |

TABLE 6

TABLE 6-continued

| R⁷⁷ | R⁷⁸ | | | | | | | |
|---|---|---|---|---|---|---|---|---|
| | —O—⌬—CF₃ | —O—⌬(CF₃)— | —⌬(cyclohexyl-CH₃)— | —⌬—⌬—CH₃ | —⌬(m-CH₃)— | —⌬—C₂H₅ | —⌬—n-C₃H₇ |
| (H₃CO-C₆H₄)(p-tolyl)(C₆H₅)N– | (21)-17 | (21)-35 | (21)-53 | (21)-71 | (21)-89 | (21)-107 | (21)-125 | (21)-143 |
| (H₃CO-C₆H₄)₂(p-tolyl)N– | (21)-18 | (21)-36 | (21)-54 | (21)-72 | (21)-90 | (21)-108 | (21)-126 | (21)-144 |

TABLE 7

| R$^{77}$ | R$^{78}$ | | | | | | |
|---|---|---|---|---|---|---|---|
| | i-C$_3$H$_7$-C$_6$H$_4$- | n-C$_4$H$_9$-C$_6$H$_4$- | i-C$_4$H$_9$-C$_6$H$_4$- | t-C$_4$H$_9$-C$_6$H$_4$- | 4-CF$_3$-C$_6$H$_4$- | 3-CF$_3$-C$_6$H$_4$- | 1-naphthyl | 4-methyl-1-naphthyl |
| (p-tolyl)(phenyl)(phenyl)I | (22)-1 | (22)-19 | (22)-37 | (22)-55 | (22)-73 | (22)-91 | (22)-109 | (22)-127 |
| (p-tolyl)(p-tolyl)(phenyl)I | (22)-2 | (22)-20 | (22)-38 | (22)-56 | (22)-74 | (22)-92 | (22)-110 | (22)-128 |
| (p-tolyl)(p-tolyl)(p-tolyl)I | (22)-3 | (22)-21 | (22)-39 | (22)-57 | (22)-75 | (22)-93 | (22)-111 | (22)-129 |

TABLE 7-continued

| R<sup>77</sup> | R<sup>78</sup> | | | | | | | | |
|---|---|---|---|---|---|---|---|---|---|
| | i-C₃H₇-phenyl | n-C₄H₉-phenyl | i-C₄H₉-phenyl | t-C₄H₉-phenyl | CF₃-phenyl | m-CH₃-C₆H₄-CF₃ | 4-methylnaphthyl | 1-methylnaphthyl (at 4-position) | |
| N(phenyl)(p-tolyl)(1-naphthyl) | (22)-4 | (22)-22 | (22)-40 | (22)-58 | (22)-76 | (22)-94 | (22)-112 | (22)-130 | |
| N(p-tolyl)(1-naphthyl)(1-naphthyl) | (22)-5 | (22)-23 | (22)-41 | (22)-59 | (22)-77 | (22)-95 | (22)-113 | (22)-131 | |

TABLE 7-continued

| R<sup>77</sup> | R<sup>78</sup> | |
|---|---|---|
| ![tolyl-naphthyl-tolyl amine] | 4-(i-C₃H₇)-C₆H₄- | (22)-6 |
| | 4-(n-C₄H₉)-C₆H₄- | (22)-24 |
| | 4-(i-C₄H₉)-C₆H₄- | (22)-42 |
| | 4-(t-C₄H₉)-C₆H₄- | (22)-60 |
| | 4-(CF₃)-C₆H₄- | (22)-78 |
| | 3-(CF₃)-C₆H₄- | (22)-96 |
| | 4-methylnaphthyl | (22)-114 |
| | 1-methylnaphthyl | (22)-132 |
| ![tolyl-naphthyl-phenyl amine] | 4-(i-C₃H₇)-C₆H₄- | (22)-7 |
| | 4-(n-C₄H₉)-C₆H₄- | (22)-25 |
| | 4-(i-C₄H₉)-C₆H₄- | (22)-43 |
| | 4-(t-C₄H₉)-C₆H₄- | (22)-61 |
| | 4-(CF₃)-C₆H₄- | (22)-79 |
| | 3-(CF₃)-C₆H₄- | (22)-97 |
| | 4-methylnaphthyl | (22)-115 |
| | 1-methylnaphthyl | (22)-133 |

TABLE 8

| $R^{77}$ | $R^{78}$ | | | | | | | |
|---|---|---|---|---|---|---|---|---|
| | 4-(i-C₃H₇)-C₆H₄ | 4-(n-C₄H₉)-C₆H₄ | 4-(i-C₄H₉)-C₆H₄ | 4-(t-C₄H₉)-C₆H₄ | 4-(CF₃)-C₆H₄ | 3-(CF₃)-C₆H₄ | 4-CH₃-naphth-1-yl | 1-CH₃-naphth-4-yl |
| N(4-CH₃-C₆H₄)₂(4-CH₃-naphth-1-yl) | (22)-8 | (22)-26 | (22)-44 | (22)-62 | (22)-80 | (22)-98 | (22)-116 | (22)-134 |
| N(4-CH₃-C₆H₄)(C₆H₅)(naphth-2-yl) | (22)-9 | (22)-27 | (22)-45 | (22)-63 | (22)-81 | (22)-99 | (22)-117 | (22)-135 |

TABLE 8-continued

| $R^{77}$ | $R^{78}$ | | | | | | | | |
|---|---|---|---|---|---|---|---|---|---|
| | 4-i-C₃H₇-C₆H₄ | 4-n-C₄H₉-C₆H₄ | 4-i-C₄H₉-C₆H₄ | 4-t-C₄H₉-C₆H₄ | 4-CF₃-C₆H₄ | 3-CF₃-C₆H₄ | 4-Me-1-naphthyl | 1-Me-4-naphthyl | |
| di(2-naphthyl)(4-methylphenyl) | (22)-10 | (22)-28 | (22)-46 | (22)-64 | (22)-82 | (22)-100 | (22)-118 | (22)-136 | |
| (2-naphthyl)bis(4-methylphenyl) | (22)-11 | (22)-29 | (22)-47 | (22)-65 | (22)-83 | (22)-101 | (22)-119 | (22)-137 | |

TABLE 8-continued

| $R^{77}$ | $R^{78}$ | | | | | | | | |
|---|---|---|---|---|---|---|---|---|---|
| | 4-(i-C$_3$H$_7$)-C$_6$H$_4$- | 4-(n-C$_4$H$_9$)-C$_6$H$_4$- | 4-(i-C$_4$H$_9$)-C$_6$H$_4$- | 4-(t-C$_4$H$_9$)-C$_6$H$_4$- | 4-(CF$_3$)-C$_6$H$_4$- | 3-(CF$_3$)-C$_6$H$_4$- | 4-CH$_3$-naphthyl | 4-CH$_3$-naphthyl | |
| N(phenyl)(4-methylphenyl)-6-methyl-2-naphthyl | (22)-12 | (22)-30 | (22)-48 | (22)-66 | (22)-84 | (22)-102 | (22)-120 | (22)-138 | |
| N(4-methylphenyl)(4-methylphenyl)-6-methyl-2-naphthyl | (22)-13 | (22)-31 | (22)-49 | (22)-67 | (22)-85 | (22)-103 | (22)-121 | (22)-139 | |

TABLE 8-continued

| | $R^{77}$ | $R^{78}$ |
|---|---|---|
| (22)-14 | 4-(i-C$_3$H$_7$)phenyl | |
| (22)-32 | 4-(n-C$_4$H$_9$)phenyl | |
| (22)-50 | 4-(i-C$_4$H$_9$)phenyl | |
| (22)-68 | 4-(i-C$_4$H$_9$)phenyl | |
| (22)-86 | 4-(t-C$_4$H$_9$)phenyl | |
| (22)-104 | 4-(CF$_3$)phenyl | |
| (22)-122 | 3-(CF$_3$)phenyl | |
| (22)-140 | 4-methylnaphthyl | |

(Structure of R$^{77}$: N(phenyl)(4-methylphenyl) attached to tetrahydronaphthyl)

TABLE 9

| $R^{77}$ | $R^{78}$ | | | | | | | | |
|---|---|---|---|---|---|---|---|---|---|
| | 4-(i-C₃H₇)-C₆H₄ | 4-(n-C₄H₉)-C₆H₄ | 4-(i-C₄H₉)-C₆H₄ | 4-(t-C₄H₉)-C₆H₄ | 4-CF₃-C₆H₄ | 3-CF₃-C₆H₄ | 4-CH₃-naphthyl | 4-CH₃-naphthyl(other) | |
| N(4-CH₃-C₆H₄)(5,6,7,8-tetrahydronaphthalen-1-yl) | (22)-15 | (22)-33 | (22)-51 | (22)-69 | (22)-87 | (22)-105 | (22)-123 | (22)-141 | |
| N(C₆H₅)(4-CH₃-C₆H₄)(5,6,7,8-tetrahydronaphthalen-2-yl) | (22)-16 | (22)-34 | (22)-52 | (22)-70 | (22)-88 | (22)-106 | (22)-124 | (22)-142 | |

TABLE 9-continued

| R⁷⁷ | R⁷⁸ | | | | | | |
|---|---|---|---|---|---|---|---|
| | i-C₃H₇-C₆H₄- | n-C₄H₉-C₆H₄- | i-C₄H₉-C₆H₄- | t-C₄H₉-C₆H₄- | 4-CF₃-C₆H₄- | 3-CF₃-C₆H₄- | 1-methylnaphthyl | 4-methylnaphthyl |
| (4-CH₃O-C₆H₄)(4-CH₃-C₆H₄)(C₆H₅)I | (22)-17 | (22)-35 | (22)-53 | (22)-71 | (22)-89 | (22)-107 | (22)-125 | (22)-143 |
| (4-CH₃O-C₆H₄)₂(4-CH₃-C₆H₄)I | (22)-18 | (22)-36 | (22)-54 | (22)-72 | (22)-90 | (22)-108 | (22)-126 | (22)-144 |

TABLE 10

| R77 | R78: naphthyl | methylnaphthyl | methyl-tetrahydronaphthyl | tetrahydronaphthyl | —OCH₃ | —OC₂H₅ | —O(n-C₃H₇) | —O(i-C₃H₇) |
|---|---|---|---|---|---|---|---|---|
| (p-tolyl)(phenyl)₂I | (23)-1 | (23)-19 | (23)-37 | (23)-55 | (23)-73 | (23)-91 | (23)-109 | (23)-127 |
| (p-tolyl)(p-methylphenyl)(phenyl)I | (23)-2 | (23)-20 | (23)-38 | (23)-56 | (23)-74 | (23)-92 | (23)-110 | (23)-128 |
| (p-tolyl)(p-methylphenyl)₂I | (23)-3 | (23)-21 | (23)-39 | (23)-57 | (23)-75 | (23)-93 | (23)-111 | (23)-129 |

TABLE 10-continued
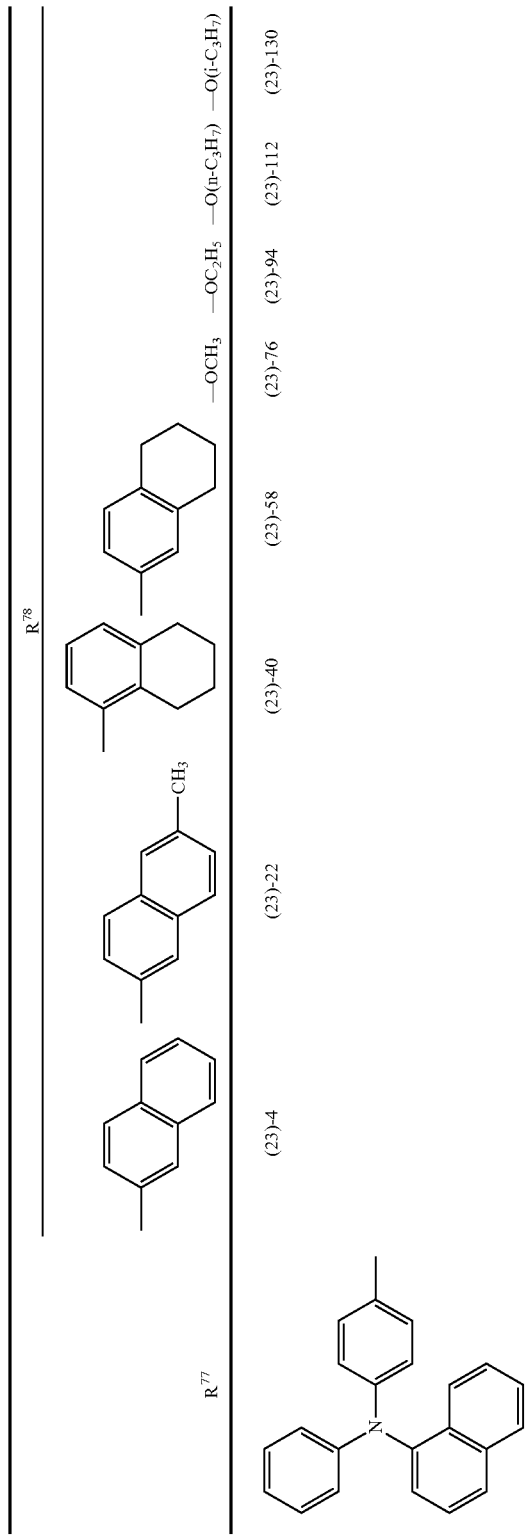
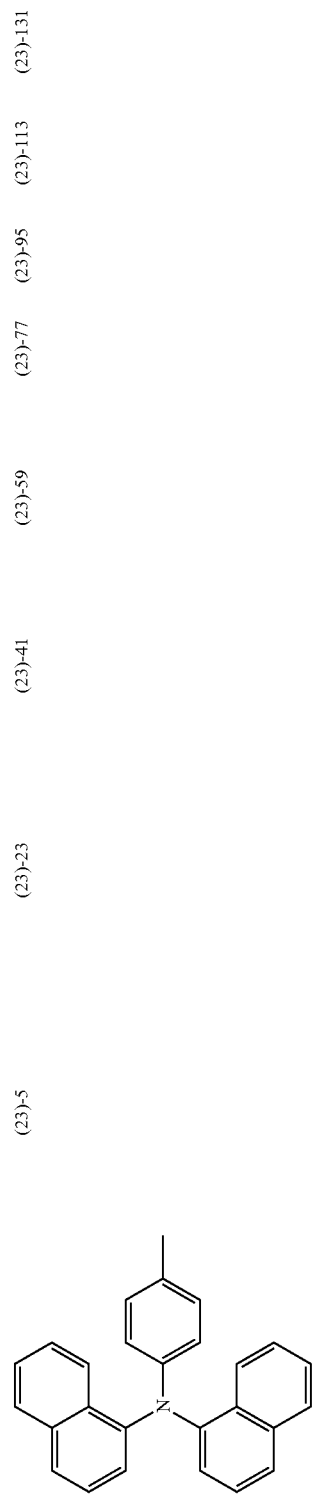

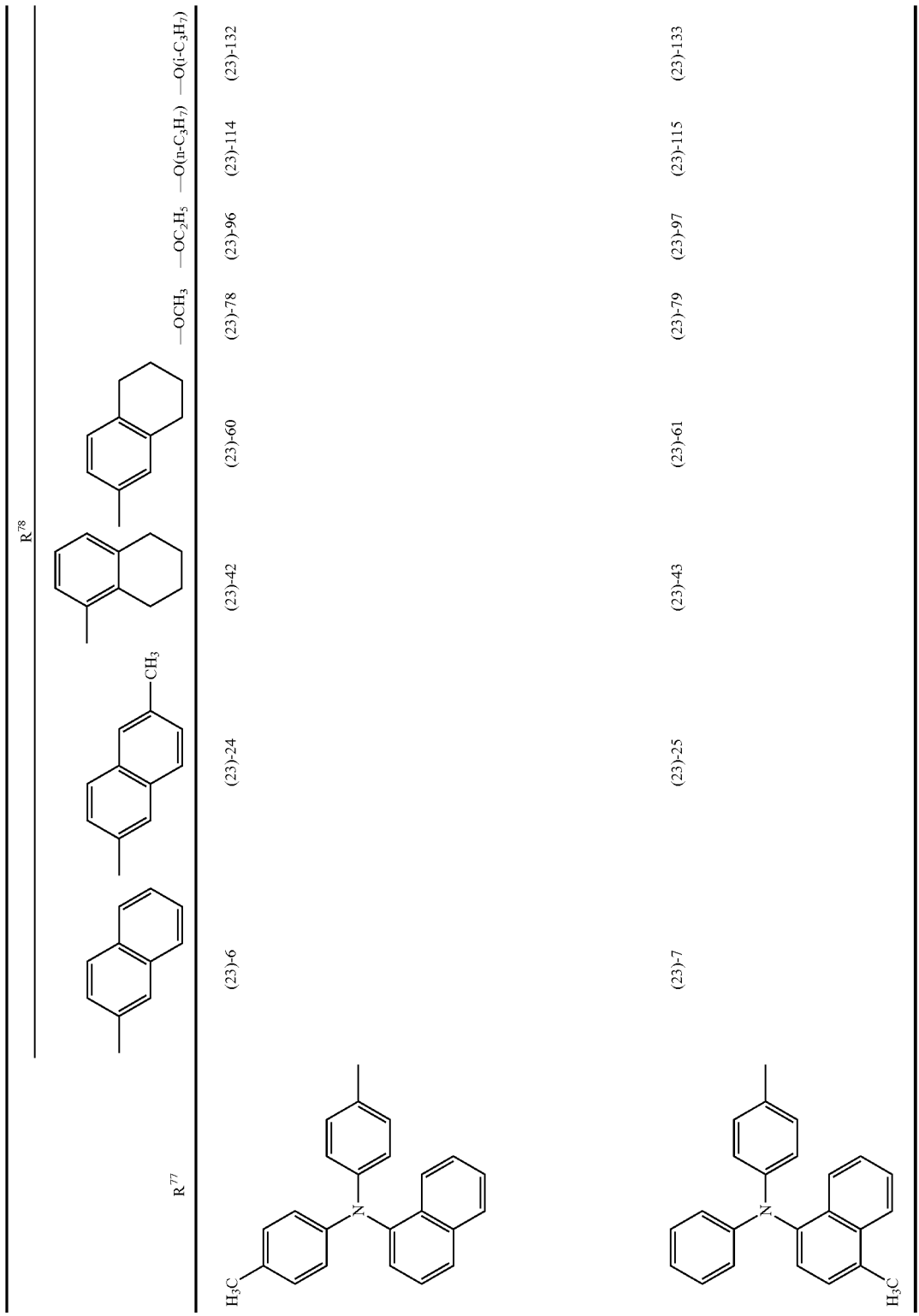

TABLE 11
| $R^{77}$ | $R^{78}$ | | | | | | | |
|---|---|---|---|---|---|---|---|---|
| | naphthyl | 2-Me-naphthyl | tetrahydronaphthyl-Me | tetrahydronaphthyl-Me | —OCH₃ | —OC₂H₅ | —O(n-C₃H₇) | —O(i-C₃H₇) |
|  | (23)-8 | (23)-26 | (23)-44 | (23)-62 | (23)-80 | (23)-98 | (23)-116 | (23)-134 |
| 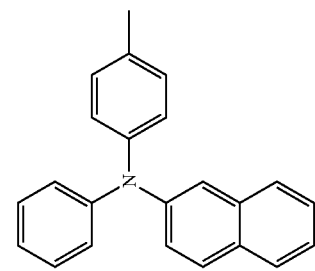 | (23)-9 | (23)-27 | (23)-45 | (23)-63 | (23)-81 | (23)-99 | (23)-117 | (23)-135 |

TABLE 11-continued
| R77 | R78 | | | | | | | |
|---|---|---|---|---|---|---|---|---|
| |  |  | 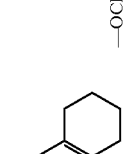 | 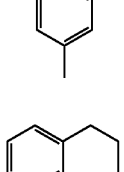 | —OCH₃ | —OC₂H₅ | —O(n-C₃H₇) | —O(i-C₃H₇) |
|  | (23)-10 | (23)-28 | (23)-46 | (23)-64 | (23)-82 | (23)-100 | (23)-118 | (23)-136 |
| 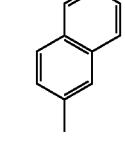 | (23)-11 | (23)-29 | (23)-47 | (23)-65 | (23)-83 | (23)-101 | (23)-119 | (23)-137 |

TABLE 11-continued

| $R^{77}$ | $R^{78}$ | | | | | | | |
|---|---|---|---|---|---|---|---|---|
| | naphthyl | 2-methylnaphthyl (CH₃) | methyl-tetrahydronaphthyl | methyl-tetrahydronaphthyl | —OCH₃ | —OC₂H₅ | —O(n-C₃H₇) | —O(i-C₃H₇) |
| N(phenyl)(p-tolyl)-naphthyl-CH₃ | (23)-12 | (23)-30 | (23)-48 | (23)-66 | (23)-84 | (23)-102 | (23)-120 | (23)-138 |
| N(p-tolyl)₂-naphthyl-CH₃ | (23)-13 | (23)-31 | (23)-49 | (23)-67 | (23)-85 | (23)-103 | (23)-121 | (23)-139 |

TABLE 11-continued
| R77 | R78 | | | | | | | |
|---|---|---|---|---|---|---|---|---|
|  |  | 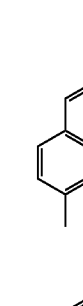 | 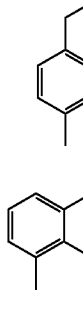 |  | —OCH₃ | —OC₂H₅ | —O(n-C₃H₇) | —O(i-C₃H₇) |
| | (23)-14 | (23)-32 | (23)-50 | (23)-68 | (23)-86 | (23)-104 | (23)-122 | (23)-140 |

TABLE 12
| $R^{77}$ | $R^{78}$ | | | | | | | |
|---|---|---|---|---|---|---|---|---|
| | 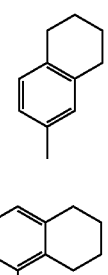 |  | 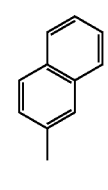 |  | —OCH₃ | —OC₂H₅ | —O(n-C₃H₇) | —O(i-C₃H₇) |
|  | (23)-15 | (23)-33 | (23)-51 | (23)-69 | (23)-87 | (23)-105 | (23)-123 | (23)-141 |
| 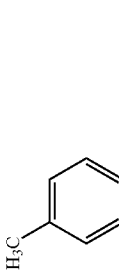 | (23)-16 | (23)-34 | (23)-52 | (23)-70 | (23)-88 | (23)-106 | (23)-124 | (23)-142 |

TABLE 12-continued

| $R^{77}$ | $R^{78}$ | | | | | | | |
|---|---|---|---|---|---|---|---|---|
| | naphthalen-2-yl | 2-methylnaphthalen-2-yl | 5-methyltetralin-yl | 6-methyltetralin-yl | —OCH$_3$ | —OC$_2$H$_5$ | —O(n-C$_3$H$_7$) | —O(i-C$_3$H$_7$) |
| (4-methylphenyl)(4-methoxyphenyl)(phenyl)iodonium | (23)-17 | (23)-35 | (23)-53 | (23)-71 | (23)-89 | (23)-107 | (23)-125 | (23)-143 |
| bis(4-methoxyphenyl)(4-methylphenyl)iodonium | (23)-18 | (23)-36 | (23)-54 | (23)-72 | (23)-90 | (23)-108 | (23)-126 | (23)-144 |

TABLE 13
| R⁷⁷ | R⁷⁸ | | | | | | |
|---|---|---|---|---|---|---|---|
| | —O(n-C₄H₉) | —O(i-C₄H₉) | —O(t-C₄H₉) | (methoxyphenoxyphenyl) | (methylphenyl) | (methoxy-methylphenyl) | (ethoxyphenyl) | (n-propylphenyl) |
| 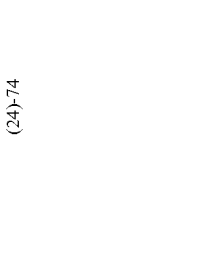 | (24)-1 | (24)-19 | (24)-37 | (24)-55 | (24)-73 | (24)-91 | (24)-109 | (24)-127 |
|  | (24)-2 | (24)-20 | (24)-38 | (24)-56 | (24)-74 | (24)-92 | (24)-110 | (24)-128 |
|  | (24)-3 | (24)-21 | (24)-39 | (24)-57 | (24)-75 | (24)-93 | (24)-111 | (24)-129 |

TABLE 13-continued

| R^77 | R^78 | | | | | | | |
|---|---|---|---|---|---|---|---|---|
| | —O(n-C₄H₉) | —O(i-C₄H₉) | —O(t-C₄H₉) | —O—C₆H₄—O—C₆H₄— | —O—C₆H₄—O—C₆H₄—CH₃ | —O—C₆H₄(CH₃)—O— | —O—C₆H₄—O—C₂H₅ | —O—C₆H₄—n-C₃H₇ |
| N(phenyl)(p-tolyl)(1-naphthyl) | (24)-4 | (24)-22 | (24)-40 | (24)-58 | (24)-76 | (24)-94 | (24)-112 | (24)-130 |
| N(p-tolyl)(1-naphthyl)(1-naphthyl) | (24)-5 | (24)-23 | (24)-41 | (24)-59 | (24)-77 | (24)-95 | (24)-113 | (24)-131 |
| N(p-tolyl)(p-tolyl)(1-naphthyl) | (24)-6 | (24)-24 | (24)-42 | (24)-60 | (24)-78 | (24)-96 | (24)-114 | (24)-132 |

TABLE 13-continued

| R⁷⁷ | R⁷⁸ | |
|---|---|---|
| —O(n-C₄H₉) | | (24)-7 |
| —O(i-C₄H₉) | | (24)-25 |
| —O(t-C₄H₉) | | (24)-43 |
| | 4-methoxyphenoxyphenyl | (24)-61 |
| | 4-methylphenoxy | (24)-79 |
| | 3-methoxyphenyl | (24)-97 |
| | 4-ethylphenoxy | (24)-115 |
| | 4-n-propylphenyl | (24)-133 |

TABLE 14

| R<sup>77</sup> | R<sup>78</sup> | | | | | | | |
|---|---|---|---|---|---|---|---|---|
| | —O(n-C₄H₉) | —O(i-C₄H₉) | —O(t-C₄H₉) | 4-methoxyphenoxy-phenyl | 4-methylphenoxy-phenyl | 3-methoxybenzyl | 4-ethoxyphenyl | 4-n-propylphenoxy |
| N(p-tolyl)(p-tolyl)(1,4-dimethylnaphth-1-yl) | (24)-8 | (24)-26 | (24)-44 | (24)-62 | (24)-80 | (24)-98 | (24)-116 | (24)-134 |
| N(p-tolyl)(phenyl)(2-naphthyl) | (24)-9 | (24)-27 | (24)-45 | (24)-63 | (24)-81 | (24)-99 | (24)-117 | (24)-135 |

TABLE 14-continued

| $R^{77}$ | $R^{78}$ | | | | | | | |
|---|---|---|---|---|---|---|---|---|
| (di-2-naphthyl)(p-tolyl)amine structure | —O(n-C₄H₉) | —O(i-C₄H₉) | —O(t-C₄H₉) | —O-C₆H₄-O-C₆H₄-OCH₃ (p,p) | —O-C₆H₄-CH₃ (p) | —O-C₆H₄-OCH₃ (m) with CH₃ | —O-C₆H₄-C₂H₅ (p) | —O-C₆H₄-n-C₃H₇ (p) |
| | (24)-10 | (24)-28 | (24)-46 | (24)-64 | (24)-82 | (24)-100 | (24)-118 | (24)-136 |
| (2-naphthyl)(p-tolyl)(4-methylphenyl)amine structure | (24)-11 | (24)-29 | (24)-47 | (24)-65 | (24)-83 | (24)-101 | (24)-119 | (24)-137 |

TABLE 14-continued
| $R^{77}$ | $R^{78}$ | | | | | | | |
|---|---|---|---|---|---|---|---|---|
| | —O(n-C₄H₉) | —O(i-C₄H₉) | —O(t-C₄H₉) | 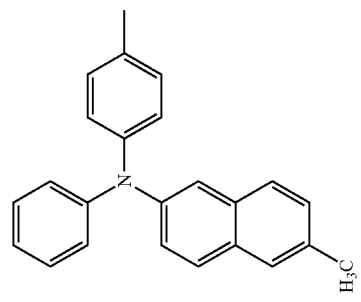 | 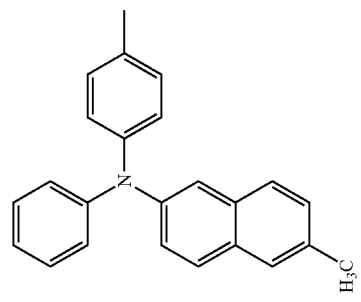 | 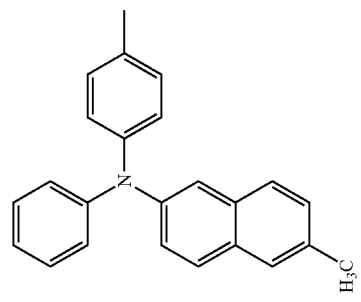 | 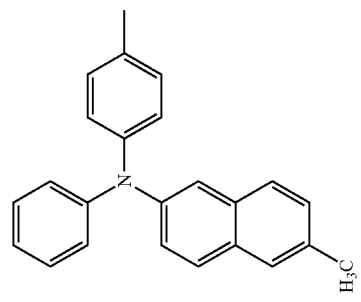 | 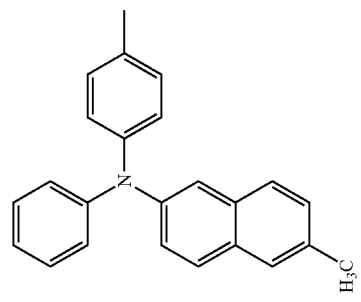 |
| 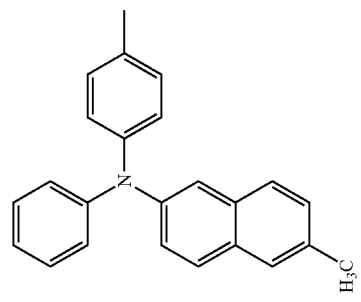 | (24)-12 | (24)-30 | (24)-48 | (24)-66 | (24)-84 | (24)-102 | (24)-120 | (24)-138 |
| 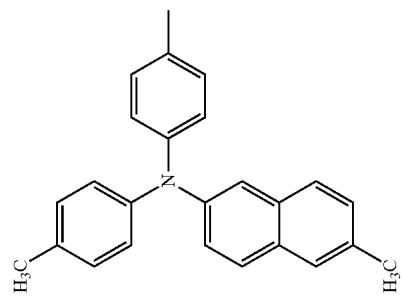 | (24)-13 | (24)-31 | (24)-49 | (24)-67 | (24)-85 | (24)-103 | (24)-121 | (24)-139 |

TABLE 14-continued

| R⁷⁷ | R⁷⁸ | |
|---|---|---|
| ![structure: N-phenyl-N-(p-tolyl)-5,6,7,8-tetrahydronaphthalen-1-amine] | —O(n-C₄H₉) | (24)-14 |
| | —O(i-C₄H₉) | (24)-32 |
| | —O(t-C₄H₉) | (24)-50 |
| | 4-(4-methoxyphenoxy)phenyl | (24)-68 |
| | 4-methoxyphenyl (with CH₃) | (24)-86 |
| | 3-methoxyphenyl (with CH₃) | (24)-104 |
| | 4-ethylphenoxy | (24)-122 |
| | 4-(n-propyl)phenoxy | (24)-140 |

TABLE 15

| R77 | R78 | | | | | | | |
|---|---|---|---|---|---|---|---|---|
| | —O(n-C$_4$H$_9$) | —O(i-C$_4$H$_9$) | —O(t-C$_4$H$_9$) | 4-MeO-C$_6$H$_4$-O-C$_6$H$_4$- | 4-CH$_3$-C$_6$H$_4$- | 3-CH$_3$O-C$_6$H$_4$- | 4-C$_2$H$_5$-C$_6$H$_4$-O- | 4-n-C$_3$H$_7$-C$_6$H$_4$- |
| di(4-methylphenyl)amino-5,6,7,8-tetrahydronaphthalen-1-yl | (24)-15 | (24)-33 | (24)-51 | (24)-69 | (24)-87 | (24)-105 | (24)-123 | (24)-141 |
| (4-methylphenyl)(phenyl)amino-5,6,7,8-tetrahydronaphthalen-2-yl | (24)-16 | (24)-34 | (24)-52 | (24)-70 | (24)-88 | (24)-106 | (24)-124 | (24)-142 |

TABLE 15-continued

| R⁷⁷ | R⁷⁸ | | | | | | | |
|---|---|---|---|---|---|---|---|---|
| | —O(n-C₄H₉) | —O(i-C₄H₉) | —O(t-C₄H₉) | 4-(4-methoxyphenoxy)phenyl | 4-methoxybenzyl (CH₃-C₆H₄-O—) | 3-methoxyphenyl | 4-ethylphenoxy | 4-(n-C₃H₇)phenoxy |
| p-tolyl, phenyl, 4-methoxyphenyl amine | (24)-17 | (24)-35 | (24)-53 | (24)-71 | (24)-89 | (24)-107 | (24)-125 | (24)-143 |
| p-tolyl, bis(4-methoxyphenyl) amine | (24)-18 | (24)-36 | (24)-54 | (24)-72 | (24)-90 | (24)-108 | (24)-126 | (24)-144 |

TABLE 16

| $R^{77}$ | $R^{78}$ | | | |
|---|---|---|---|---|
| | —O—i-C₃H₇ | —O—n-C₄H₉ | —O—i-C₄H₉ | —O—t-C₄H₉ |
| (structure 1) | (25)-1 | (25)-19 | (25)-37 | (25)-55 |
| (structure 2) | (25)-2 | (25)-20 | (25)-38 | (25)-56 |
| (structure 3) | (25)-3 | (25)-21 | (25)-39 | (25)-57 |

TABLE 16-continued

| (25)-4 | (25)-22 | (25)-40 | (25)-58 |
| (25)-5 | (25)-23 | (25)-41 | (25)-59 |
| (25)-6 | (25)-24 | (25)-42 | (25)-60 |

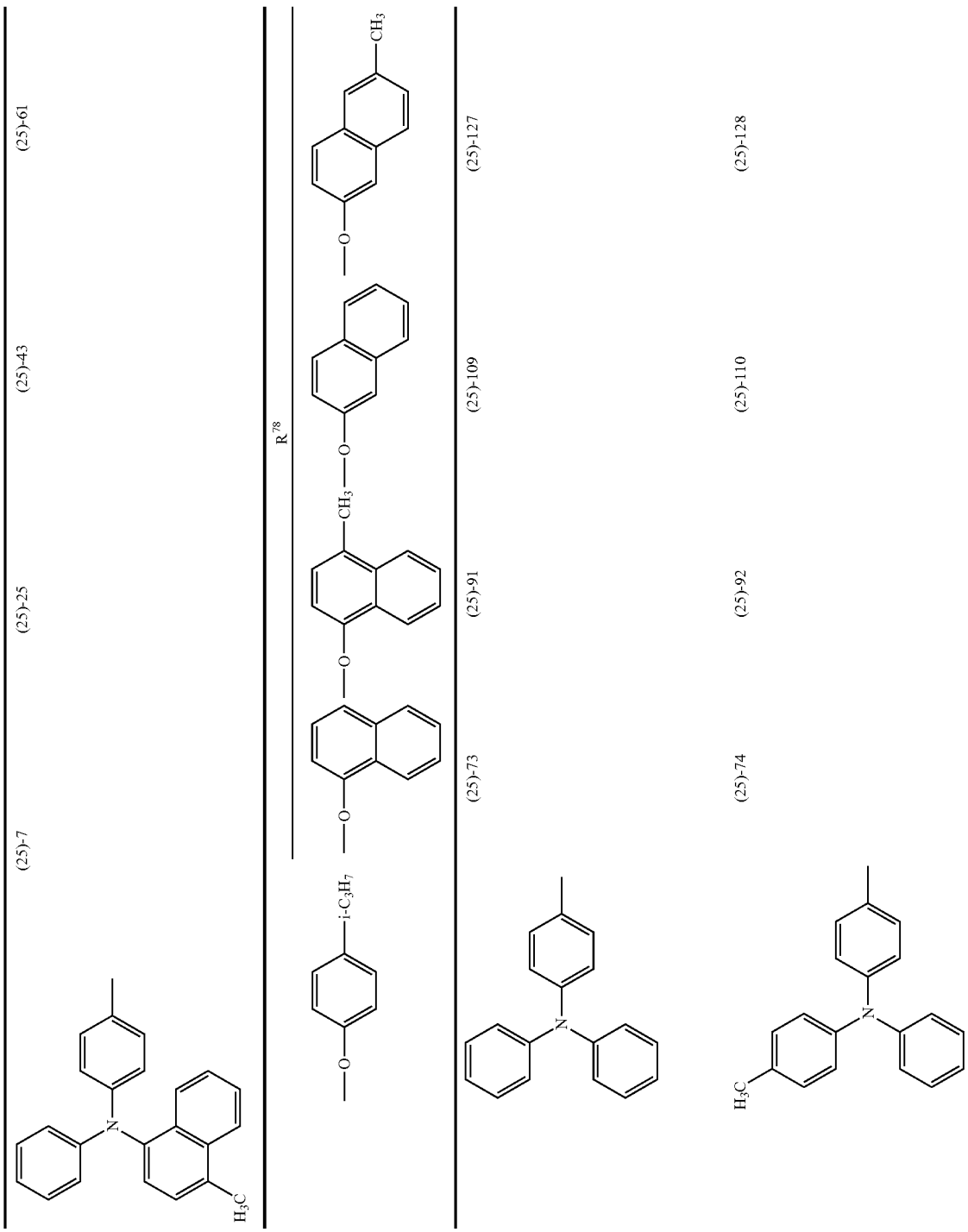

TABLE 16-continued

| (25)-75 | (25)-93 | (25)-111 | (25)-129 |
| (25)-76 | (25)-94 | (25)-112 | (25)-130 |
| (25)-77 | (25)-95 | (25)-113 | (25)-131 |

TABLE 16-continued
| (25)-78 | (25)-96 | (25)-114 | (25)-132 |
| --- | --- | --- | --- |
| 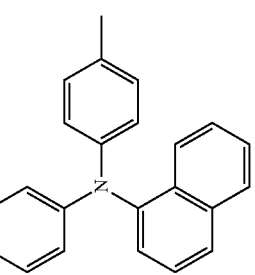 | | | |
| (25)-79 | (25)-97 | (25)-115 | (25)-133 |
| --- | --- | --- | --- |
| 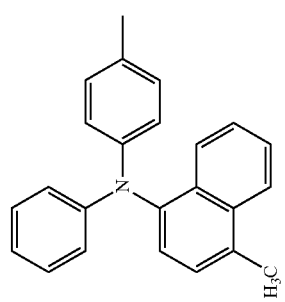 | | | |

TABLE 17
| $R^{77}$ | $R^{78}$ | | | | |
|---|---|---|---|---|---|
| | —O—i-C₃H₇ | (25)-8 | —O—n-C₄H₉ | (25)-26 | —O—i-C₄H₉ | (25)-44 | —O—t-C₄H₉ | (25)-62 |
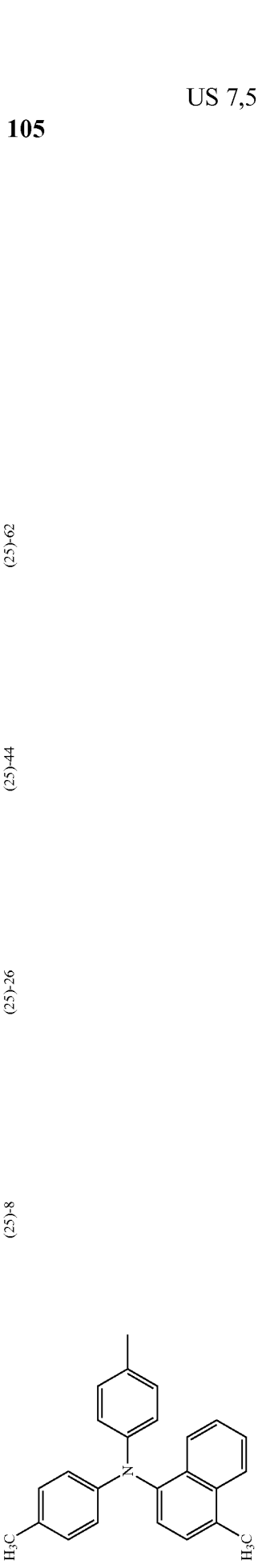
(25)-9   (25)-27   (25)-45   (25)-63

TABLE 17-continued

| (25)-10 | (25)-28 | (25)-46 | (25)-64 |
|---------|---------|---------|---------|
|         |         |         |         |

| (25)-11 | (25)-29 | (25)-47 | (25)-65 |
|---------|---------|---------|---------|
|         |         |         |         |

TABLE 17-continued

| (25)-12 | (25)-30 | (25)-48 | (25)-66 |
| (25)-13 | (25)-31 | (25)-49 | (25)-67 |
| (25)-14 | (25)-32 | (25)-50 | (25)-68 |

TABLE 17-continued

| $R^{77}$ | $R^{78}$ | | | | |
|---|---|---|---|---|---|
| | (25)-80 | (25)-98 | (25)-116 | (25)-134 | |
| | (25)-81 | (25)-99 | (25)-117 | (25)-135 | |

TABLE 17-continued
| (25)-82 | (25)-100 | (25)-118 | (25)-136 |
|---|---|---|---|
| 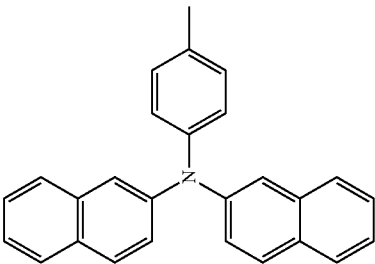 | | | |
| (25)-83 | (25)-101 | (25)-119 | (25)-137 |
|---|---|---|---|
| 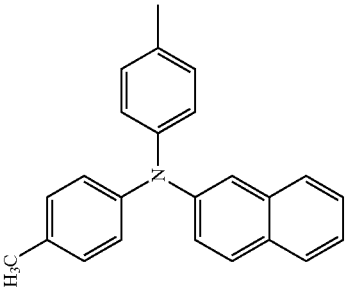 | | | |

TABLE 17-continued

| | | | |
|---|---|---|---|
| (25)-84 | (25)-102 | (25)-120 | (25)-138 |
| (25)-85 | (25)-103 | (25)-121 | (25)-139 |
| (25)-86 | (25)-104 | (25)-122 | (25)-140 |

TABLE 18
| R⁷⁷ | R⁷⁸ | | | |
|---|---|---|---|---|
| | —O—⟨phenyl⟩—i-C₃H₇ | —O—⟨phenyl⟩—n-C₄H₉ | —O—⟨phenyl⟩—i-C₄H₉ | —O—⟨phenyl⟩—t-C₄H₉ |
|  | (25)-15 | (25)-33 | (25)-51 | (25)-69 |
|  | (25)-16 | (25)-34 | (25)-52 | (25)-70 |
|  | (25)-17 | (25)-35 | (25)-53 | (25)-71 |

TABLE 18-continued
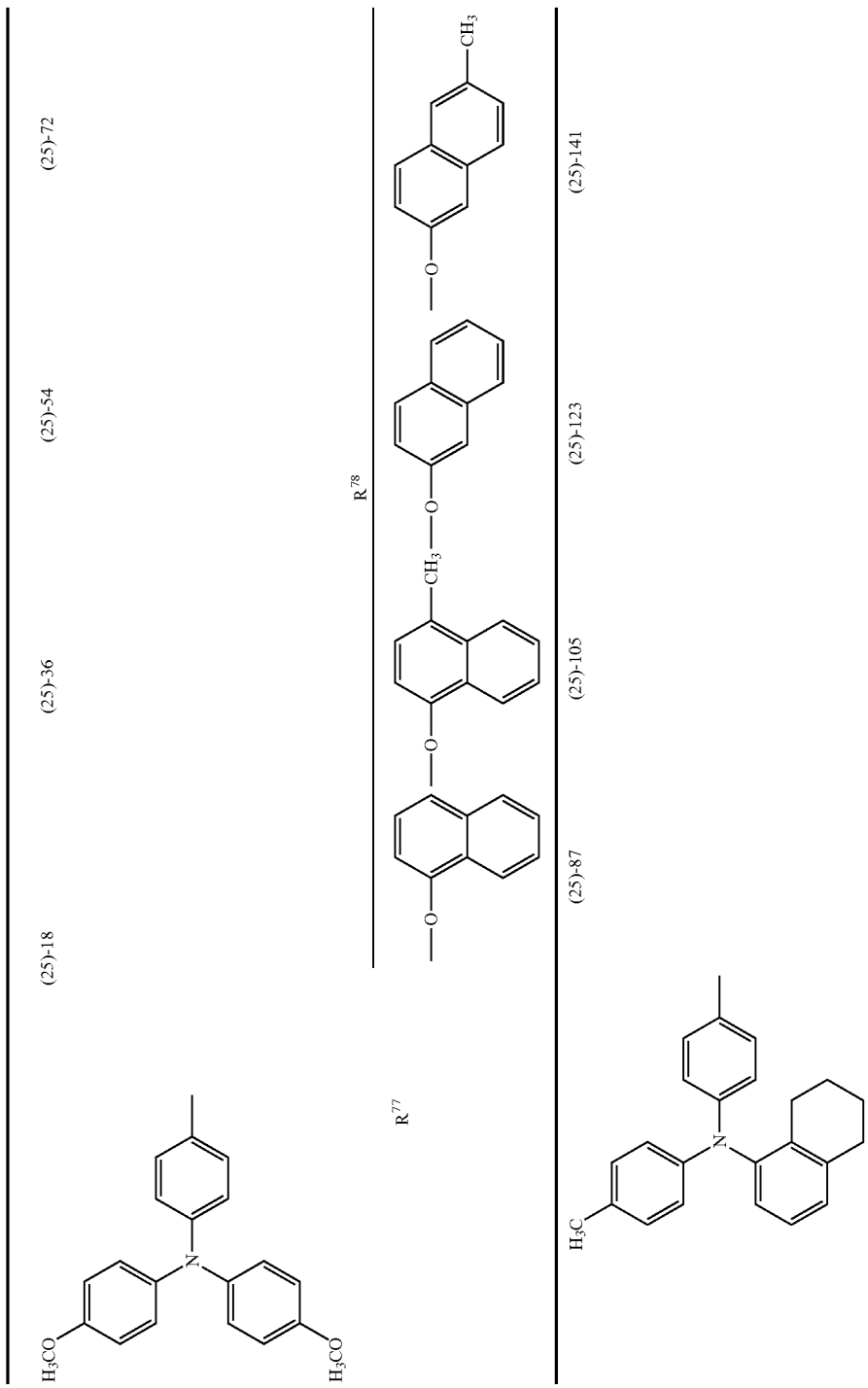

TABLE 18-continued

| (25)-88 | (25)-106 | (25)-124 | (25)-142 |
| (25)-89 | (25)-107 | (25)-125 | (25)-143 |
| (25)-90 | (25)-108 | (25)-126 | (25)-144 |

TABLE 19
| $R^{77}$ | $R^{78}$ | | | |
|---|---|---|---|---|
| | ―O― 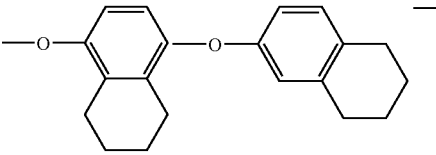 | ―O― 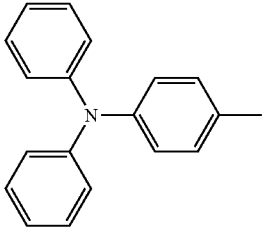 | 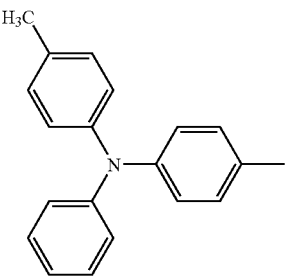―CF$_3$ | 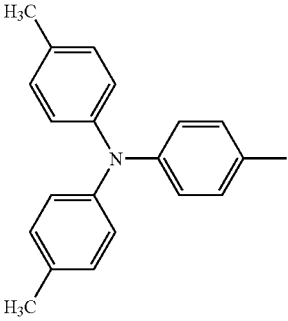 F$_3$C |
| 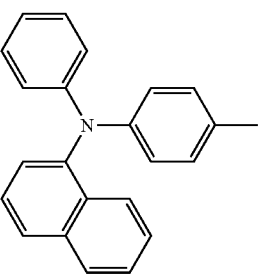 | (26)-1 | (26)-19 | (26)-37 | (26)-55 |
| H$_3$C— (triphenylamine) | (26)-2 | (26)-20 | (26)-38 | (26)-56 |
| H$_3$C— (tri-p-tolylamine) H$_3$C | (26)-3 | (26)-21 | (26)-39 | (26)-57 |
| (N-phenyl-N-tolyl-naphthylamine) | (26)-4 | (26)-22 | (26)-40 | (26)-58 |

TABLE 19-continued

| R77 (structure) | | | | |
|---|---|---|---|---|
| N-(1-naphthyl)-N-(p-tolyl)-1-naphthylamine | (26)-5 | (26)-23 | (26)-41 | (26)-59 |
| N,N-di(p-tolyl)-1-naphthylamine | (26)-6 | (26)-24 | (26)-42 | (26)-60 |
| N-phenyl-N-(p-tolyl)-4-methyl-1-naphthylamine | (26)-7 | (26)-25 | (26)-43 | (26)-61 |

| | R78 | | | |
|---|---|---|---|---|
| R77 | 3-(trifluoromethyl)styryl | 1-naphthylvinyl | 2-naphthylvinyl | 5,6,7,8-tetrahydro-1-naphthylvinyl |
| N,N-diphenyl-p-toluidine | (26)-73 | (26)-91 | (26)-109 | (26)-127 |

TABLE 19-continued

| Structure | | | | |
|---|---|---|---|---|
| [4-methylphenyl, phenyl, 4-methylphenyl amine] | (26)-74 | (26)-92 | (26)-110 | (26)-128 |
| [bis(4-methylphenyl), 4-methylphenyl amine] | (26)-75 | (26)-93 | (26)-111 | (26)-129 |
| [phenyl, 4-methylphenyl, 1-naphthyl amine] | (26)-76 | (26)-94 | (26)-112 | (26)-130 |
| [bis(1-naphthyl), 4-methylphenyl amine] | (26)-77 | (26)-95 | (26)-113 | (26)-131 |
| [4-methylphenyl, 4-methylphenyl, 1-naphthyl amine] | (26)-78 | (26)-96 | (26)-114 | (26)-132 |

TABLE 19-continued

| R77 (structure) | | | | |
|---|---|---|---|---|
| N-phenyl-N-(p-tolyl)-4-methylnaphthalen-1-amine | (26)-79 | (26)-97 | (26)-115 | (26)-133 |

TABLE 20

| R77 | R78 | | | |
|---|---|---|---|---|
| | —O—(methoxy-tetrahydronaphthalenyl)-O—(tetrahydronaphthalenyl) | | 4-CF3-styryl | 2-CF3-styryl |
| N,N-di(p-tolyl)-4-methylnaphthalen-1-amine | (26)-8 | (26)-26 | (26)-44 | (26)-62 |
| N-phenyl-N-(p-tolyl)naphthalen-2-amine | (26)-9 | (26)-27 | (26)-45 | (26)-63 |
| N-(naphthalen-2-yl)-N-(p-tolyl)amine | (26)-10 | (26)-28 | (26)-46 | (26)-64 |

TABLE 20-continued

| | | | | |
|---|---|---|---|---|
| *structure* | (26)-11 | (26)-29 | (26)-47 | (26)-65 |
| *structure* | (26)-12 | (26)-30 | (26)-48 | (26)-66 |
| *structure* | (26)-13 | (26)-31 | (26)-49 | (26)-67 |
| *structure* | (26)-14 | (26)-32 | (26)-50 | (26)-68 |

TABLE 20-continued

| R[77] | R[78] (3-CF3-styryl) | R[78] (1-naphthyl vinyl) | R[78] (2-naphthyl vinyl) | R[78] (tetrahydronaphthyl vinyl) |
|---|---|---|---|---|
| N,N-bis(4-methylphenyl)-4-methylnaphthalen-1-amine | (26)-80 | (26)-98 | (26)-116 | (26)-134 |
| N-phenyl-N-(4-methylphenyl)naphthalen-2-amine | (26)-81 | (26)-99 | (26)-117 | (26)-135 |
| N-(naphthalen-2-yl)-N-(4-methylphenyl)naphthalen-2-amine | (26)-82 | (26)-100 | (26)-118 | (26)-136 |
| N,N-bis(4-methylphenyl)naphthalen-2-amine | (26)-83 | (26)-101 | (26)-119 | (26)-137 |

TABLE 20-continued

| R | | | | |
|---|---|---|---|---|
| [structure: N-phenyl-N-(p-tolyl)-6-methyl-2-naphthylamine] | (26)-84 | (26)-102 | (26)-120 | (26)-138 |
| [structure: N-(m-tolyl)-N-(p-tolyl)-6-methyl-2-naphthylamine] | (26)-85 | (26)-103 | (26)-121 | (26)-139 |
| [structure: N-phenyl-N-(p-tolyl)-5-(1,2,3,4-tetrahydronaphthyl)amine] | (26)-86 | (26)-104 | (26)-122 | (26)-140 |

TABLE 21

| $R^{77}$ | $R^{78}$ | | | |
|---|---|---|---|---|
| | [5-methoxy-1,2,3,4-tetrahydronaphthyl-O-] | [6-(1,2,3,4-tetrahydronaphthyloxy)] | [4-(trifluoromethyl)styryl] | [2-(trifluoromethyl)styryl] |
| [N-(p-tolyl)-N-(5-(1,2,3,4-tetrahydronaphthyl))amine] | (26)-15 | (26)-33 | (26)-51 | (26)-69 |

TABLE 21-continued
| $R^{77}$ | | | | |
|---|---|---|---|---|
| 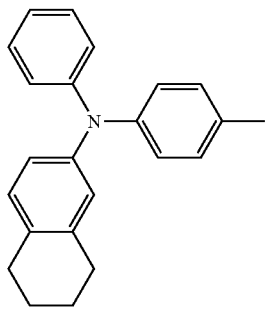 | (26)-16 | (26)-34 | (26)-52 | (26)-70 |
| 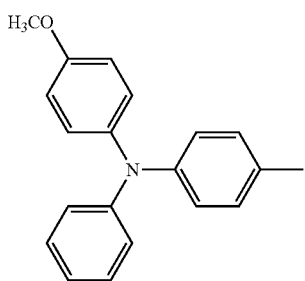 | (26)-17 | (26)-35 | (26)-53 | (26)-71 |
| 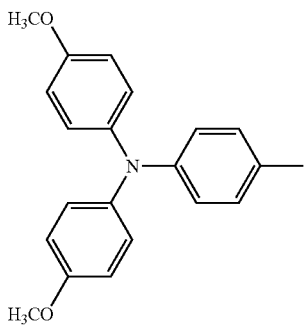 | (26)-18 | (26)-36 | (26)-54 | (26)-72 |
| | $R^{78}$ | | | |
|---|---|---|---|---|
| $R^{77}$ | 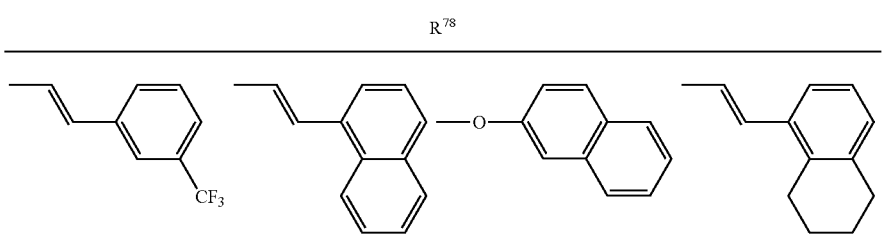 | | | |
| 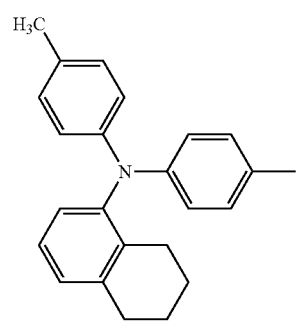 | (26)-87 | (26)-105 | (26)-123 | (26)-141 |

TABLE 21-continued

| R⁷⁷ structure | | | | |
|---|---|---|---|---|
| N-phenyl-N-(p-tolyl)-5,6,7,8-tetrahydronaphthalen-2-amine | (26)-88 | (26)-106 | (26)-124 | (26)-142 |
| 4-methoxy-N-phenyl-N-(p-tolyl)aniline | (26)-89 | (26)-107 | (26)-125 | (26)-143 |
| 4-methoxy-N-(4-methoxyphenyl)-N-(p-tolyl)aniline | (26)-90 | (26)-108 | (26)-126 | (26)-144 |

TABLE 22

| | R⁷⁸ | |
|---|---|---|
| R⁷⁷ | (27)-1 | (27)-19 |
| N,N-diphenyl-p-toluidine | | |

TABLE 22-continued
| R⁷⁷ | R⁷⁸ | |
|---|---|---|
| | 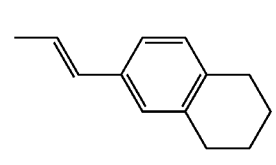 |  |
| 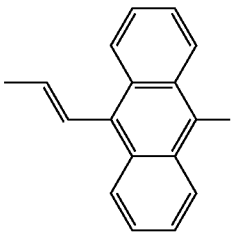 | (27)-2 | (27)-20 |
| 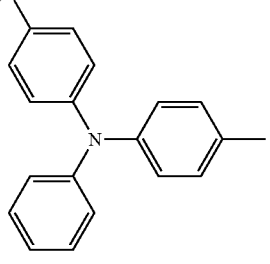 | (27)-3 | (27)-21 |
| 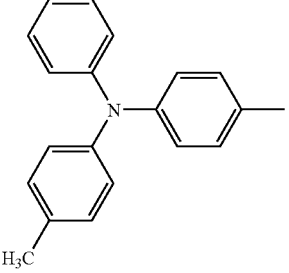 | (27)-4 | (27)-22 |
| 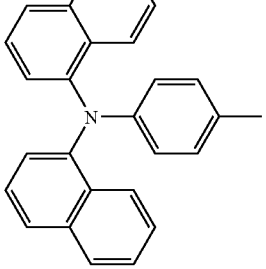 | (27)-5 | (27)-23 |

TABLE 22-continued
| $R^{77}$ | $R^{78}$ | |
|---|---|---|
| | 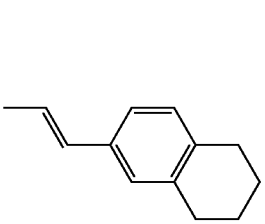 | 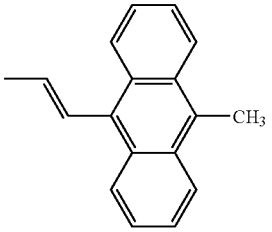 |
| | (27)-6 | (27)-24 |
| 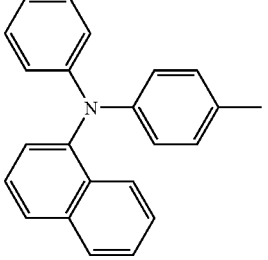 | | |
| | (27)-7 | (27)-25 |
| 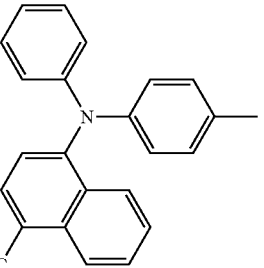 | | |
TABLE 23
| $R^{77}$ | $R^{78}$ | |
|---|---|---|
| | 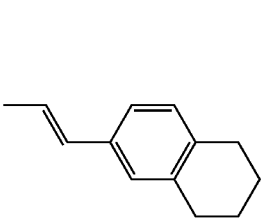 | 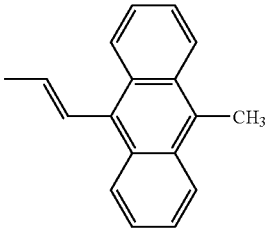 |
| | (27)-8 | (27)-26 |
| 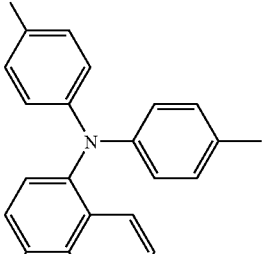 | | |

TABLE 23-continued

| $R^{77}$ | $R^{78}$ | |
|---|---|---|
| | (27)-9 | (27)-27 |
| | (27)-10 | (27)-28 |
| | (27)-11 | (27)-29 |

TABLE 23-continued

| R⁷⁷ | R⁷⁸ | |
|---|---|---|
| | (vinyl-tetrahydronaphthalene) | (propenyl-methylanthracene) |
| (phenyl-p-tolyl-amino-methylnaphthalene) | (27)-12 | (27)-30 |
| (di-p-tolyl-amino-methylnaphthalene) | (27)-13 | (27)-31 |
| (phenyl-p-tolyl-amino-tetrahydronaphthalene) | (27)-14 | (27)-32 |

TABLE 24
| R⁷⁷ | R⁷⁸ 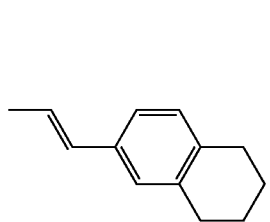 | R⁷⁸ 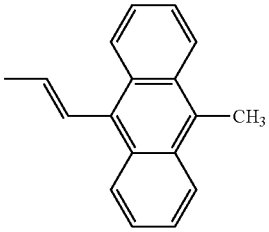 |
|---|---|---|
| 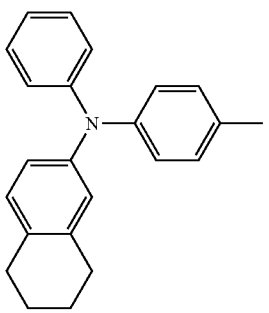 | (27)-15 | (27)-33 |
| 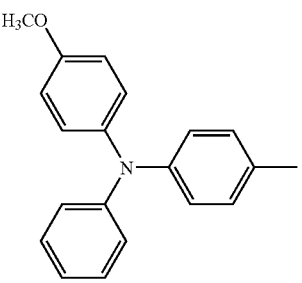 | (27)-16 | (27)-34 |
| 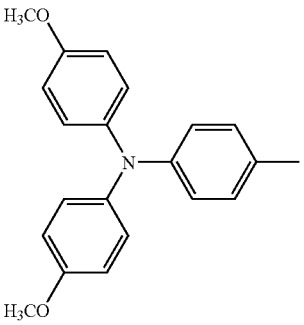 | (27)-17 | (27)-35 |
| | (27)-18 | (27)-36 |

Examples of materials usable for the formation of the organic electroluminescent device according to the present invention can include, in addition to the compounds according to the present invention, hole transport materials (for example, aromatic amines and the like), electron transport materials (for example, Alq$_3$, pyrazoline and the like), and a series of compounds commonly employed as red emission dopants (DCM and its analogous compounds, porphyrins, phthalocyanines, perylene compounds, Nile Red, squalilium compounds, and the like).

As a process for producing the compounds of the present invention with high efficiency, the present invention also provides a process for the production of an aminostyrylnaphthalene compound represented by the formula [A], especially the formula [I], [II] or [III], which comprises subjecting an aminobenzaldehyde represented by the following formula [B], especially the following formula [IV] and at least one of a phosphonate ester represented by the following formula [C], especially the following formula [V] and a phosphonium represented by the following formula [D], especially the following formula [VI] to condensation:

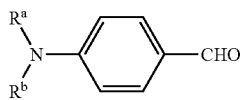

Formula [B]

wherein $R^a$ and $R^b$ have the same meaning as defined above.

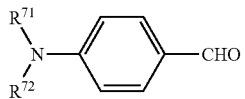

Formula [IV]

wherein $R^{71}$ and $R^{72}$ each independently represents an aryl group corresponding to $R^1$, $R^2$, $R^{11}$, $R^{12}$, $R^{23}$ or $R^{24}$.

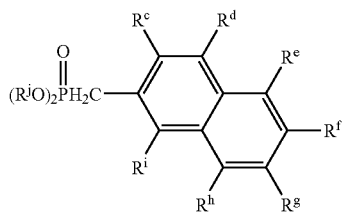

Formula [C]

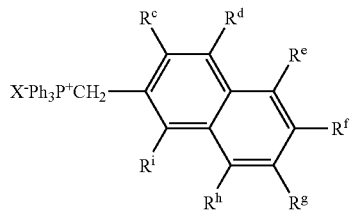

Formula [D]

wherein $R^j$ represents a hydrocarbon group, $R^c$, $R^d$, $R^e$, $R^f$, $R^g$, $R^h$ or $R^i$ have the same meanings as defined above, and X represents a halogen atom.

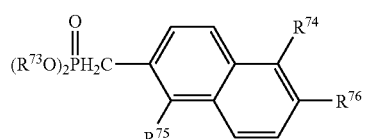

Formula [V]

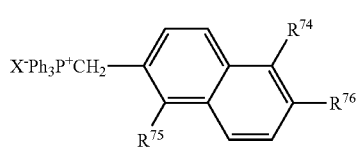

Formula [VI]

wherein $R^{73}$ represents a hydrocarbon group, preferably a saturated hydrocarbon group having 1 to 4 carbon atoms, $R^{74}$ and $R^{75}$ each independently represents a group corresponding to $R^3$, $R^4$, $R^{13}$, $R^{14}$, $R^{25}$ or $R^{26}$, $R^{76}$ represents a group corresponding to $R^5$, $R^{15}$ or $R^{27}$, and X represents a halogen atom.

In a specific embodiment of the process according to the present invention for the production of the aminostyrylnaphthalene compound, the condensation may be conducted by the Wittig-Horner reaction or the Wittig reaction, at least one of the phosphonate ester and the phosphonium may be treated with a base in a solvent to form carbanions, and the carbanions and the aminobenzaldehyde, especially the 4-(N,N-diarylamino)benzaldehyde may be subjected to condensation.

Upon obtaining, for example, an aminostyrylnaphthalene compound represented by the following formula (28):

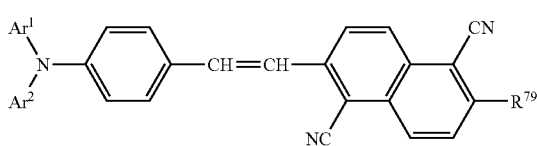

Formula (28)

wherein Ar$^1$ and Ar$^2$ are each the same as $R^1$, $R^2$, $R^{11}$, $R^{12}$, $R^{23}$ or $R^{24}$ as defined above, and $R^{79}$ is the same as $R^5$, $R^{15}$ or $R^{27}$ as defined above, a 4-(N,N-diarylamino)benzaldehyde represented by the following formula (29) and at least one of a phosphonate ester represented by the following formula (30) and a phosphonium represented by the following formula (31) are subjected to condensation.

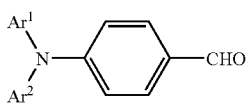

Formula (29)

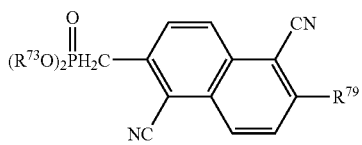

Formula (30)

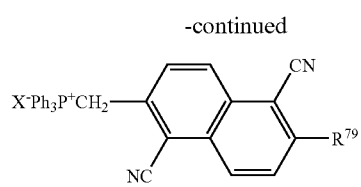

Formula (31)

wherein $Ar^1$, $Ar^2$, $R^{79}$ and X have the same meanings as defined above.

Expressing the above reactions by a scheme, they can be shown, for example, as illustrated by the following reaction scheme 1:

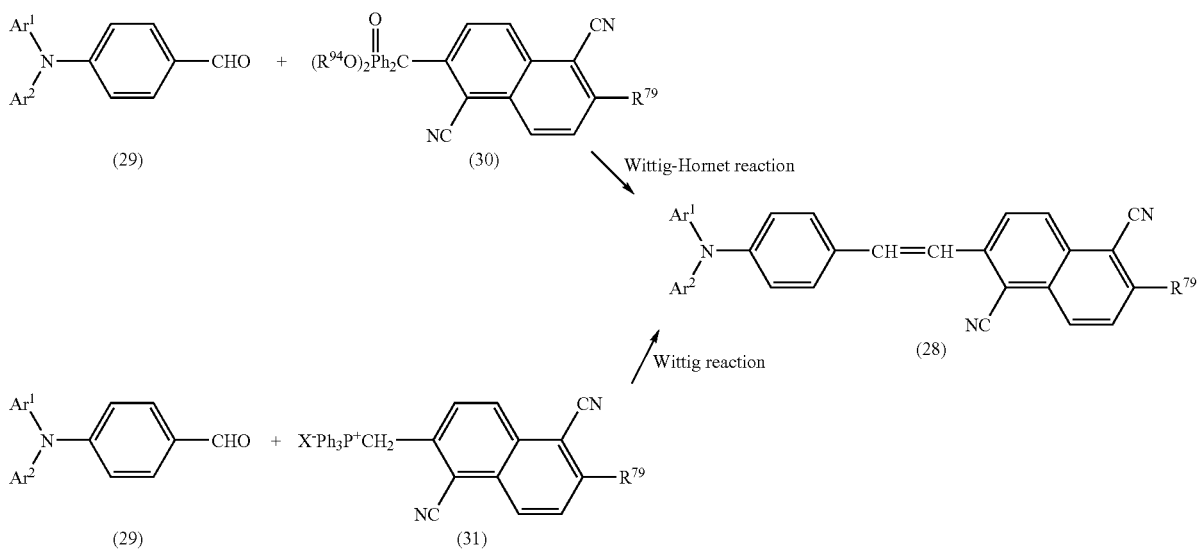

Reaction Scheme 1

The reactions firstly begin with the treatment of at least one of the compound of the formula (30) and the compound of the formula (31) with a base in an adequate solvent to produce carbanions. These carbanions and the aldehyde of the formula (29) are then subjected to condensation such that the reactions are completed. As examples of the combination of the base and the solvent, the following combinations can be mentioned.

Sodium hydroxide/water, sodium carbonate/water, potassium carbonate/water, sodium ethoxide/ethanol or dimethylformamide, sodium methoxide/methanol-diethyl ether mixed solvent or dimethylformamide, triethylamine/ethanol or diglyme or chloroform or nitromethane, pyridine/methylene chloride or nitromethane, 1,5-disazabicyclo[4.3.0]non-5-ene/dimethylsulfoxide, potassium t-butoxide/dimethylsulfoxide or tetrahydrofuran or benzene or dimethylformamide, phenyllithium/diethyl ether or tetrahydrofuran, t-butyllithium/diethyl ether or tetrahydrofuran, sodium amide/ammonia, sodium hydride/dimethylformamide or tetrahydrofuran, and triethylsodium/diethyl ether or tetrahydrofuran.

As the reactions proceed at relatively low temperatures (−30° C. to 30° C.) and are selective, the target product can be readily purified by chromatography, and owing to the high crystallinity of the compound of the present invention represented by the formula (28), its purity can be increased further by recrystallization. No particular limitation is imposed on the method of recrystallization, but the recrystallization may be conveniently conducted by dissolving the compound in acetone and then adding hexane to the resulting solution or by dissolving the compound in toluene under heat, concentrating the thus-prepared solution and then cooling the resultant concentrate. The reactions may be brought to completion in 3 to 24 hours under normal pressure.

By the production process according to the present invention, the aminostyrylnaphthalene compounds represented by the formulas (5) to (17), specifically the aminostyrylnaphthalene compounds shown above in Table 1 to Table 24 can be obtained.

The present invention also provides various compounds suitable as synthesis intermediates for the compound according to the present invention.

Specifically, they include the phosphonate ester represented by the formula [C], especially the formula [V] and the phosphonium represented by the formula [D], especially the formula [VI], which is useful as a synthesis intermediate for the aminostyrylnaphthalene compound represented by the formula [A], especially the formula [I], [II] or [III].

The synthesis intermediate (hereinafter called "the synthesis intermediate 1 of the present invention") is specifically represented by the following formula (18) or (19):

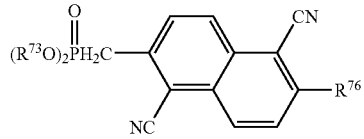

Formula (18)

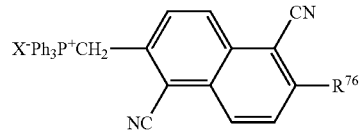

Formula (19)

wherein $R^{73}$, $R^{76}$ and X have the same meanings as defined above.

The synthesis intermediate 1 of the present invention can be derived from a synthesis intermediate 2 as a precursor as will be described next.

The phosphonate ester represented by the formula [C], especially the formula [V] [for example, the formula (18)] or the phosphonium represented by the formula [D], especially the formula [VI] [for example, the formula (19)] can be obtained as a synthesis intermediate by reacting a halogenated aryl compound represented by the below-described formula [E], especially the formula [VII] with a trialkyl phosphite represented by the below-described formula [F], especially the formula [VIII] or triphenylphosphine (PPh$_3$). This reaction can be brought to completion in 30 minutes to 24 hours at 120° C. to 160° C. under normal pressure in a solventless manner, in a solvent having a boiling point of 120° C. or higher such as xylene, or in a large excess of a trialkyl phosphite.

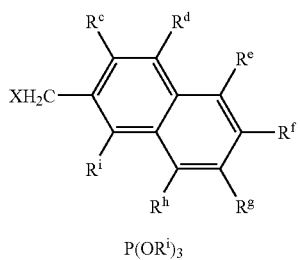

Formula [E]

P(OR$^j$)$_3$  Formula [F]

wherein R$^c$, R$^d$, R$^e$, R$^f$, R$^g$, R$^h$, R$^i$ and X have the same meanings as defined above, and R$^j$ represents a hydrocarbon group.

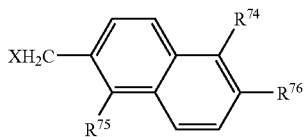

Formula [VII]

wherein R$^{74}$ and R$^{75}$ may be the same or different, one of R$^{74}$ and R$^{75}$ represents a hydrogen atom, a cyano group, a nitro group, a trifluoromethyl group or a halogen atom, and the remaining one represents a hydrogen atom, a cyano group, a nitro group, a trifluoromethyl group or a halogen atom; R$^{76}$ represents a substituted or unsubstituted, saturated or unsaturated alkyl group (especially, a saturated or unsaturated alkyl group having 1 to 6 carbon atoms), a substituted or unsubstituted alicyclic hydrocarbon group, a substituted or unsubstituted aryl group, a substituted or unsubstituted alkoxyl group, a substituted or unsubstituted alicyclic hydrocarbyloxy group, or a substituted or unsubstituted aromatic hydrocarbyloxy group; and X represents a halogen atom.

P(OR$^{73}$)$_3$  Formula [VIII]

wherein R$^{73}$ represents a hydrocarbon group, especially a saturated or unsaturated hydrocarbon group having 1 to 4 carbon atoms.

The present invention also provides, as a synthesis intermediate for the synthesis intermediate 1, a halogenated aryl compound represented by the formula [E], especially the formula [VII] (hereinafter called "the synthesis intermediate 2 of the present invention").

The synthesis intermediate 2 of the present invention can be obtained by reacting a naphthalene compound represented by the following formula [G], especially the formula [IX] with an N-halogenated succinimide represented by the following formula [H] under irradiation of light. For example, they can be reacted at 20 to 120° C. under normal pressure for 30 to 48 hours in a solvent such as carbon tetrachloride, chloroform, benzene or chlorobenzene by using a light source such as a high-pressure mercury lamp, low-pressure mercury lamp, xenon lamp, halogen lamp, sunlight or fluorescent lamp.

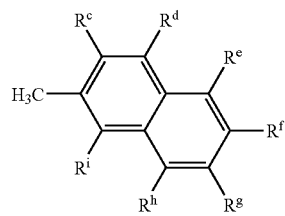

Formula [G]

wherein R$^c$, R$^d$, R$^e$, R$^f$, R$^g$, R$^h$ and R$^i$ have the same meanings as defined above.

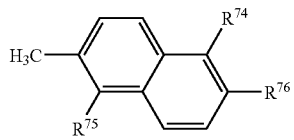

Formula [IX]

wherein R$^{74}$ and R$^{75}$ may be the same or different, one of R$^{74}$ and R$^{75}$ represents a hydrogen atom, a cyano group, a nitro group, a trifluoromethyl group or a halogen atom, the remaining one of R$^{74}$ and R$^{75}$ represents a hydrogen atom, a cyano group, a nitro group, a trifluoromethyl group or a halogen atom, and R$^{76}$ represents a substituted or unsubstituted, saturated or unsaturated alkyl group (especially, a saturated or unsaturated alkyl group having 1 to 6 carbon atoms), a substituted or unsubstituted alicyclic hydrocarbon group, a substituted or unsubstituted aryl group, a substituted or unsubstituted alkoxyl group, a substituted or unsubstituted alicyclic hydrocarbyloxy group, or a substituted or unsubstituted aromatic hydrocarbyloxy group.

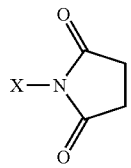

Formula [H]

wherein X represents a halogen atom.

The reactions for obtaining the above-mentioned, respective synthesis intermediates 1 and 2 can be expressed, for example, by the following reaction scheme 2:

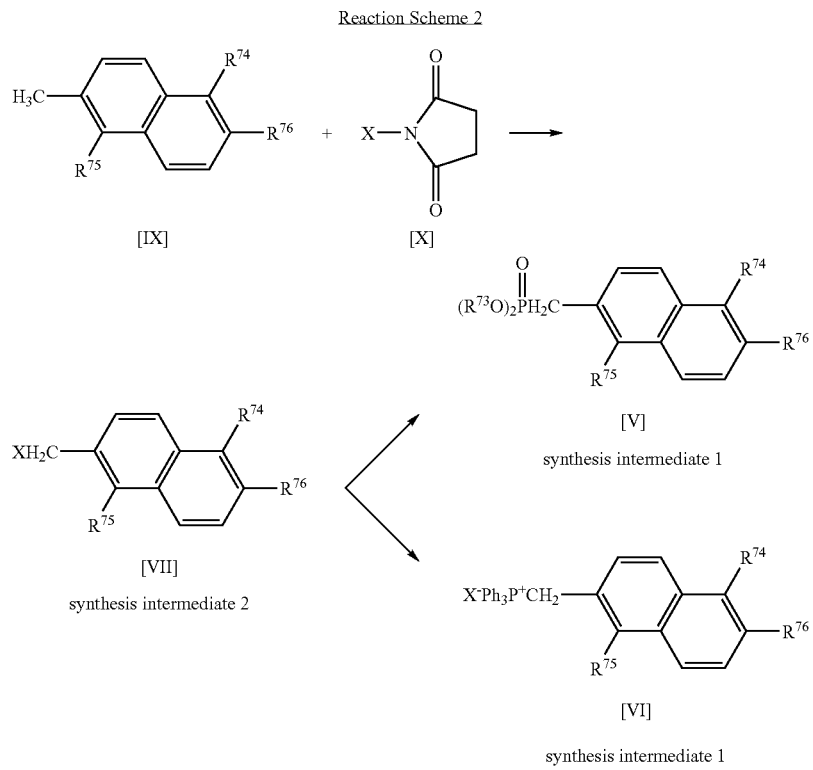

Reaction Scheme 2

FIG. 1 to FIG. 6 show organic electroluminescent devices according to various embodiments of the present invention, respectively.

Figure 2:
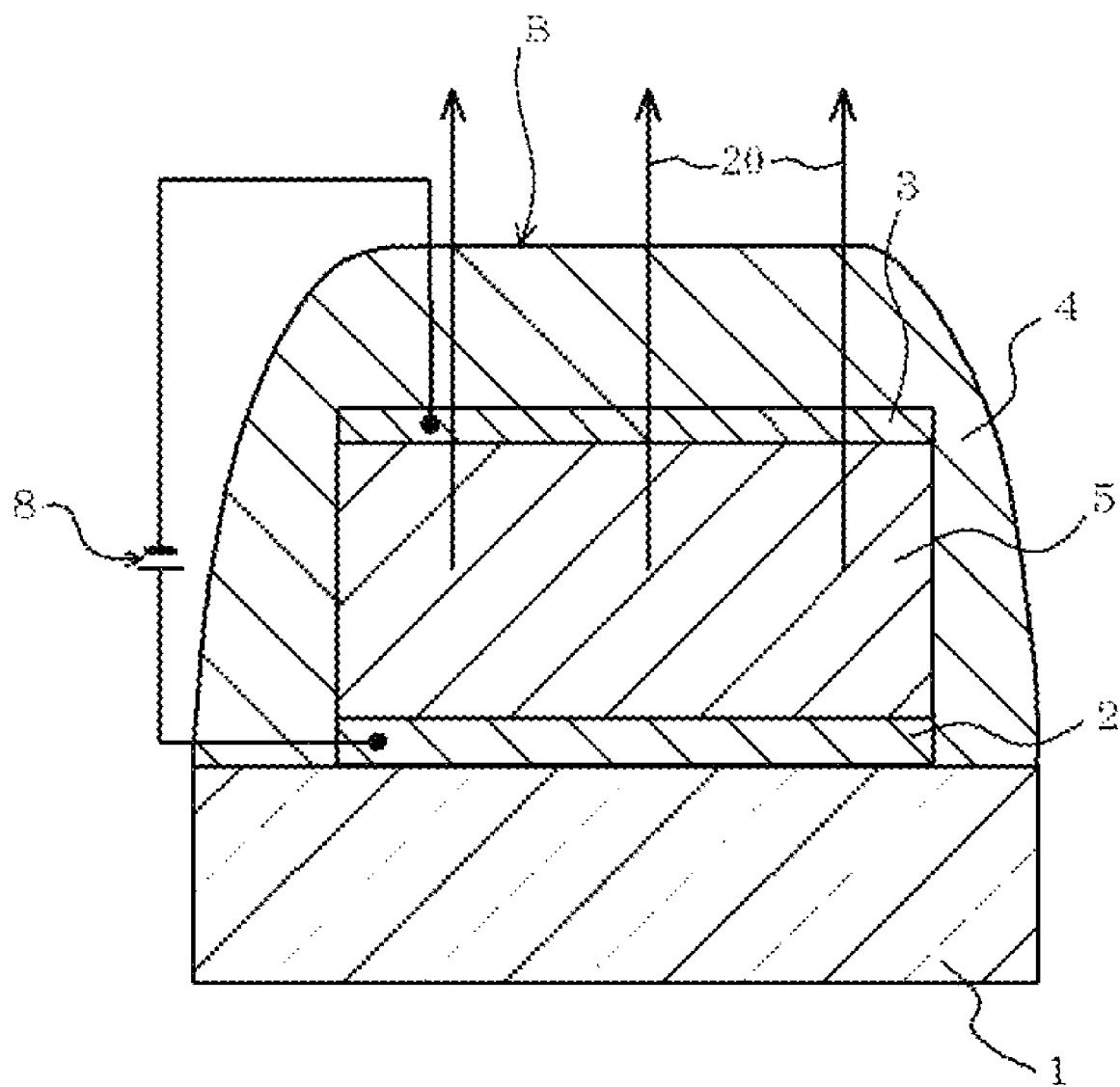
FIG. 2 is a schematic fragmentary cross-sectional view of an organic electroluminescent device according to another embodiment of the present invention.

FIG. 1 shows a bottom-emitting organic electroluminescent device A, in which emitted light 20 transmits through an anode 2 and light reflected by a cathode 3 is also obtained as emitted light 20. FIG. 2 illustrates a surface-emitting organic electroluminescent device B, in which light reflected by an anode 2 is also obtained as emitted light 20 through a thin cathode 3 and the emitted light 20 can be observed from the side of a protective layer 4.

In each of these drawings, numeral 1 indicates a substrate for forming the organic electroluminescent device. Glass, plastics or any other appropriate material is usable. When the organic electroluminescent device is used in combination with another display device, these devices can use a single substrate in common. In FIG. 1, the anode 2 is a transparent electrode and ITO (indium tin oxide), $SnO_2$ or the like can be used.

In each of FIG. 1 and FIG. 2, an organic luminescent layer 5 contains the above-described aminostyrylnaphthalene compound of the present invention as a light emitting material. As a multilayer structure of the luminescent layer 5 for obtaining the emitted light 20, various known structures can be used. As will be described subsequently herein, where a material forming either a hole transport layer or an electron transport layer has light emitting property, for example, a structure with these transport layers stacked as thin films one over the other can be used.

Further, the present invention does not prevent one or both of a hole transport layer and an electron transport layer from using a structure, which is formed of thin films of plural materials stacked one over another, or a thin film of a composition, which has been obtained by mixing plural materials, to improve the performance of electron transportation within a range in which the objects of the present invention are satisfied. To improve the light emitting performance, at least one fluorescent material may also be used in such a structure as having a thin film of the fluorescent material held between a hole transport layer and an electron transport layer or in such a structure as having the fluorescent material incorporated in a hole transport layer or an electron transport layer or in both of them. In these cases, a thin film for controlling the transport of holes or electrons may also be included in the multilayer structure.

As the aminostyrylnaphthalene compound represented by the formula [A], especially the formula [I], [II] or [III] is equipped with both of electron transporting ability and hole transporting ability, the compound can be used as a mixed luminescent layer together with an electron transporting material or as a mixed luminescent layer together with a hole transporting material in the device structure. Further, a mixed layer with the compound contained therein can be used as a light emitting material in such a structure as having the mixed layer held between an electron transport layer and a hole transport layer.

FIG. 1 and FIG. 2 each depicts the cathode 3. As an electrode material, it is possible to use an alloy or stacked structure of an active metal such as Li, Mg or Ca with a metal such as Ag, Al or In. In a transmission-type organic electroluminescent device, a light reflectance suited to its application purpose can be obtained by adjusting the thickness of its cathode. In each of FIG. 1 and FIG. 2, the protective film 4 has sealing property, and its effect can be enhanced by forming it into such a structure as covering the organic electroluminescent device in its entirety. Any suitable material can be used insofar as air tightness can be maintained.

In each organic electroluminescent device according to the present invention, the organic layer may have an organic multilayer structure (single heterostructure) with a hole transport layer and an electron transport layer stacked one over the other, and as the material forming the hole transport layer or the electron transport layer, a mixed layer with the aminostyrylnaphthalene compound contained therein can be used. As an alternative, the organic layer may have an organic multilayer structure (double heterostructure) with a hole transport layer, a luminescent layer and an electron transport layer stacked one over another, and as the material forming the luminescent layer, a mixed layer with the aminostyrylnaphthalene compound contained therein can be used.

Figure 3:
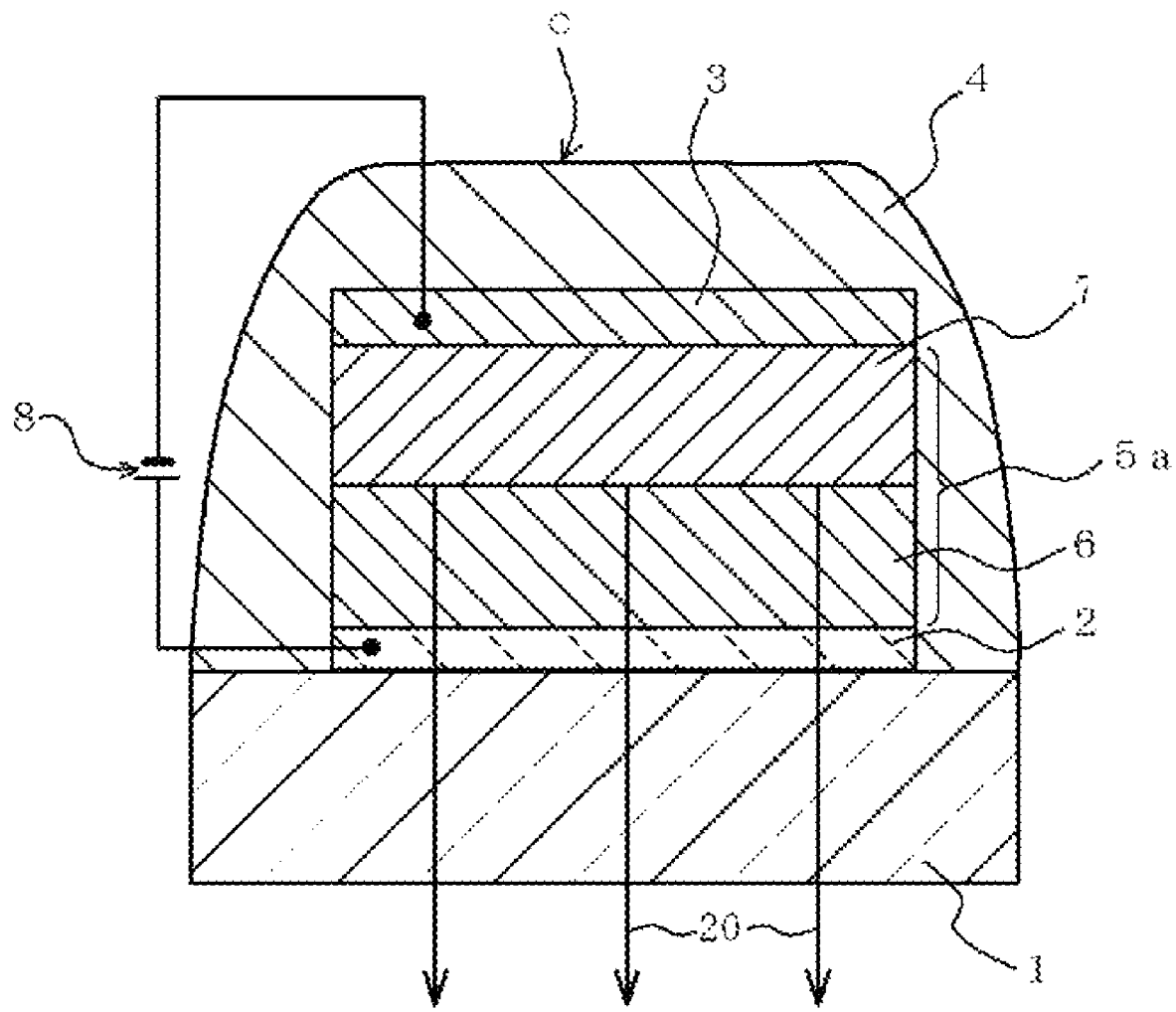
FIG. 3 is a schematic fragmentary cross-sectional view of an organic electroluminescent device according to a further embodiment of the present invention.

Organic electroluminescent devices according to other embodiments of the present invention, which have such organic multilayer structures, respectively, will hereinafter be described. FIG. 3 illustrates a bottom-emitting, organic electroluminescent device C of the single heterostructure, which has a multilayer structure formed of a light-transmitting anode 2, an organic layer 5a, and a cathode 3 stacked one over another on a light-transmitting substrate 1. The organic layer 5a is composed of a hole transport layer 6 and an electron transport layer 7. The multilayer structure is sealed with a protective layer 4.

In the case of a layer construction with a luminescent layer omitted as shown in FIG. 3, emitted light 20 of a predetermined wavelength is produced from an interface between the hole transport layer 6 and the electron transport layer 7. The emitted light can be observed from the side of the substrate 1.

Figure 4:
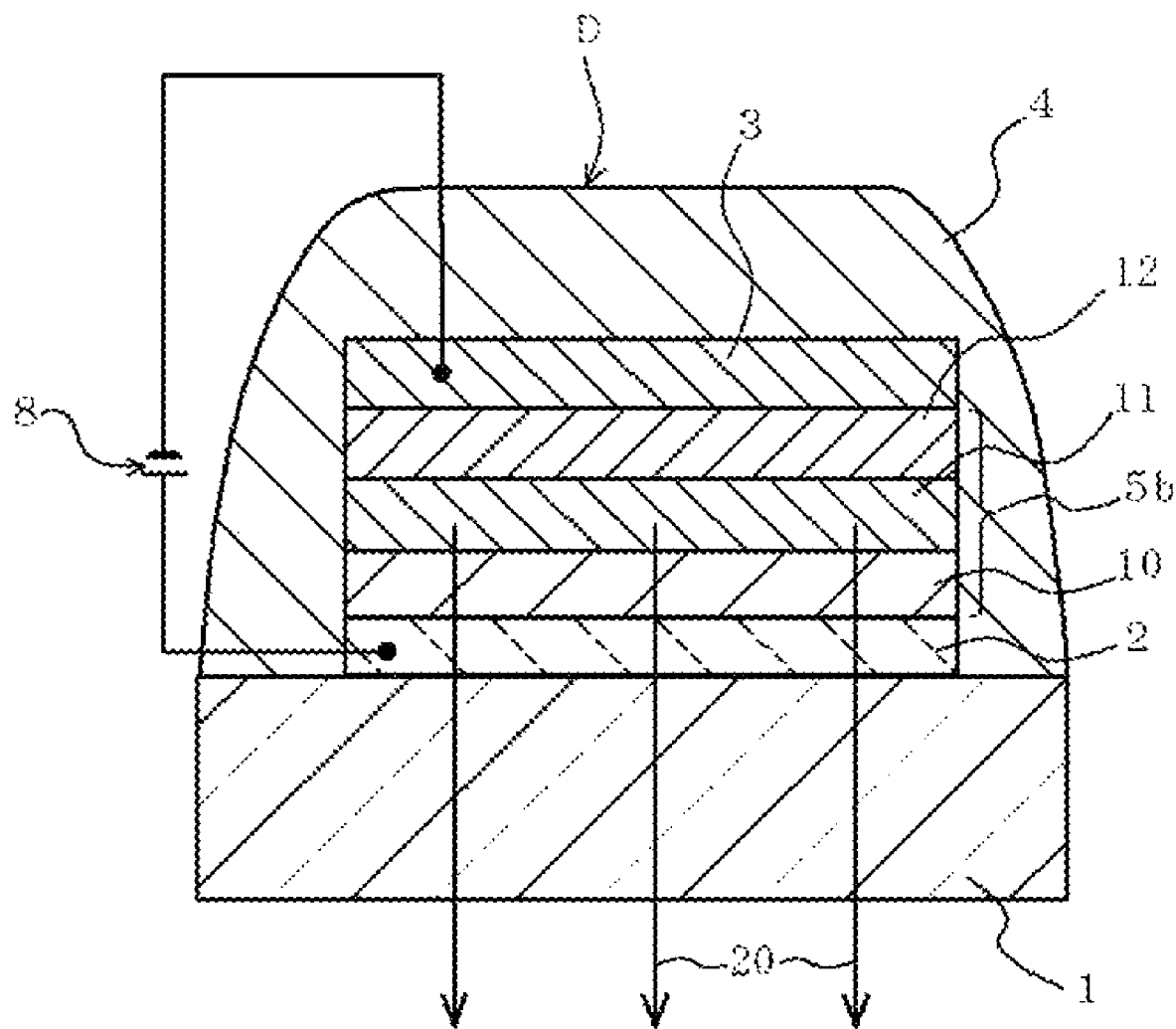
FIG. 4 is a schematic fragmentary cross-sectional view of an organic electroluminescent device according to a still further embodiment of the present invention.

FIG. 4, on the other hand, depicts a bottom-emitting organic electroluminescent device D of the double heterostructure, which has a multilayer structure formed of a light-transmitting anode 2, an organic layer 5b, and a cathode 3 stacked one over another on a light-transmitting substrate 1. The organic layer 5b is composed of a hole transport layer 10, a luminescent layer 11 and an electron transport layer 12. The multilayer structure is sealed with a protective layer 4.

When a DC voltage is impressed across the anode 2 and the cathode 3 in the organic electroluminescent device D depicted in FIG. 4, holes injected from the anode 2 and electrons injected from the cathode 3 are caused to reach the luminescent layer 11 through the hole transport layer 10 and the electron transport layer 12, respectively. As a result, recombination of electrons and holes takes place in the luminescent layer 11 to form singlet excitons, from which emission of light of a predetermined wavelength is produced.

In each of the above-mentioned organic electroluminescent devices C, D, a light-transmitting material such as glass or plastics can be used as the substrate 1 as desired. When the organic electroluminescent device is used in combination with another display device or when a plurality of multilayer structures as shown in FIG. 3 or FIG. 4 are arranged in the form of a matrix, for example, the substrate may be used in common. Further, the devices C and D can each take either a transmission-type structure or a reflection-type structure.

The anode 2 is a transparent electrode, and ITO, $SnO_2$ or the like can be used. Between the anode 2 and the hole transport layer 6 (or the hole transport layer 10), a thin film made of an organic material or an organometallic compound may be arranged to improve the charge injection efficiency. When the protective layer 4 is formed of a conductive material such as a metal, the anode 2 may be provided on side walls thereof with insulating films, respectively.

In the organic electroluminescent device C, the organic layer 5a is formed of the hole transport layer 6 and electron transport layer 7 stacked together. The above-described aminostyrylnaphthalene compound may be incorporated in one or both of these transport layers to convert them into a luminescent, hole transport layer 6 and/or a luminescent, electron transport layer 7. In the organic electroluminescent device D, on the other hand, the organic layer 5b is formed of the hole transport layer 10, the luminescent layer 11 with the above-described aminostyrylnaphthalene compound contained therein, and the electron transport layer 12, all of which are stacked together. In addition to this stacked structure, the organic layer 5b can take a variety of other stacked structures. For example, one or both of the hole transport layer and electron transport layer may be modified into luminescent transport layer or layers.

Further, each hole transport layer may be formed of plural hole transporting materials stacked in layers one over another such that the hole transport layer is provided with improved hole transporting ability.

In the organic electroluminescent device C, the luminescent layer may be the luminescent, electron transport layer 7. Depending on a voltage impressed from a power supply 8, however, light may be emitted at the hole transport layer 6 or at its interfaces. In the organic electroluminescent device D, the luminescent layer may also be either the electron transport 12 or the hole transport layer 10 in addition to the layer 11. To improve the light emitting performance, however, it is desired to adopt such a structure that a luminescent layer 11, which makes use of at least one fluorescent material, is held between a hole transport layer and an electron transport layer. As an alternative, the organic layer may be constructed into such a structure that the fluorescent material is incorporated in one or both of the hole transport layer and the electron transport layer. In each of these structures, it is possible to include a thin film, which can serve to control the transport of holes or electrons (for example, a hole blocking layer, exciton generating layer or the like), in the multilayer structure to improve its light emitting efficiency.

As a material for each cathode 3, an alloy of an active metal such as Li, Mg or Ca and a metal such as Ag, Al or In can be used. As an alternative, these metals may be used in a stacked structure. By selecting the thickness and material of the cathode as desired, an organic electroluminescent device suited for a specific application can be fabricated.

Each protective layer 4 acts as a sealing film. By providing the protective layer in such a structure as covering the organic electroluminescent device in its entirety, the charge injection efficiency and light emitting efficiency can be improved. Insofar as the organic electroluminescent device can be maintained air-tight, any desired material can be selected for the protective layer 4, including single metals and alloys of aluminum, gold, chromium and the like.

Figure 5:
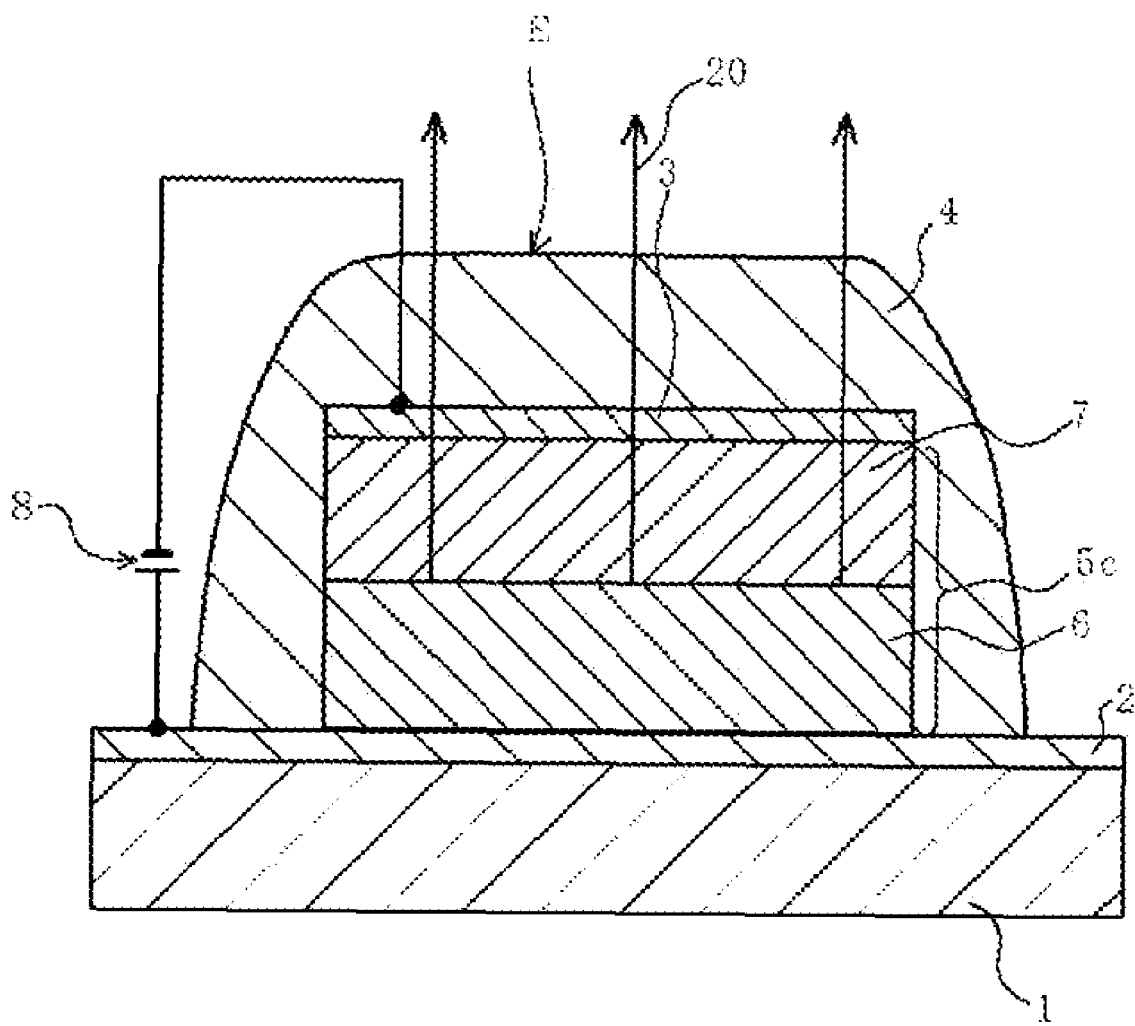
FIG. 5 is a schematic fragmentary cross-sectional view of an organic electroluminescent device according to a yet further embodiment of the present invention.

FIG. 5 shows a surface-emitting, organic electroluminescent device E of the single heterostructure, which has a multilayer structure formed of an anode 2, an organic layer 5c and a transparent or translucent cathode 3 stacked one over another on a substrate 1. The organic layer 5c is composed of a hole transport layer 6 and an electron transport layer 7. The multilayer structure is sealed with a protective layer 4. In this embodiment, emitted light 20 of a predetermined wavelength is produced from an interface between the hole transport layer 6 and the electron transport layer 7, and this emitted light is observed from the side of the cathode 3 or the protective layer 4.

Figure 6:
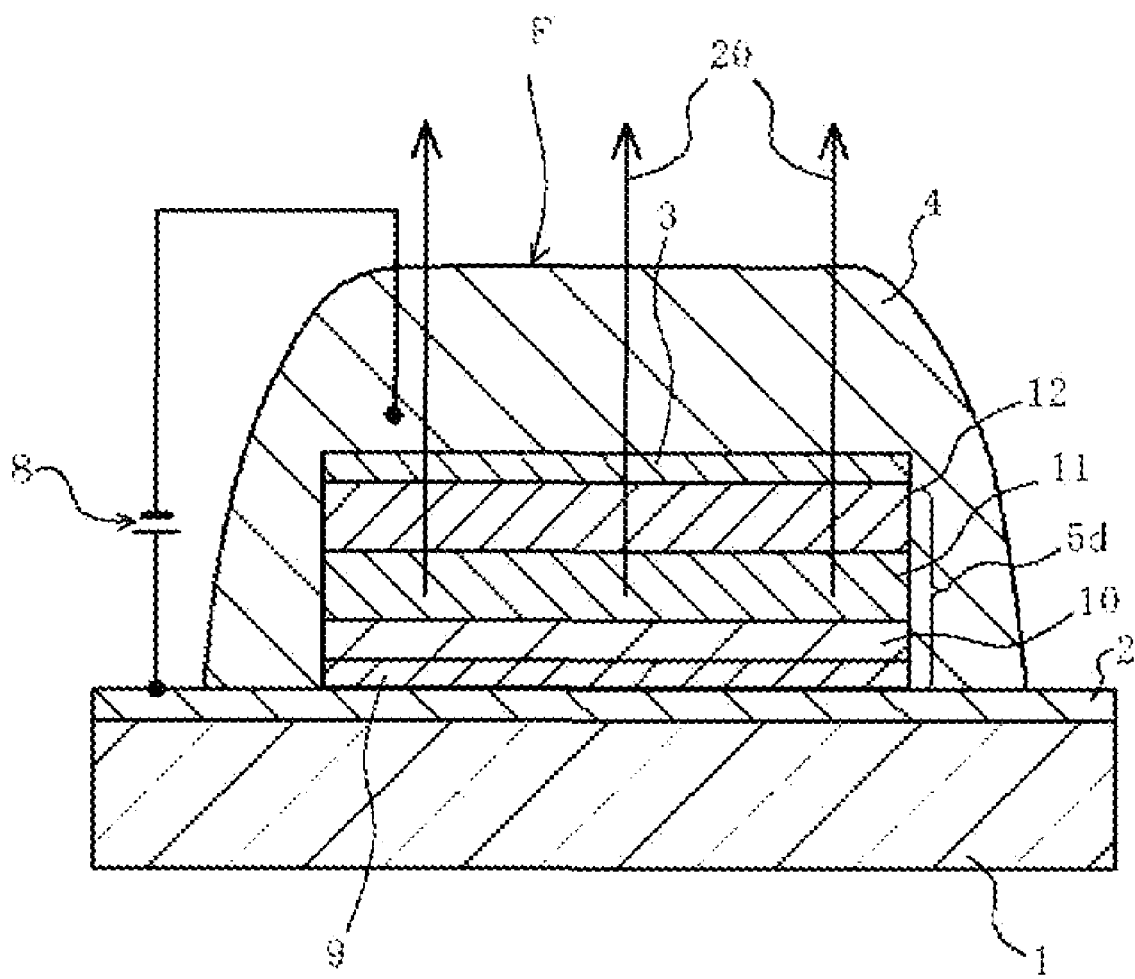
FIG. 6 is a schematic fragmentary cross-sectional view of an organic electroluminescent device according to a still yet further embodiment of the present invention.

FIG. 6 illustrates a surface-emitting, organic electroluminescent device F, which has a multilayer structure formed of an anode 2, an organic layer 5d and a transparent or translucent cathode 3 stacked one over another on a substrate 1. The organic layer 5d is composed of a hole injection layer 9, a hole transport layer 10, a luminescent layer 11 and an electron transport layer 12. The multilayer structure is sealed with a protective layer 4. Similarly to the organic electroluminescent device depicted in FIG. 4, recombination of electrons and holes also takes place in the luminescent layer 11 in this organic electroluminescent device to form excitons, from which emission of light of a predetermined wavelength is produced.

In each of the organic electroluminescent devices E, F, the substrate 1 can be formed by using a light-reflecting material such as Ag, Au, Al, Cr, In or the like or an alloy thereof as desired. When the organic electroluminescent device is used in combination with another display device or when a plurality of multilayer structures as shown in FIG. 5 or FIG. 6 are arranged in the form of a matrix, the substrate may be used in common.

The anode 2 on the substrate 1, on the other hand, is a reflective electrode. Ag, Au, Al, Cr or In or an alloy or the like thereof can be used. It is also possible to use ITO or the like by stacking the same. In view of film formability and reflectivity, its thickness may be set preferably at 50 nm or greater but not greater than 200 nm. When such an anode is used, the material of the substrate 1 is not limited to the above-described light-reflecting material, and a transparent or translucent material such as glass may be used.

As illustrated in FIG. 6, a hole injection layer 9 made of an inorganic material, an organic material or an organometallic compound may be arranged between the anode 2 and the hole transport layer 10 (or hole transport layer 6) to improve the charge injection efficiency. When the protective layer 4 is formed of a conductive material such as a metal, the anode 2 may be provided on side walls thereof with insulating films for insulation separation.

The organic layer 5c in the organic electroluminescent device E is an organic layer formed of the hole transport layer 6 and the electron transport layer 7 stacked one over the other. One or both of these transport layers may be arranged as mixed layer or layers with above-described aminostyrylnaphthalene compound contained therein such that a light-emitting, hole transport layer 6 and/or electron transport layer 7 are formed. The organic layer 5d in the organic electroluminescent device F is an organic layer formed of the hole transport layer 10, the luminescent layer 11, which is formed of a mixture with the above-described aminostyrylnaphthalene compound contained therein, and the electron transport layer 12 stacked one over another. In addition to this multilayer structure, various multilayer structures can be adopted. For example, one or both of the hole transport layer and electron transport layer may be formed to emit light.

To improve the hole transporting ability of each hole transport layer, the hole transport layer may be arranged as a hole transport layer formed of plural hole-transporting materials stacked in layers one over another.

In the organic electroluminescent device E, the luminescent layer may be the luminescent, electron transport layer 7. Depending on a voltage impressed from the power supply 8, however, light may be emitted at the hole transport layer 6 or at its interfaces. In the organic electroluminescent device F, the luminescent layer may also be either the electron transport 12 or the hole transport layer 10 in addition to the layer 11. To improve the light emitting performance, however, it is desired to adopt such a structure that a luminescent layer 11, which makes use of at least one fluorescent material, is held between a hole transport layer and an electron transport layer. As an alternative, the organic layer may be constructed into such a structure that the fluorescent material is incorporated in one or both of the hole transport layer and the electron transport layer. In each of these structures, it is possible to include a thin film, which can serve to control the transport of holes or electrons (for example, a hole blocking layer, exciton generating layer or the like), in the multilayer structure to improve its light emitting efficiency.

As a material for each cathode 3, an alloy of an active metal such as Li, Mg or Ca and a metal such as Ag, Al or In can be used. As an alternative, these metals may be used in a stacked structure. By selecting the thickness and material of the cathode as desired, an organic electroluminescent device suited for a specific application can be fabricated. Desirably, however, the thickness of the cathode may range from 0.5 to 15 nm with a range of from 0.5 to 5 nm or so being more desired.

Each protective layer 4 acts as a sealing film. By providing the protective layer in such a structure as covering the organic electroluminescent device in its entirety, the charge injection efficiency and light emitting efficiency can be improved. Insofar as the organic electroluminescent device can be maintained air-tight, any desired material can be selected for the protective layer 4, including single metals, alloys, compounds and the like such as aluminum, gold, chromium, silicon oxide, silicon nitride and the like.

In each of the above-described organic electroluminescent devices E, F, the luminescent layer is held between the anode and the cathode, and emitted light causes multiple interference between the anode and the cathode. By suitably choosing optical characteristics of the anode and cathode, such as their reflectivities and transmittances, and the thickness of the organic layer held between the anode and the cathode, multiple interference effect can be used positively such that the wavelength of light emitted from each of the devices E, F can be controlled. This makes it possible to improve the chromaticy of light to be emitted. With respect to the mechanism of this multiple interference effect, reference may be had to J. Yamada et al, AM-LCD Digest of Technical Papers, OD-2, 77-80, 2002.

A current to be impressed to each of the above-described organic electroluminescent devices is generally a direct current, but instead, a pulsed current or an alternating current may be used. Neither the current value nor the voltage value are particularly limited insofar they fall within such ranges that the device would remain undamaged. In view of the power consumption and service life of the organic electroluminescent device, however, it is desired to make the organic electroluminescent device efficiently emit light with as smaller electric energy as possible.

Figure 7:
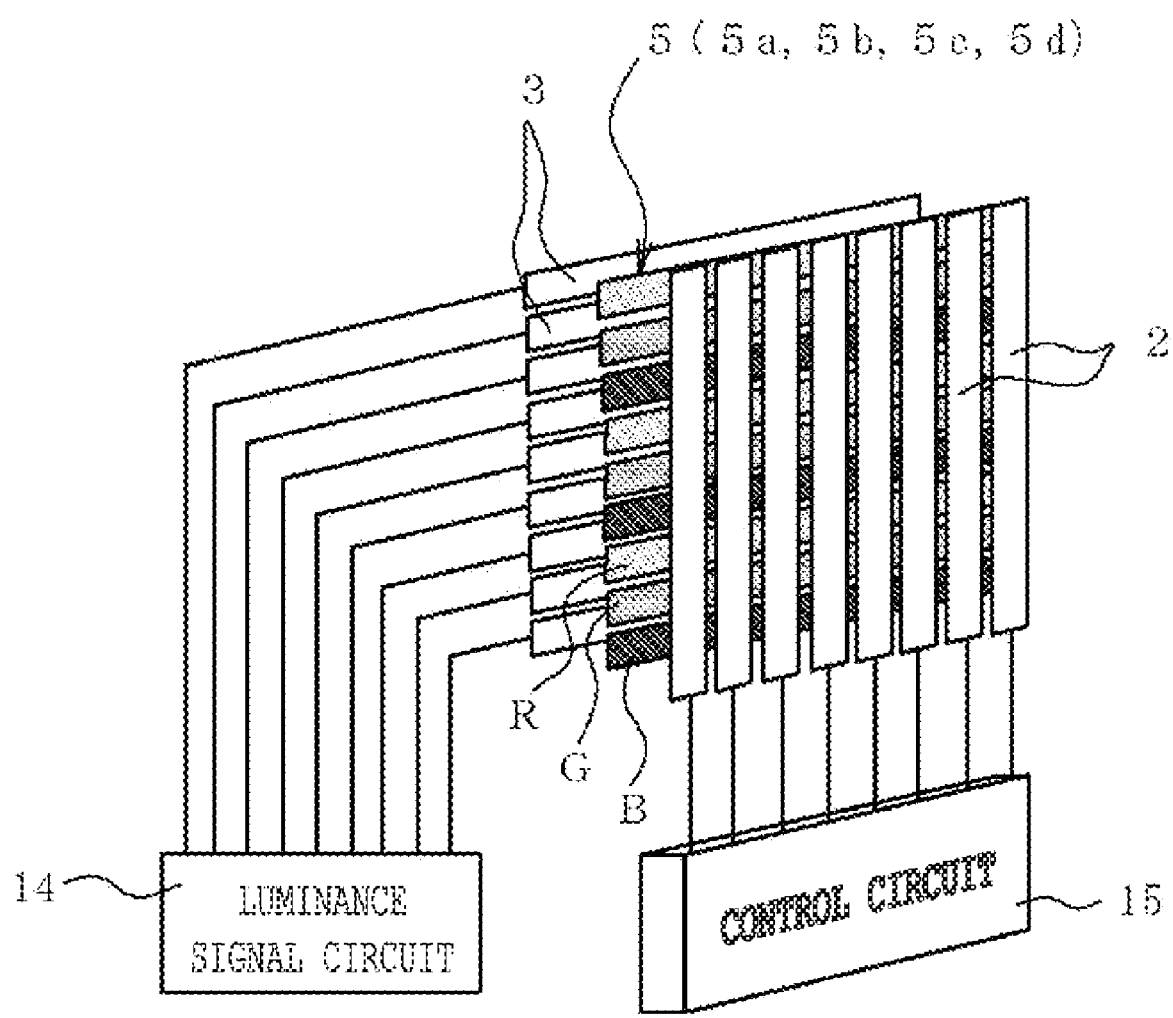
FIG. 7 is a construction diagram of a full-color flat display making use of an organic electroluminescent device according to the present invention.

FIG. 7 shows an illustrative construction of a flat display making use of an organic electroluminescent device according to the present invention. For example, in the case of a full-color display as depicted in the drawing, an organic layer 5 (5a, 5b) which can emit primaries of red (R), green (G) and blue (B) are arranged between cathodes 3 and anodes 2. The cathodes 3 and anodes 2 can be arranged in the form of stripes crossing each other. By a luminance signal circuit 14 and a control circuit 15 equipped with a built-in register, signal voltages are selectively impressed to the cathodes 3 and anodes 2 such that light is emitted from the organic layers at positions (pixels) where the selected cathodes 3 and anodes 2 intersect with each other in a single matrix system or active matrix system.

Described specifically, FIG. 7 shows by way of example an 8×3 RGB single matrix, in which stacked layers 5 each formed of a hole transport layer and at least one of a luminescent layer and electron transport layer are arranged between the cathodes 3 and the anodes 2 (see FIG. 3, FIG. 4, FIG. 5 or FIG. 6). The cathodes and anodes are constructed such that they are patterned in the form of stripes and are arranged at right angles relative to each other in the form of a matrix and, by the control circuit 15 equipped with the built-in shift register and the luminance signal circuit 14, signal voltages are impressed in time sequence to emit light at their crossing positions. EL devices of such a construction can also be used as picture reproducers, to say nothing of displays for characters, signs and the like. Further, the striped patterns of the cathodes 3 and anodes 2 can be arranged for each of red (R), green (G) and blue (B) to construct a multicolor or full-color, full solid-state flat panel display.

EXAMPLES

Certain examples of the present invention will next be described, although the present invention shall not be limited to them.

Example 1

A bottom-emitting, organic electroluminescent device of the single heterostructure was fabricated by using the compound of the above-described structural formula (20)-17 as a luminescent, electron transport layer and 4,4'-bis[N,N'-di(1-naphthyl)-N,N'-diphenyl]biphenyldiamine (α-NPD) of the below-described structural formula as a hole transport layer.

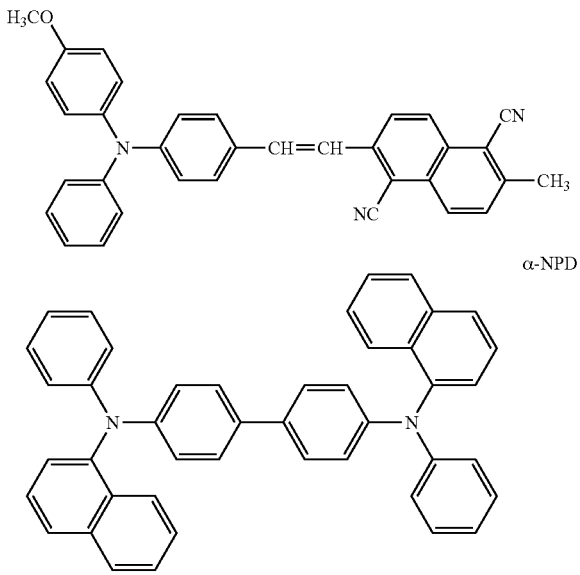

Structural formula (20)-17

α-NPD

Firstly, a 30 mm×30 mm glass substrate with a 100-nm thick ITO anode formed on a surface thereof was set in a vacuum evaporation system. A metal mask having a plurality of 2.0 mm×2.0 mm unit openings formed therethrough was disposed as an evaporation mask in a proximity of the substrate, and by vacuum evaporation, α-NPD as a hole transporting material was deposited to a thickness of 140 nm under a vacuum of $10^{-4}$ Pa or lower. Further, the compound of the above structural formula (20)-35 was deposited as a luminescent, electron transporting material to a thickness of 55 nm in contact with the hole transport layer. The deposition rate was set at 0.2 nm/sec in each of the above vacuum evaporation steps.

As cathode materials, Mg and Ag were adopted. By vacuum evaporation, they were also deposited at deposition rates of 1 nm/sec to thicknesses of 50 nm (Mg film) and 150 nm (Ag film), respectively, to form a stacked film of Mg and Ag, so that an organic electroluminescent device was fabricated as illustrated in FIG. 3.

Figure 8:
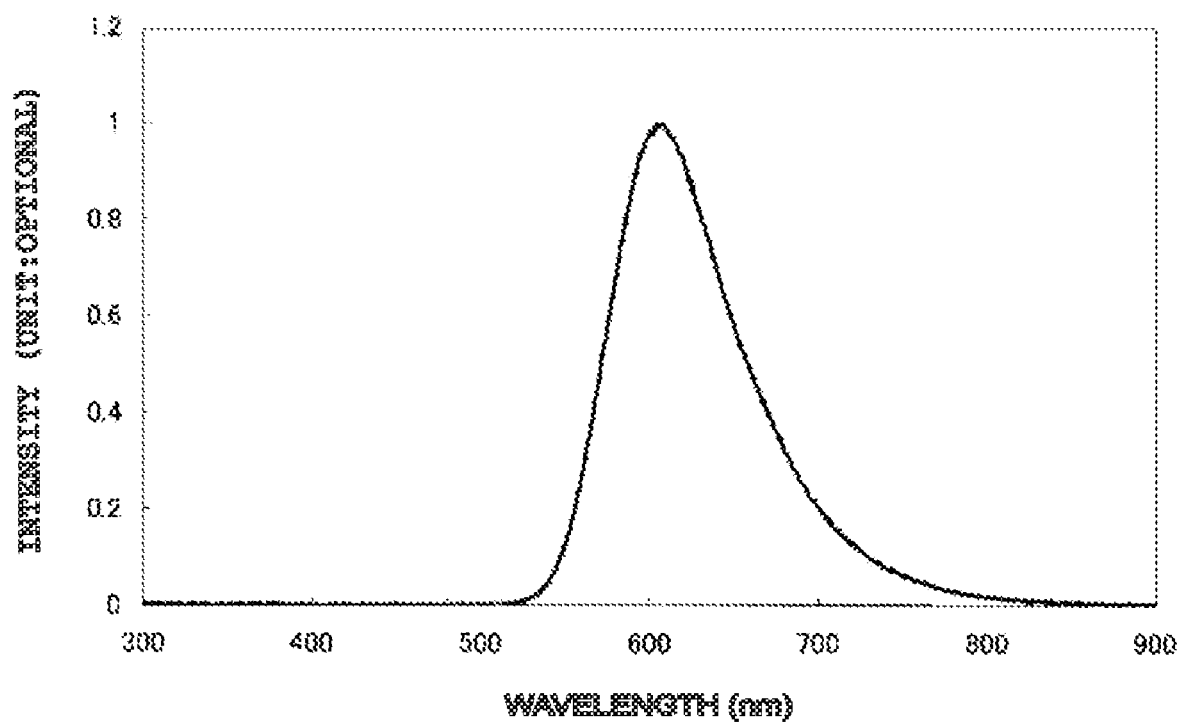
FIG. 8 is an emission spectrum diagram of an organic electroluminescent device fabricated in Example 1 of the present invention.
Figure 9:
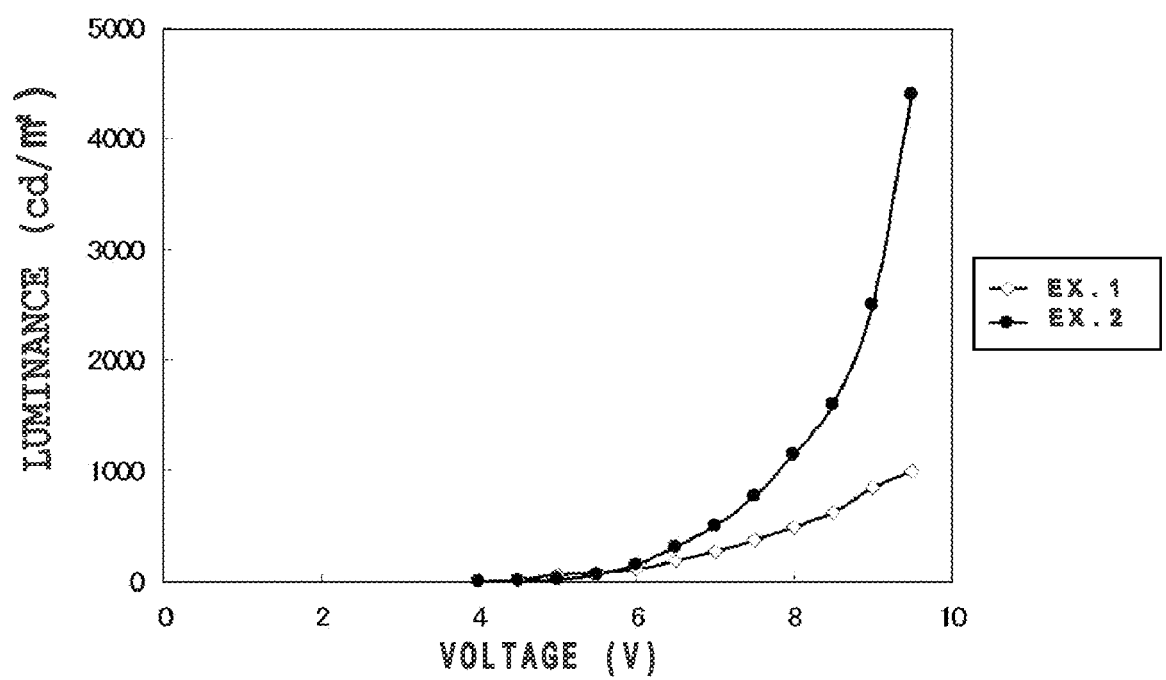
FIG. 9 is a voltage-luminance characteristic diagram of the organic electroluminescent device fabricated in Example 1 of the present invention.

To the organic electroluminescent device fabricated as described above, a forward bias d.c. voltage was applied in a nitrogen atmosphere to evaluate its light emitting characteristics. Emitted light had a red color. As a result of spectrometry, a spectrum having an emission peak around 610 nm was obtained. The electroluminescent spectrum is shown in FIG. 8. In the spectrometry, a spectroscope manufactured by OTSUKA ELECTRONICS CO., LTD. and equipped with a photodiode array as a detector was used. In addition, a voltage-luminescence measurement was conducted. As depicted in FIG. 9, a luminance of 490 $cd/m^2$ was obtained at 8 V.

After the fabrication, the organic electroluminescent device was left over for 1 month under a nitrogen atmosphere, but no degradation was observed on the device. Further, the organic electroluminescent device was subjected to forced degradation at an initial luminance of 100 $cd/m^2$ by applying a current at a constant value to continuously emit light. It took 800 hours until the luminance dropped to half.

Example 2

A bottom-emitting, organic electroluminescent device of the double heterostructure was fabricated by using the above-described α-NPD as a hole transport layer and the compound of the above-described structural formula (20)-17 as a luminescent layer.

Firstly, a 30 mm×30 mm glass substrate with a 100-nm thick ITO anode formed on a surface thereof was set in a vacuum evaporation system. A metal mask having a plurality of 2.0 mm×2.0 mm unit openings formed therethrough was disposed as an evaporation mask in a proximity of the substrate, and by vacuum evaporation, α-NPD as a hole transporting material was deposited to a thickness of 140 nm under a vacuum of $10^{-4}$ Pa or lower. Further, the compound of the above structural formula (20)-35 was deposited as a light emitting material to a thickness of 40 nm in contact with the hole transport layer. The deposition rate was set at 0.2 nm/sec in each of the above vacuum evaporation steps. As an electron transport layer, tris(8-hydroxyquinoline)aluminum ($Alq_3$) of the below-described structural formula was deposited further in contact with the luminescent layer. The electron transport layer made of $Alq_3$ was deposited to a thickness of 50 nm. The deposition rate was set at 0.2 nm/sec.

As cathode materials, Mg and Ag were adopted. By vacuum evaporation, they were also deposited at deposition rates of 1 nm/sec to thicknesses of 50 nm (Mg film) and 150 nm (Ag film), respectively, to form a stacked film of Mg and Ag, so that an organic electroluminescent device was fabricated as illustrated in FIG. 4.

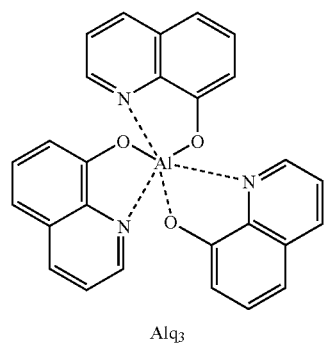

$Alq_3$

To the organic electroluminescent device fabricated as described above, a forward bias d.c. voltage was applied in a nitrogen atmosphere to evaluate its light emitting characteristics. Emitted light had a red color. As a result of spectrometry, an emission spectrum similar to that obtained in Example 1 was obtained. In the spectrometry, a spectroscope manufactured by OTSUKA ELECTRONICS CO., LTD. and equipped with a photodiode array as a detector was used. In addition, a voltage-luminescence measurement was conducted. As depicted in FIG. 9, a high luminance of 1,150 cd/m$^2$ was obtained at 8 V.

After the fabrication, the organic electroluminescent device was left over for 1 month under a nitrogen atmosphere, but no degradation was observed on the device. Further, the organic electroluminescent device was subjected to forced degradation at an initial luminance of 100 cd/m$^2$ by applying a current at a constant value to continuously emit light. It took 1,300 hours until the luminance dropped to half.

Example 3

A surface-emitting, organic electroluminescent device was fabricated by using, as a light-emitting, electron transport layer, a mixed layer of the compound of the above-described structural formula (20)-17 and Alq$_3$ of the above-described structural formula.

Firstly, a 30 mm×30 mm glass substrate was set in a vacuum evaporation system. The glass substrate carried on a surface thereof anodes composed of a 100-nm thick silver alloy and a 10-nm thick ITO formed as a film on the silver alloy. A metal mask having a plurality of 2.0 mm×2.0 mm unit openings formed therethrough was disposed as an evaporation mask in a proximity of the substrate. By vacuum evaporation under a vacuum of 10$^{-4}$ Pa or lower, 2-TNATA of the below-described structural formula was deposited as a hole injection layer, for example, to a thickness of 20 nm, and over the hole injection layer, α-NPD was further deposited as a hole transport layer, for example, to a thickness of 43 nm. The deposition rate was set at 0.1 nm/sec in each of the above vacuum evaporation steps.

In addition, the above-described compound of the structural formula (20)-17 and as an electron transporting material, Alq$_3$ were deposited as a mixed layer at an evaporation rate ratio of 1:1 in contact with the hole transport layer. The thickness of the electron transport layer (which also serves as a luminescent layer) made of the compound of the structural formula (20)-17 and Alq$_3$ was set, for example, at 30 nm, and their deposition rates were each set at 0.2 nm/sec.

Over the electron transport layer, Alq$_3$ was deposited further as an electron transport layer, for example, to a thickness of 36 nm.

As a cathode material, a mixed film of Mg and Ag was adopted. By vacuum evaporation, the mixed film was also formed, for example, to a thickness of 12 nm while controlling the mixing ratio of Mg to Ag at 5:1. As a result, an organic electroluminescence device was fabricated as illustrated in FIG. 6.

To the organic electroluminescent device fabricated as described above, a forward bias d.c. voltage was applied in a nitrogen atmosphere to evaluate its light emitting characteristics. Emitted light had a red color. As a result of spectrometry in a similar manner as in Example 1, a spectrum having an emission peak around 610 nm was obtained. In addition, a voltage-luminescence measurement was conducted. A luminance of 1,300 cd/m$^2$ was obtained at 8 V.

After the fabrication, the organic electroluminescent device was left over for 1 month under a nitrogen atmosphere, but no degradation was observed on the device. Further, the organic electroluminescent device was subjected to forced degradation at an initial luminance of 100 cd/m$^2$ by applying a current at a constant value to continuously emit light. It took 2,050 hours until the luminance dropped to half.

Example 4

Synthesis Example of (Aminostyryl)naphthalene Compound

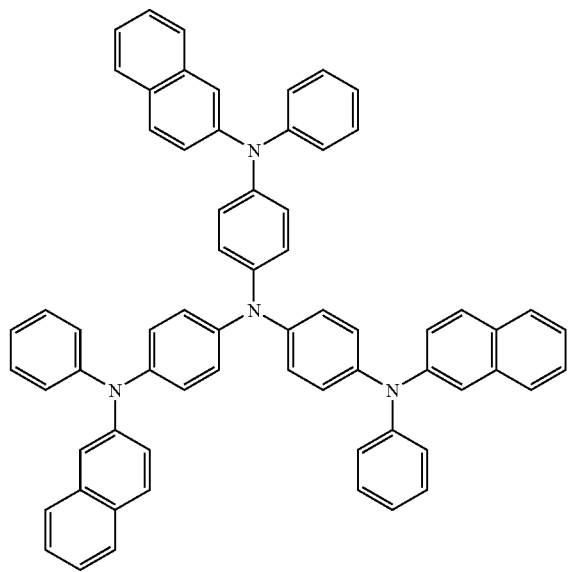

2-TNANA

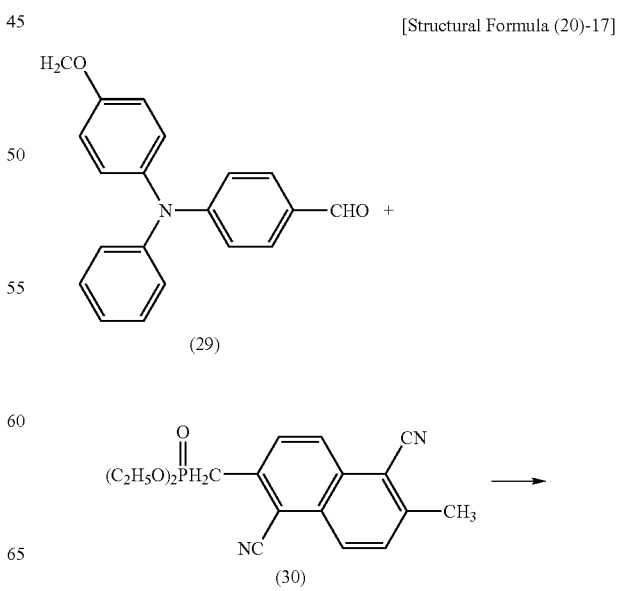

[Structural Formula (20)-17]

-continued

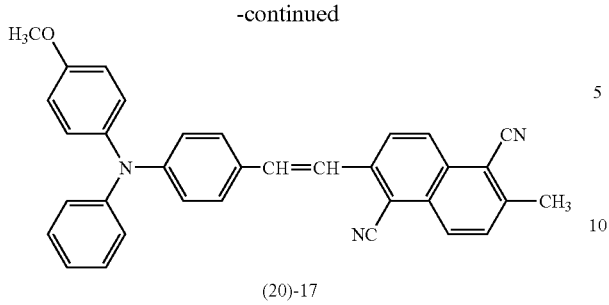

(20)-17

Under a nitrogen atmosphere, a Witting-Horner reagent (30) (7.00 g, 20.3 mmol) was suspended in methanol (100 mL) over an ice bath. Under stirring, sodium methoxide (1.20 g, 22.2 mmol) was added little by little, followed by stirring for 30 minutes. 4-[N,N'-(4-methyldiphenyl)]aminobenzaldehyde (29) (5.60 g, 18.5 mmol) was added in two portions, and the temperature of the resulting mixture was allowed to rise, as was, from 0° C. to room temperature, at which the mixture was stirred for 6 hours.

Figure 10:
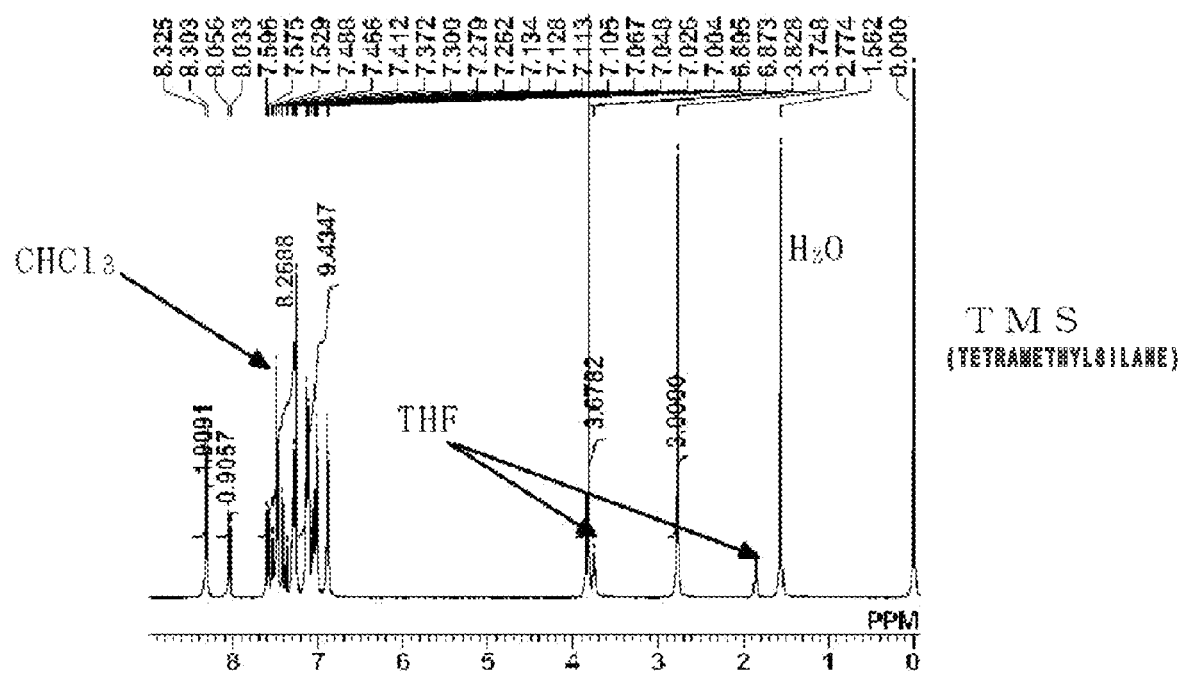
FIG. 10 is a $^1$H-NMR spectrum diagram of an aminostyrylnaphthalene compound produced in Example 1 of the present invention and suited for use in an organic electroluminescent device.

The resulting precipitate was collected by filtration, and then recrystallized three times from tetrahydrofuran (THF)-toluene-methanol to afford an orange-color powder (3.05 g). The product was identified to be the target compound by $^{1}$H-NMR and FAB-MS analyses (isolation yield: 30%). Its identification data were as described below, and its $^{1}$H-NMR spectrum is presented in FIG. 10.

$^{1}$H-NMR (400 MHz, CDCl$_{3}$) δ(ppm): 2.77 (s, 3H), 3.75 (s, 3H), 6.88 (d, 2H), 7.00-7.13 (m, 7H), 7.27-7.53 (m, 6H), 7.59 (d, 1H), 8.04 (d, 1H), 8.31 (d, 2H).

Incidentally, a solution of the product in THF had a visible absorption maximum at 437 nm and a fluorescence maximum wavelength at 612 nm. The relative fluorescence quantum yield of the product in dioxane was 0.97, that is, very high.

According to the present invention, the aminostyrylnaphthalene compound represented by the formula [A] is excellent in light emitting properties, and moreover, shows amorphous properties advantageous for film formability by vacuum deposition or the like and also durability. The use of the aminostyrylnaphthalene compound makes it possible to provide an organic electroluminescent device capable of producing high-luminance and stable emission of light at an optimal wavelength.

What is claimed is:

1. A process for the production of an aminostyrylnaphthalene compound represented by formula [A]:

Formula [A]

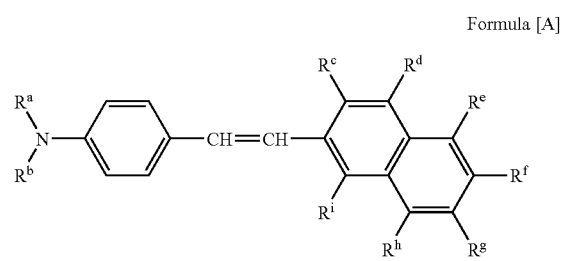

wherein, $R^{a}$ and $R^{b}$ may be the same or different and each independently represents a substituted or unsubstituted aryl group, $R^{c}$, $R^{d}$, $R^{e}$, $R^{g}$, $R^{h}$ and $R^{i}$ may be the same or different, at least one of $R^{c}$, $R^{d}$, $R^{e}$, $R^{g}$, $R^{h}$ and $R^{i}$ independently represents a hydrogen atom, a cyano group, a nitro group, a trifluoromethyl group or a halogen atom, and the remaining one or ones of $R^{c}$, $R^{d}$, $R^{e}$, $R^{g}$, $R^{h}$ and $R^{i}$, if any, are each a hydrogen atom, a cyano group, a nitro group, a trifluoromethyl group or a halogen atom, and $R^{f}$ represents an alkyl selected from the group consisting of methyl, ethyl n-propyl, i-propyl, n-butyl, i-butyl, t-butyl and allyl, a substituted or unsubstituted alicyclic hydrocarbon group, a substituted or unsubstituted aryl group, a substituted or unsubstituted alkoxyl group, a substituted or unsubstituted alicyclic hydrocarbyloxy group or a substituted or unsubstituted aromatic hydrocarbyloxy group;

which method comprises subjecting a 4-aminobenzaldehyde represented by the following formula [B] and at least one of a phosphonate ester represented by the following formula [C] and a phosphonium represented by the following formula [D] to condensation:

Formula [B]

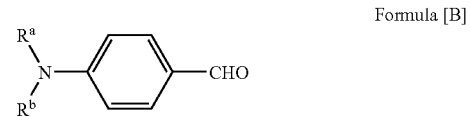

wherein, $R^{a}$ and $R^{b}$ have the same meanings as defined above,

Formula [C]

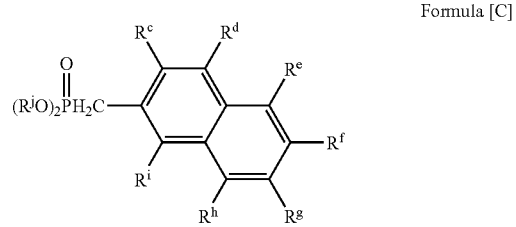

Formula [D]

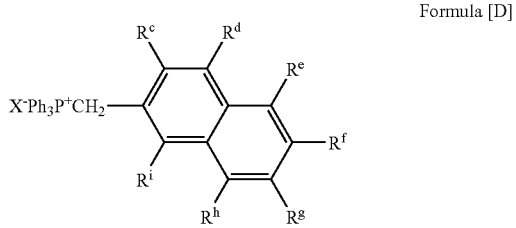

wherein, $R^{j}$ represents a hydrocarbon group, $R^{c}$, $R^{d}$, $R^{e}$, $R^{f}$, $R^{g}$, $R^{h}$ and $R^{i}$ have the same meanings as defined above, and X represents a halogen atom.

2. A process for the production of an aminostyrylnaphthalene compound represented by the formula [I], [II] or[III]:

Formula [I]

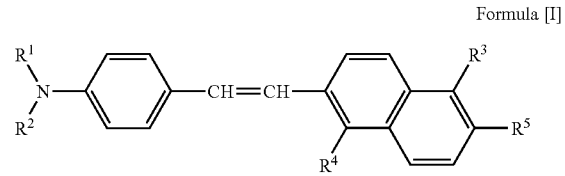

wherein, $R^1$ and $R^2$ may be the same or different and each independently represents a phenyl group represented by the following formula (1):

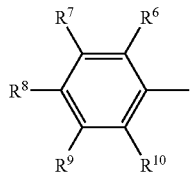

Formula (1)

wherein, $R^6$, $R^7$, $R^8$, $R^9$ and $R^{10}$ may be the same or different, at least one of $R^6$ to $R^{10}$ represents a hydrogen atom, a saturated or unsaturated hydrocarbon group having at least one carbon atom with a proviso that, when at least two adjacent ones of $R^6$ to $R^{10}$ each represents a saturated or unsaturated hydrocarbon group having at least one carbon atom, at least said two adjacent ones of $R^6$ to $R^{10}$ may be fused together to form a ring, a saturated or unsaturated hydrocarbyloxy group having at least one carbon atom, a saturated or unsaturated hydrocarbylamino group having at least one carbon atom, a trifluoromethyl group, a cyano group or a halogen atom, and the remaining one or ones of $R^6$ to $R^{10}$, if any, are each a hydrogen atom, a saturated or unsaturated hydrocarbon group having at least one carbon atom with a proviso that, when at least two adjacent ones of $R^6$ to $R^{10}$ each represents a saturated or unsaturated hydrocarbon group having at least one carbon atom, at least said two adjacent ones of $R^6$ to $R^{10}$ may be fused together to form a ring, a saturated or unsaturated hydrocarbyloxy group having at least one carbon atom, a saturated or unsaturated hydrocarbylamino group having at least one carbon atom, a trifluoromethyl group, a cyano group or a halogen atom, $R^3$ and $R^4$ may be the same or different, one of $R^3$ and $R^4$ represents a hydrogen atom, a cyano group, a nitro group, a trifluoromethyl group or a halogen atom, and the remaining one represents a hydrogen atom, a cyano group, a nitro group, a trifluoromethyl group or a halogen atom, and $R^5$ represents an alkyl selected from the group consisting of methyl, ethyl, n-propyl, i-propyl, n-butyl, i-butyl, t-butyl, and allyl, a substituted or unsubstituted, alicyclic hydrocarbon group, a substituted or unsubstituted aryl group, a substituted or unsubstituted alkoxyl group, a substituted or unsubstituted, alicyclic hydrocarbyloxy group, or a substituted or unsubstituted, aromatic hydrocarbyloxy group,

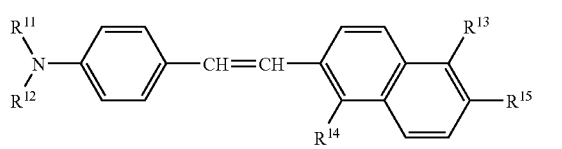

Formula [II]

wherein, $R^{11}$ and $R^{12}$ may be the same or different and each independently represents a naphthyl group represented by the following formula (2):

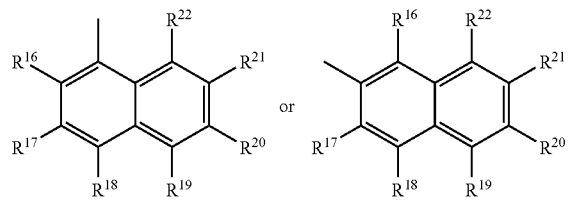

Formula (2)

wherein $R^{16}$, $R^{17}$, $R^{18}$, $R^{19}$, $R^{20}$, $R^{21}$ and $R^{22}$ maybe the same or different, at least one of $R^{16}$ to $R^{22}$ represents a hydrogen atom, a saturated or unsaturated hydrocarbon group having at least one carbon atom, a saturated or unsaturated hydrocarbyloxy group having at least one carbon atom, a saturated or unsaturated hydrocarbylamino group having at least one carbon atom, a trifluoromethyl group, a cyano group or a halogen atom, and the remaining one or ones of $R^{16}$ to $R^{22}$, if any, are each a hydrogen atom, a saturated or unsaturated hydrocarbon group having at least one carbon atom, a saturated or unsaturated hydrocarbyloxy group having at least one carbon atom, a saturated or unsaturated hydrocarbylamino group having at least one carbon atom, a trifluoromethyl group, a cyano group or a halogen atom, $R^{13}$ and $R^{14}$ may be the same or different, one of $R^{13}$ and $R^{14}$ represents a hydrogen atom, a cyano group, a nitro group, a trifluoromethyl group or a halogen atom, and the remaining one represents a hydrogen atom, a cyano group, a nitro group, a trifluoromethyl group or a halogen atom, and $R^{15}$ represents an alkyl selected from the group consisting of methyl, ethyl, n-propyl, i-propyl, n-butyl, i-butyl, t-butyl, and allyl, a substituted or unsubstituted, alicyclic hydrocarbon group, a substituted or unsubstituted aryl group, a substituted or unsubstituted alkoxyl group, a substituted or unsubstituted, alicyclic hydrocarbyloxy group, or a substituted or unsubstituted, aromatic hydrocarbyloxy group,

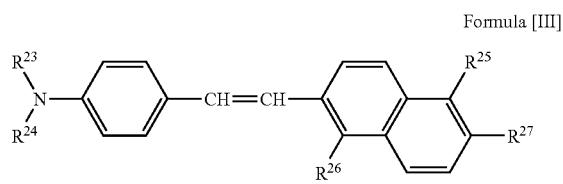

Formula [III]

wherein, $R^{23}$ is a phenyl group represented by the following formula (3):

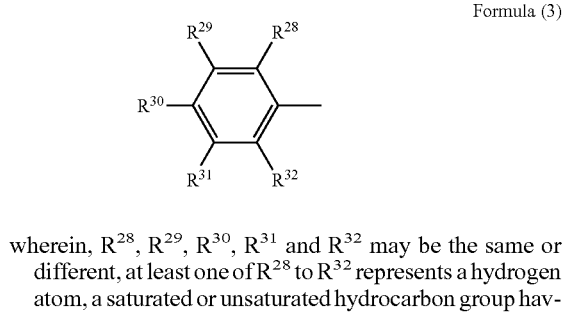

Formula (3)

wherein, $R^{28}$, $R^{29}$, $R^{30}$, $R^{31}$ and $R^{32}$ may be the same or different, at least one of $R^{28}$ to $R^{32}$ represents a hydrogen atom, a saturated or unsaturated hydrocarbon group having at least one carbon atom with a proviso that, when at least two adjacent ones of $R^{28}$ to $R^{31}$ each represents a saturated or unsaturated hydrocarbon group having at least one carbon atom, at least said two adjacent ones of $R^{28}$ to $R^{32}$ may be fused together to form a ring, a hydrocarbyloxy group having at least one carbon atom, a hydrocarbylamino group having at least one carbon atom, a trifluoromethyl group, a cyano group or a halogen atom, and the remaining one or ones of $R^{28}$ to $R^{32}$, if any, are each a hydrogen atom, a saturated or unsaturated hydrocarbon group having at least one carbon atom with a proviso that, when at least two adjacent ones of $R^{28}$ to $R^{32}$ each represents a saturated or unsaturated hydrocarbon group having at least one carbon atom, at least said two adjacent ones of $R^{28}$ to $R^{32}$ may be fused together to form a ring, a saturated or unsaturated hydrocarbyloxy group having at least one carbon atom, a saturated or unsaturated hydrocarbylamino group having at least one carbon atom, a trifluoromethyl group, a cyano group or a halogen atom, $R^{24}$ represents a naphthyl group represented by the following formula (4):

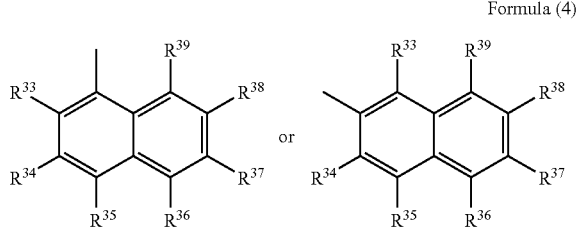

Formula (4)

wherein, $R^{33}$, $R^{34}$, $R^{35}$, $R^{36}$, $R^{37}$, $R^{38}$ and $R^{39}$ may be the same or different, at least one of $R^{33}$ to $R^{39}$ represents a hydrogen atom, a saturated or unsaturated hydrocarbon group having at least one carbon atom, a saturated or unsaturated hydrocarbyloxy group having at least one carbon atom, a saturated or unsaturated hydrocarbylamino group having at least one carbon atom, a trifluoromethyl group, a cyano group or a halogen atom, and the remaining one or ones of $R^{33}$ to $R^{39}$, if any, are each a hydrogen atom, a saturated or unsaturated hydrocarbon group having at least one carbon atom, a saturated or unsaturated hydrocarbyloxy group having at least one carbon atom, a saturated or unsaturated hydrocarbylamino group having at least one carbon atom, a trifluoromethyl group, a cyano group or a halogen atom, $R^{25}$ and $R^{26}$ may be the same or different, one of $R^{25}$ and $R^{26}$ represents a hydrogen atom, a cyano group, a nitro group, a trifluoromethyl group or a halogen atom, and the remaining one represents a hydrogen atom, a cyano group, a nitro group, a trifluoromethyl group or a halogen atom, and $R^{27}$ represents an alkyl selected from the group consisting of methyl, ethyl, n-propyl, i-propyl, n-butyl, n-butyl and allyl, a substituted or unsubstituted, alicyclic hydrocarbon group, a substituted or unsubstituted aryl group, a substituted or unsubstituted alkoxyl group, a substituted or unsubstituted, alicyclic hydrocarbyloxy group, or a substituted or unsubstituted, aromatic hydrocarbyloxy group;

which method comprises subjecting a 4-(N,N-diarylamino)benzaldehyde represented by the following formula [IV] and at least one of a phosphonate ester represented by the following formula [V] and a phosphonium represented by the following formula [VI] to condensation:

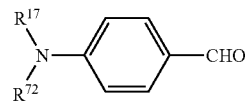

Formula [IV]

wherein, $R^{71}$ and $R^{72}$ each independently represents an aryl group corresponding to $R^1$, $R^2$, $R^{11}$, $R^{12}$, $R^{23}$ or $R^{24}$ as defined above,

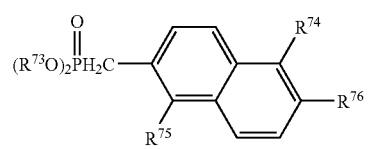

Formula [V]

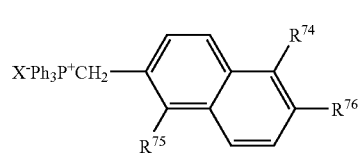

Formula [VI]

wherein, $R^{73}$ represents a hydrocarbon group, $R^{74}$ and $R^{75}$ each independently represents a group corresponding to $R^3$, $R^4$, $R^{13}$, $R^{14}$, $R^{25}$ or $R^{76}$ as defined above, $R^{76}$ represents a group corresponding to $R^5$, $R^{15}$ or $R^{27}$ as defined above, and X represents a halogen atom.

3. The process according to claim 1, wherein said condensation is conducted by the Wittig-Horner reaction, at least one of said phosphonate ester and said phosphonium is treated with a base in a solvent to form carbanions, and said carbanions and said 4-(N,N-diarylamino)benzaldehyde are subjected to condensation.

4. The process according to claim 1, wherein said condensation is conducted by the Wittig reaction, at least one of said phosphonate ester and said phosphonium is treated with a base in a solvent to form carbanions, and said carbanions and said 4-(N,N-diarylamino)benzaldehyde are subjected to condensation.

5. The process according to claim 2, wherein the aminostyrylnaphthalene compound is represented by one of the formula (5), (6), (7), (8), (9), (10), (11), (12), (13), (14), (15), (16) or (17):

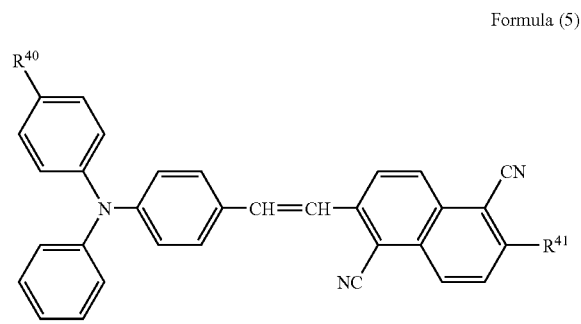

Formula (5)

wherein $R^{40}$ represents a saturated or unsaturated alkyl group having 1 to 6 carbon atoms or a substituted or unsubstituted aryl group, and $R^{41}$ has the same meaning as $R^5$, Formula (6)

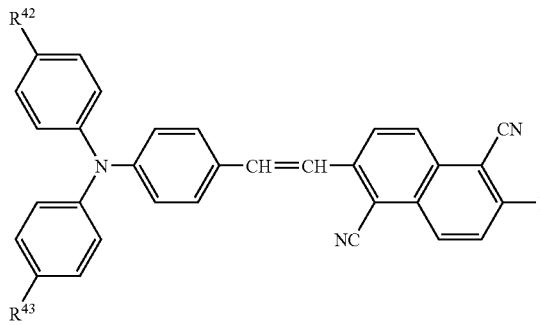

wherein $R^{42}$ and $R^{43}$ may be the same or different and each independently represents a saturated or unsaturated alkyl group having 1 to 6 carbon atoms or a substituted or unsubstituted aryl group, and $R^{44}$ has the same meaning as $R^5$, Formula (7)

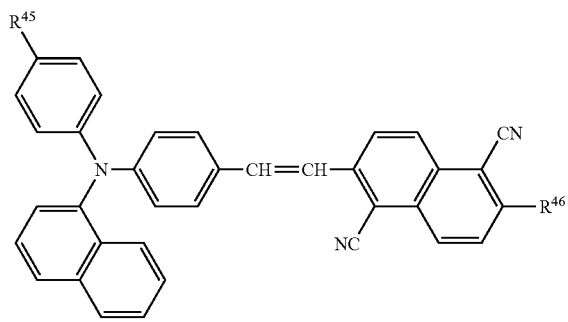

wherein $R^{45}$ represents a saturated or unsaturated alkyl group having 1 to 6 carbon atoms or a substituted or unsubstituted aryl group, and $R^{46}$ has the same meaning as $R^{27}$, Formula (8)

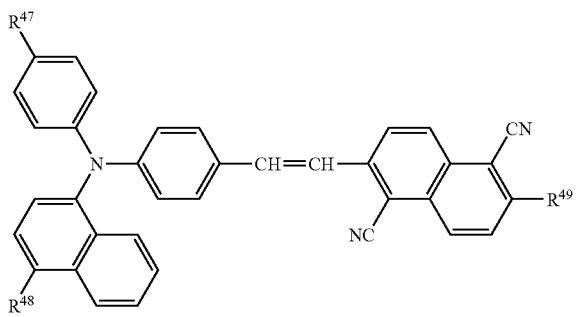

wherein $R^{47}$ and $R^{48}$ may be the same or different, one of $R^{47}$ and $R^{48}$ represents a saturated or unsaturated alkyl group having 1 to 6 carbon atoms or a substituted or unsubstituted aryl group, the remaining one of $R^{45}$ and $R^{48}$ represents a saturated or unsaturated alkyl group having 1 to 6 carbon atoms or a substituted or unsubstituted aryl group, and $R^{49}$ has the same meaning as $R^{27}$, Formula (9)

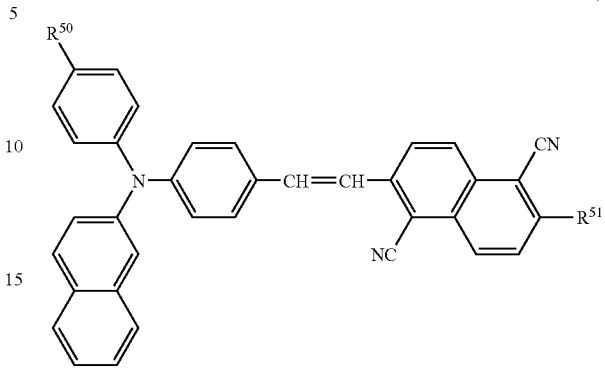

wherein $R^{50}$ represents a saturated or unsaturated alkyl group having 1 to 6 carbon atoms or a substituted or unsubstituted aryl group, and $R^{51}$ has the same meaning as $R^{27}$, Formula (10)

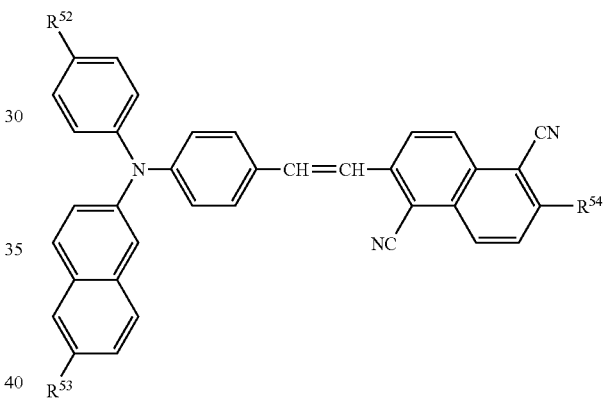

wherein $R^{52}$ and $R^{53}$ may be the same or different, one of $R^{52}$ and $R^{53}$ represents a saturated or unsaturated alkyl group having 1 to 6 carbon atoms or a substituted or unsubstituted aryl group, the remaining one of $R^{52}$ and $R^{53}$ represents a saturated or unsaturated alkyl group having 1 to 6 carbon atoms or a substituted or unsubstituted aryl group, and $R^{54}$ has the same meaning as $R^{27}$, Formula (11)

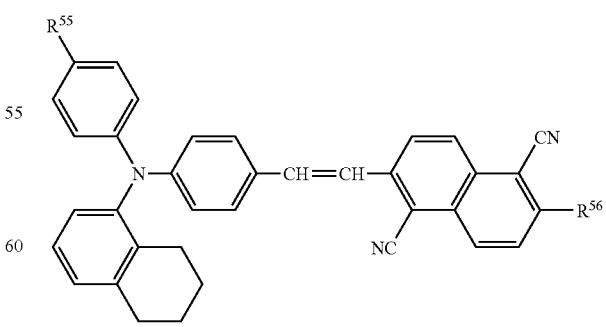

wherein $R^{55}$ represents a saturated or unsaturated alkyl group having 1 to 6 carbon atoms or a substituted or unsubstituted aryl group, and $R^{56}$ has the same meaning as $R^5$, Formula (12)

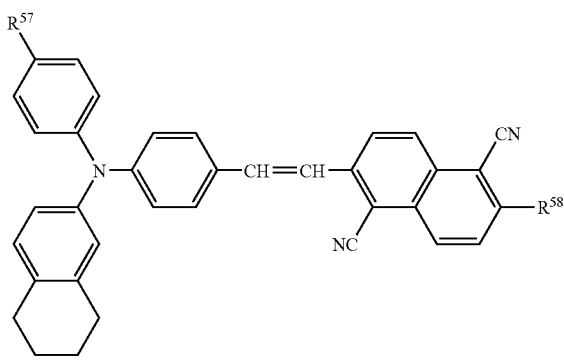

wherein $R^{57}$ represents a saturated or unsaturated alkyl group having 1 to 6 carbon atoms or a substituted or unsubstituted aryl group, and $R^{58}$ has the same meaning as $R^5$, Formula (13)

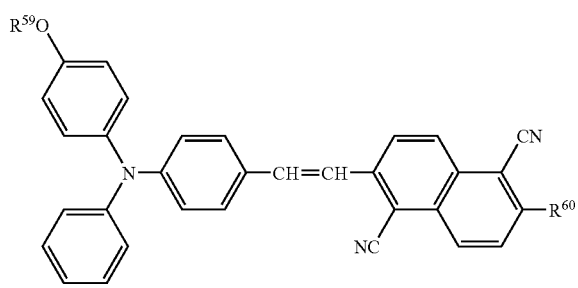

wherein $R^{59}$ represents a saturated or unsaturated alkyl group having 1 to 6 carbon atoms or a substituted or unsubstituted aryl group, and $R^{60}$ has the same meaning as $R^5$, Formula (14)

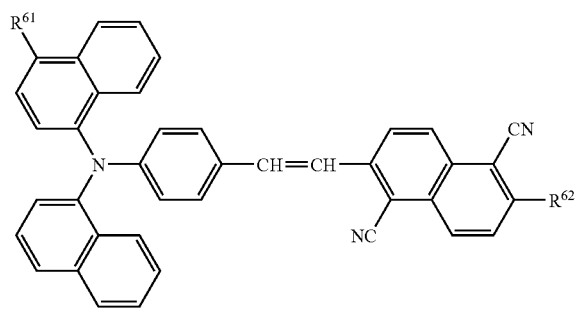

wherein $R^{61}$ represents a saturated or unsaturated alkyl group having 1 to 6 carbon atoms or a substituted or unsubstituted aryl group, and $R^{62}$ has the same meaning as $R^{15}$, Formula (15)

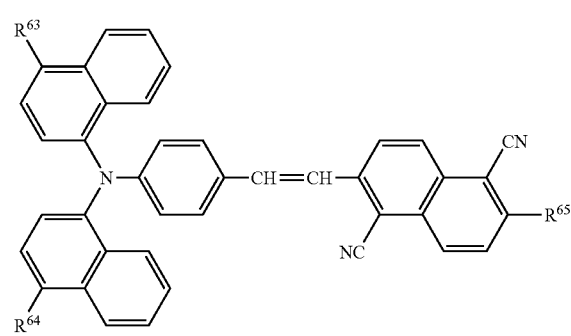

wherein $R^{63}$ and $R^{64}$ may be the same or different, one of $R^{63}$ and $R^{64}$ represents a saturated or unsaturated alkyl group having 1 to 6 carbon atoms or a substituted or unsubstituted aryl group, the remaining one of $R^{63}$ and $R^{64}$ represents a saturated or unsaturated alkyl group having 1 to 6 carbon atoms or a substituted or unsubstituted aryl group, and $R^{65}$ has the same meaning as $R^{15}$, Formula (16)

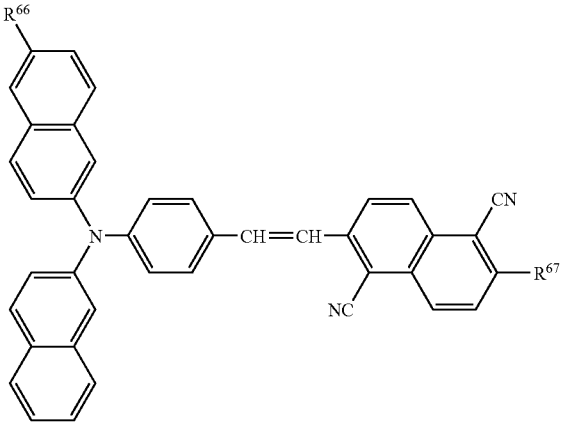

wherein $R^{66}$ represents a saturated or unsaturated alkyl group having 1 to 6 carbon atoms or a substituted or unsubstituted aryl group, and $R^{67}$ has the same meaning as $R^{15}$, Formula (17)

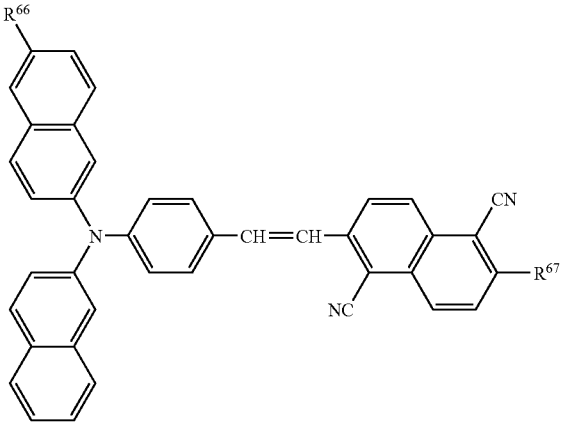

wherein $R^{68}$ and $R^{69}$ may be the same or different, one of $R^{68}$ and $R^{69}$ represents a saturated or unsaturated alkyl group having 1 to 6 carbon atoms or a substituted or unsubstituted aryl group, the remaining one of $R^{68}$ and $R^{69}$ represents a saturated or unsaturated alkyl group having 1 to 6 carbon atoms or a substituted or unsubstituted aryl group, and $R^{70}$ has the same meaning as $R^{15}$.

* * * * *